(12) United States Patent
Sauer et al.

(10) Patent No.: US 9,328,359 B2
(45) Date of Patent: May 3, 2016

(54) FERMENTATION PROCESS FOR PRODUCING CHEMICALS

(71) Applicant: Vogelbusch GmbH, Vienna (AT)

(72) Inventors: Michael Sauer, Vienna (AT); Hans Marx, Moerbisch am See (AT); Stefan Pfluegl, Vienna (AT); Diethard Mattanovich, Vienna (AT)

(73) Assignee: VOGELBUSCH GMBH, Vienna (AT)

( * ) Notice: Subject to any disclaimer, the term of this patent is extended or adjusted under 35 U.S.C. 154(b) by 0 days.

(21) Appl. No.: 14/355,253

(22) PCT Filed: Nov. 5, 2012

(86) PCT No.: PCT/EP2012/071812
§ 371 (c)(1),
(2) Date: Apr. 30, 2014

(87) PCT Pub. No.: WO2013/064682
PCT Pub. Date: May 10, 2013

(65) Prior Publication Data
US 2014/0308718 A1    Oct. 16, 2014

(30) Foreign Application Priority Data
Nov. 3, 2011    (EP) ..................... 11187720

(51) Int. Cl.
*C12P 7/18*    (2006.01)
*C12R 1/225*    (2006.01)
*C12N 1/32*    (2006.01)
*C12N 9/04*    (2006.01)
*C12P 7/56*    (2006.01)

(52) U.S. Cl.
CPC ... *C12P 7/18* (2013.01); *C12N 1/32* (2013.01); *C12N 9/0006* (2013.01); *C12P 7/56* (2013.01); *C12R 1/225* (2013.01); *Y02P 20/52* (2015.11)

(58) Field of Classification Search
None
See application file for complete search history.

(56) References Cited

U.S. PATENT DOCUMENTS

| 5,686,276 A | * | 11/1997 | Laffend et al. | ................. 435/158 |
| 2007/0148749 A1 | * | 6/2007 | Yasuda et al. | ................. 435/158 |

FOREIGN PATENT DOCUMENTS

| EP | 1731604 A1 | 12/2006 |
| WO | 2006007395 A1 | 1/2006 |
| WO | 2007103032 A2 | 9/2007 |
| WO | 2010122165 A1 | 10/2010 |
| WO | 2011039137 A1 | 4/2011 |

OTHER PUBLICATIONS

Drake et al., Rates of Spontaneous Mutation, Genetics (1998), vol. 148, pp. 1667-1686.*

(Continued)

*Primary Examiner* — Alexander Kim
(74) *Attorney, Agent, or Firm* — Meunier Carlin & Curfman LLC

(57) ABSTRACT

The invention refers to a method of biotransforming a carbohydrate of a raw material into a chemical, by cultivating *Lactobacillus diolivorans* in the presence of the raw material to produce a chemical substance, and isolating the chemical substance in the purified form, and the use of *L. diolivorans* in one of a series of biotransformation methods, wherein carbohydrates from at least two different carbohydrate sources of low purity are transformed into chemicals.

9 Claims, 11 Drawing Sheets

(56) References Cited

OTHER PUBLICATIONS

Figure 1:
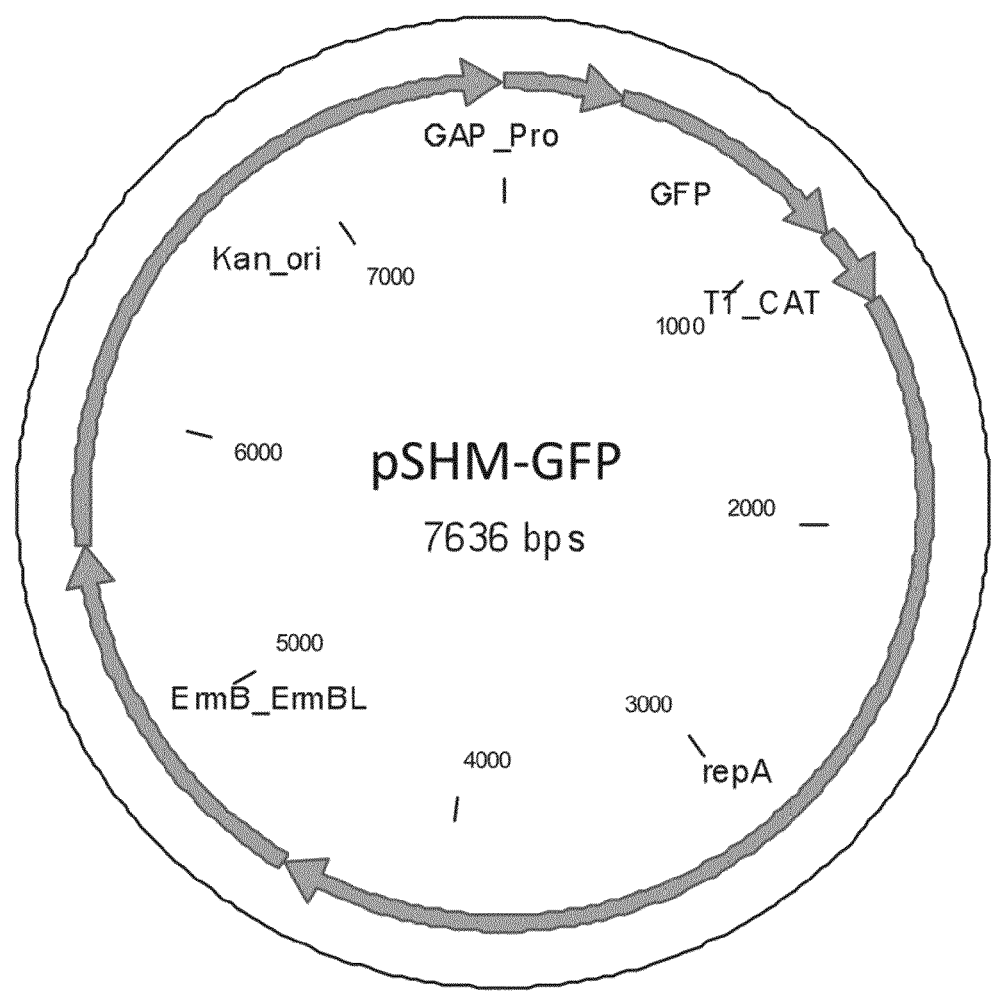

Zhang et al., Propionic acid production by cofermentation of Lactobacillus buchneri and Lactobacillus diolivorans in sourdough., Food Microbiology (May 2010), vol. 27, Issue 3 pp. 390-395.*
What-flour-contain-carbohydrate (last viewed on Jun. 18, 2015).*
This Famishing World by Alfred McCann (1918), George H. Doran Company, p. 269.*
Fugelsang et al. (2007), Springer, Wine Microbiology Practical Application and Procedure, chapter 2, pp. 29-44.*
International Search Report from related application No. PCT/EP2012/071812, issued Apr. 29, 2013.
Written Opinion of the International Search Authority from related application No. PCT/EP2012/071812, issued May 3, 2014.
European Search Report from related application No. EP 14153181, issued Jul. 8, 2014.
Gibson D. G. et al. (2009). Enzymatic assembly of DNA molecules up to several hundred kilobases. Nature Methods, 6(5), 343-345.
Hazimah, A. H., Ooi, T. L., & Salmiah, A. (2003). Recovery of glycerol and diglycerol from glycerol pitch. Journal of Oil Palm Research, 15, 1-5.
International Union of Pure and Applied Chemistry, Applied Chemistry Division, Commission on Oils, Fats and Derivatives (1980).
Standard Methods for the Analysis of Oil, Fats and Derivatives, Pure & Appl. Chem, 52, 1939-1954.
Krooneman J. et al. (2002). *Lactobacillus diolivorans* sp. nov., a 1,2-propanediol-degrading bacterium isolated from aerobically stable maize silage, International Journal of Systematic and Evolutionary Microbiology, Society for General Microbiology, 52, 639-646.
Petitdemange E. et al. (1995). Fermentation of raw glycerol to 1,3-propanediol by new strains of Clostridium butyricum, Journal of Industrial Microbiology, 15(6), 498-502.
Thompson, J. C., & He, B. B. (2006). Characterization of crude glycerol from biodiesel production from multiple feedstocks. Applied Engineering in Agriculture, 22(2), 261-265.
Werning, M. L. et al. (2006). Pediococcus parvulus gtf Gene Encoding the GTF Glycosyltransferase and Its Application for Specific PCR Detection of β-D-Glucan-Producing Bacteria in Foods and Beverages. Journal of Food Protection, 69(1), 161-169.
Willke, T., & Vorlop, K. (2008). Biotransformation of glycerol into 1, 3-propanediol. European journal of Lipid Science and Technology, 110(9), 831-840.
Office of the Texas State Chemist. Feed Industry Memorandum No. 5-22. Definition of Crude Glycerin from Biodiesel Production. Nov. 29, 2007.

\* cited by examiner

Fig. 2:

SEQ ID 1:

ACTAAGTTTTCCTCCTTTAGGAAATAGAAAATATAATTAATAGTACAGATACAATCGTACCACTAAAT
GAAAACAAAGTCAGCACCCTTGTGAACCAAGGCTCAAAGTGCGCCTCGAGTAAACATTATTTAATTA
CTCAAATTCGAGTATAGCAGACCATTTTATAAATGCAACGCCCAGAATTTAGTAAAcGTTTCCATATG
ACACTTTTTATTACACCTTGAAATGTAatCGATTTTCTAGTATATTTATATAGTAAGTTGCGCTCGTAG
TGTAATGGATCGCACGTAAGATTCCGGTTCTTGAAATGAGGGTTCGATTCCCCCCGAGCGCATTAT
TAAATGATGTTTC

Fig. 2 continued
SEQ ID 2:

GAATTAACGAGTTACGCAAAGAAGCCATTGATTACTCTACTAGAGAATCTTATGTCACGACCAAATT
ATTTTTTATCGCCAACATGATTAAACACAATACAAGATCATCTCGTGAGTTATTAAAAGCCTTAAAAG
ACGATCCCAATGTATTGGCTACAGTTCCAGAAAAGGAGCTATTCAATCGTTCAACATTGGATAAAAA
ATCTCTTTCAAAAATGGCAGAAGACCACAAAACATATATTGATCAACATGAATTTTTTGATAGTATGG
ACAAAACATTTAATGAAATCACAGAAAAACTATAAGTGTTTTGTACACGTGTTAATCATATGTATATG
CAACATATGTATATGCAACATATGTACGTGCAACACATGTACATACGTATTGTAAAGGAGGACTACC
TATGGCATTCGATCCAGAGAACAAAAATATAAAAAAGGCACTACAAAAAAATGAAACAGAACAACCA
ACTGATACTAAAGACAAACTTATTATTCCTGTTTTTAAAGATGAAGAGGAACGTACTAAGAACTATAC
CTTTTCACTTCAACCTAGCGCGCGCAAAAGGCTTGATGGTCTGGCCAAAGAACATAATTTTAAGTCT
GCCTCCAAATTTTTAAATGAGCTTATAAAAAATATGTGATGTTACTTAGAATAAGGAGGAGCATTATG
GGGATTCCAATAAATATAACATTCTTGATTGTCAGTCTTATTGTTTTCTGGATAATTCCAGTTATTGG
AATTGCAAAAAAGCGCCTGGTAGATGACCGCTTTTTTATTCGACAGTGGTTATTTCCAATGCAGTAT
TGGTTACAGCTATTCTTTGAAAGAATCAGTGGTAACCGTCGTATTGTCGTAAGAATTTTACAGATAAT
GTCCCTGTTTATCACGTATTTTTGCGGGTTACTTATGCTCATGATTTTCAGTGTTTTTGATGGGAATT
TGCTTAAACACCCCGAAGCATTTTTACTTTTCGAATATTTACTGGTAGCTTCTATCGCTTACTGGTTT
CAACCAAAAGCAGGCAAAGTATACAAGACCAAATAAAGTTGCCGCTTGGTAAGCGCTATGCTAGAC
TAAGACTAATTTAACAACCGAATAAAGAGATCAATCTAAACAGAAAAATCCCCGATTCACGAGGAAT
CAGGGATTTTGGGTTTAGCAAGTAGCTGCTAGAAAGCTACTTAGATCCAATCGATTTTAACTTGCCG
GTGAAAATCGATTGAACGTTGTTCTTAATTTGTAGGTTAATTATACCGCAAACCGGTCCAAAAGGAC
AAGTTAAGGATAGTTaAAAAACAAATTAAAGTCAATGGACTAAGTAGCTAACCGAAGCTGCCTAGTC
CATTTTTGTTTAGTTGCTATAAATTAAAAAAGTTGCCGGTTGGGCAACTCACAAACAGACACATGCT
GATGAAATTGCAAAGCCGATCACTACCAATGTTCGCTTTGTAATTCAGTTAGAGCATATCAGATTTG
TATTTTAAAGCAAATCAAATGTTTTAGCAACTCTCTTTTGAGACAGCGTGTGTCAGTCAAGAAAGGG
AGTTTTTATGATGGATCAAACAAATTTCAATTACTATGAAGCCGATAACGTATATGGAGCCCTATTTT
TCCAGTTCCCTAAGGTATTAATGTATGGCGATCAATACAAGCATTTAAGCAGTGACGCTAAATTAGC
TTATATGGTACTCAAAGATCGGCTAGAGTATTCGTTGAGAAATAACTGGGTTGATGAAGATAACCAC
GTTTACTTTATTTTTACCGTTCAAGAATTACAAGACTTATTTAATTGTGCTACTGAAAAAGCCGTTAAA
ATCAAAAAAGAATTACAAGCAGCCAATTTATTAAAACAAATCCAAATGGGATTTAATCCGAAAACTAA
AAAGAATGAACCGAATCGTTTATACCTTTCCAAACTTGATGTCAAAGCCACCGATGTCTATTTACGC
GGTGAATATGAGCCGAAAGCGCCGCAATCCCTTGCTACGAGCGGGATTTCGAAAATCGAAAGTCC
GCATGACTTCGCTGGAACCCTTGCTACGAGCGGGATTTCGAAAATCGAAAGTCCGCATGACTTCGT
TAAAGACAACCAGAAAACCCTTGCTACGAGCGGGATTTCGAAAATCGAAAGCAATCTATATAAAGAC
TTTAAAGATATAGATAACAATAGATACAATATAGATACTCAAAAGTTAGACTTTTCCACAGCCCAATT
CTCACCAGCAGAACTAGAAAAGCAAAACAAGGATTTGGTGAACCATGCTAATGATTTCTTAACTGAT
GAAGATAGTGGCTTACCCGTTTTCTTAGAACCCGAAGCCGTACAATTACTTAGTTTCTGGTGCCGCA
CCCCGCAACAAATGCGCCGGTTTATTGGTATTATCTTGAATGCTAAATATCGAGTTGAAAAGGATCA
TCAGGACATTGGCGTCATAATCCCACTTGATGATGAGGAACTGAAGCCTTTAATGACTAAAGCCTTG
AGGCGCTACTTTAACGCCCTGAGAAGTAATGAGAAGCATATCAAGAACGTTGAAAACTACTTGTAC
GGCACCATGCAAAACTTGTTTGGCATTTGGTGGAATAAACAAGCGGCTAGAGAATATGCGGCCAAA
CACCCCGAAGAAGAAAAATCGGCCGACAACGATAACAGTGGGTTGTACTACTAGTCCCAAAAGGCT
ACAAAATCCTTTCTAAGCGATTTTAAGACTTACTAACCTATTTATACTTAAGTTAGATTTAAATGGCTT
AAACAGAAGAATAGGGGCTTTTAAATGAGTGTCAGAGCTAACCAGGCTAACCAGCTCAAAAGTTCA
GCCTTTAGATCAACGCCAAGCTCAAGTGATTTGAGGCCAAGGCTTTATCTATTGATAAGGTACTCAA
AAGGTAGTATAATGGTAGTGGTAAAAGAAAGGAGATGAGACAATCATGGCAGTTAAGGAAAAGAAA
CGGGTCCAAGTCAAGATTGATAAAGATTTGGCCGATGATACCGAAGCAATTTTAAGCGAATTGGGC
TTAAATCCAACCACGGCCATTAACATGTTTTACAAGCGGATTGTTGCTAATGGTGCTTTACCTTTTAA
TGCGTCTTTAAGCGAAGAAGAAAAAGCTAATTTACGCTTTTTAAAGGCGACCGAAGGGACACCAGT
CACCGAGTTCAAAGACGCTAAAGAG

Fig. 2 continued
SEQ ID 3:

GAAACATCATTTAATAATGCGCTCGGGGGGAATCGAACCCTCATTTCAAGAACCGGAATCTTACGT
GCGATCCATTACACTACGAGCGCAACTTACTATATAAATATACTAGAAAATCGATTACATTTCAAGGT
GTAATAAAAAGTGTCATATGGAAACGTTTACTAAATTCTGGGCGTTGCATTTATAAAATGGTCTGCTA
TACTCGAATTTGAGTAATTAAATAATGTTTACTCGAGGCGCACTTTGAGCCTTGGTTCACAAGGGTG
CTGACTTTGTTTTCATTTAGTGGTACGATTGTATCTGTACTATTAATTATATTTTCTATTTCCTAAAGG
AGGAAAACTTAGTATGAGCAAAGGCGAAGAACTGTTTACCGGTGTGGTGCCGATTCTGGTGGAACT
GGATGGCGATGTGAACGGTCATAAATTTAGCGTGAGCGGCGAAGGTGAAGGCGATGCGACCTATG
GTAAACTGACCCTGAAATTTATTTGCACCACCGGCAAACTGCCGGTGCCGTGGCCGACCCTGGTG
ACCACCTTTGGTTATGGCGTGCAGTGCTTTGCGCGCTATCCGGATCACATGAAACAGCATGATTTTT
TTAAAAGCGCGATGCCGGAAGGTTATGTGCAGGAACGCACCATTTTTTTTAAAGATGATGGCAACTA
TAAAACCCGCGCGGAAGTGAAATTTGAAGGTGATACCCTGGTGAACCGCATTGAACTGAAAGGCAT
TGATTTTAAAGAAGATGGTAACATTCTGGGCCATAAACTGGAATATAACTATAACAGCCATAACGTG
TATATTATGGCGGATAAACAGAAAAACGGTATTAAAGTGAACTTTAAAATTCGCCATAACATTGAAGA
TGGCAGCGTGCAGCTGGCGGATCATTATCAGCAGAACACCCCGATTGGTGATGGCCCGGTGCTGC
TGCCGGATAACCATTATCTGAGCACCCAGAGCGCGCTGAGCAAAGATCCGAACGAAAAACGCGAT
CACATGGTGCTGCTGGAATTTGTGACCGCGGCGGGTATTACGCATGGCATGGATGAACTGTATAAA
TAATATGAGATAATGCCGACTGTACTTTTTACAGTCGGTTTTCTAATGTCACTAACCTGCCCCGTTAG
TTGAAGAAGGTTTTTATATTACAGCTCCAGATCCATATCCTTCTTTTTCTGAACCGACTTCTCCTTTTT
CGCTTCTTTATTCCAATTGCTTTATTGACGTTGAGCCTCGGAACCCTTAACAATCCCAAAACTTGTC
GAATGGTCGGCTTAATAGCTCACGCTATGCCGACGAATTAACGAGTTACGCAAAGAAGCCATTGAT
TACTCTACTAGAGAATCTTATGTCACGACCAAATTATTTTTTATCGCCAACATGATTAAACACAATAC
AAGATCATCTCGTGAGTTATTAAAAGCCTTAAAAGACGATCCCAATGTATTGGCTACAGTTCCAGAA
AAGGAGCTATTCAATCGTTCAACATTGGATAAAAAATCTCTTTCAAAAATGGCAGAAGACCACAAAA
CATATATTGATCAACATGAATTTTTTGATAGTATGGACAAAACATTTAATGAAATCACAGAAAAACTAT
AAGTGTTTTGTACACGTGTTAATCATATGTATATGCAACATATGTATATGCAACATATGTACGTGCAA
CACATGTACATACGTATTGTAAAGGAGGACTACCTATGGCATTCGATCCAGAGAACAAAAATATAAA
AAAGGCACTACAAAAAAATGAAACAGAACAACCAACTGATACTAAAGACAAACTTATTATTCCTGTTT
TTAAAGATGAAGAGGAACGTACTAAGAACTATACCTTTTCACTTCAACCTAGCGCGCGCAAAAGGCT
TGATGGTCTGGCCAAAGAACATAATTTTAAGTCTGCCTCCAAATTTTTAAATGAGCTTATAAAAAATA
TGTGATGTTACTTAGAATAAGGAGGAGCATTATGGGGATTCCAATAAATATAACATTCTTGATTGTCA
GTCTTATTGTTTTCTGGATAATTCCAGTTATTGGAATTGCAAAAAAGCGCCTGGTAGATGACCGCTT
TTTTATTCGACAGTGGTTATTTCCAATGCAGTATTGGTTACAGCTATTCTTTGAAAGAATCAGTGGTA
ACCGTCGTATTGTCGTAAGAATTTTACAGATAATGTCCCTGTTTATCACGTATTTTTGCGGGTTACTT
ATGCTCATGATTTTCAGTGTTTTTGATGGGAATTTGCTTAAACACCCCGAAGCATTTTTACTTTTCGA
ATATTTACTGGTAGCTTCTATCGCTTACTGGTTTCAACCAAAAGCAGGCAAAGTATACAAGACCAAA
TAAAGTTGCCGCTTGGTAAGCGCTATGCTAGACTAAGACTAATTTAACAACCGAATAAAGAGATCAA
TCTAAACAGAAAAATCCCCGATTCACGAGGAATCAGGGATTTTGGGTTTAGCAAGTAGCTGCTAGA
AAGCTACTTAGATCCAATCGATTTTAACTTGCCGGTGAAAATCGATTGAACGTTGTTCTTAATTTGTA
GGTTAATTATACCGCAAACCGGTCCAAAAGGACAAGTTAAGGATAGTTAAAAAACAAATTAAAGTCA
ATGGACTAAGTAGCTAACCGAAGCTGCCTAGTCCATTTTTGTTTAGTTGCTATAAATTAAAAAAGTTG
CCGGTTGGGCAACTCACAAACAGACACATGCTGATGAAATTGCAAAGCCGATCACTACCAATGTTC
GCTTTGTAATTCAGTTAGACATATCAGATTTGTATTTTAAAGCAAATCAAATGTTTTAGCAACTCTCT
TTTGAGACAGCGTGTGTCAGTCAAGAAAGGGAGTTTTTATGATGGATCAAACAAATTTCAATTACTA
TGAAGCCGATAACGTATATGGAGCCCTATTTTTCCAGTTCCCTAAGGTATTAATGTATGGCGATCAA
TACAAGCATTTAAGCAGTGACGCTAAATTAGCTTATATGGTACTCAAAGATCGGCTAGAGTATTCGT
TGAGAAATAACTGGGTTGATGAAGATAACCACGTTTACTTTATTTTTACCGTTCAAGAATTACAAGAC
TTATTTAATTGTGCTACTGAAAAGCCGTTAAAATCAAAAAGAATTACAAGCAGCCAATTTATTAAA
ACAAATCCAAATGGGATTTAATCCGAAAACTAAAAGAATGAACCGAATCGTTTATACCTTTCCAAAC
TTGATGTCAAAGCCACCGATGTCTATTTACGCGGTGAATATGAGCCGAAAGCGCCGCAATCCCTTG
CTACGAGCGGGATTTCGAAAATCGAAAGTCCGCATGACTTCGCTGGAACCCTTGCTACGAGCGGG
ATTTCGAAAATCGAAAGTCCGCATGACTTCGTTAAAGACAACCAGAAAACCCTTGCTACGAGCGGG
ATTTCGAAAATCGAAAGCAATCTATATAAAGACTTTAAAGATATAGATAACAATAGATACAATATAGA
TACTCAAAAGTTAGACTTTTCCACAGCCCAATTCTCACCAGCAGAACTAGAAAAGCAAAACAAGGAT
TTGGTGAACCATGCTAATGATTTCTTAACTGATGAAGATAGTGGCTTACCCGTTTTCTTAGAACCCG
AAGCCGTACAATTACTTAGTTTCTGGTGCCGCACCCCGCAACAAATGCGCCGGTTTATTGGTATTAT
CTTGAATGCTAAATATCGAGTTGAAAAGGATCATCAGGACATTGGCGTCATAATCCCACTTGATGAT
GAGGAACTGAAGCCTTTAATGACTAAAGCCTTGAGGCGCTACTTTAACGCCCTGAGAAGTAATGAG
AAGCATATCAAGAACGTTGAAAACTACTTGTACGGCACCATGCAAAACTTGTTTGGCATTTGGTGGA

Fig. 2 continued
SEQ ID 3 continued

```
ATAAACAAGCGGCTAGAGAATATGCGGCCAAACACCCCGAAGAAGAAAAATCGGCCGACAACGAT
AACAGTGGGTTGTACTACTAGTCCCAAAAGGCTACAAAATCCTTTCTAAGCGATTTTAAGACTTACT
AACCTATTTATACTTAAGTTAGATTTAAATGGCTTAAACAGAAGAATAGGGGCTTTTAAATGAGTGTC
AGAGCTAACCAGGCTAACCAGCTCAAAAGTTCAGCCTTTAGATCAACGCCAAGCTCAAGTGATTTG
AGGCCAAGGCTTTATCTATTGATAAGGTACTCAAAAGGTAGTATAATGGTAGTGGTAAAAGAAAGGA
GATGAGACAATCATGGCAGTTAAGGAAAAGAAACGGGTCCAAGTCAAGATTGATAAAGATTTGGCC
GATGATACCGAAGCAATTTTAAGCGAATTGGGCTTAAATCCAACCACGGCCATTAACATGTTTTACA
AGCGGATTGTTGCTAATGGTGCTTTACCTTTTAATGCGTCTTTAAGCGAAGAAGAAAAAGCTAATTT
ACGCTTTTTAAAGGCGACCGAAGGGACACCAGTCACCGAGTTCAAAGACGCTAAAGACCTTAGAAG
CAAACTTAGAGTGTGTTGATAGTGCATTATCTTAAAATTTTGTATAATAGGAATTGAAGTTAAATTAG
ATGCTAAAAATAGGAATTGAAGTTAAATTAGATGCTAAAAATTTGTAATTAAGAAGGAGGGATTCGTC
ATGTTGGTATTCCAAATGCGTAATGTAGATAAAACATCTACTGTTTTGAAACAGACTAAAAACAGTGA
TTACGCAGATAAATAAATACGTTAGATTAATTCCTACCAGTGACTAATCTTATGACTTTTTAAACAGAT
AACTAAAATTACAAACAAATCGTTTAACTTCAGGAGAGATTACATGAACAAAAATATAAAATATTCTC
AAAACTTTTTAACGAGTGAAAAAGTACTCAACCAAATAATAAAACAATTGAATTTAAAAGAAACCGAT
ACCGTTTACGAAATTGGAACAGGTAAAGGGCATTTAACGACGAAACTGGCTAAAATAAGTAAACAG
GTAACGTCTATTGAATTAGACAGTCATCTATTCAACTTATCGTCAGAAAAATTAAAACTGAATACTCG
TGTCACTTTAATTCACCAAGATATTCTACAGTTTCAATTCCCTAACAAACAGAGGTATAAAATTGTTG
GGAATATTCCTTACAATTTAAGCACACAAATTATTAAAAAAGTGGTTTTTGAAAGCCGTGCGTCTGAC
ATCTATCTGACTGTTGAAGAAGGATTCTACAAGCGTACCTTGGATATTCACCGAACACTAGGGTTGC
TCTTGCACACTCAAGTCTCGATTCAGCAATTGCTTAAGCTGCCAGCGGAATGCTTTCATCCTAAACC
AAAAGTAAACAGTGTCTTAATAAAACTTACCCGCCATACCACAGATGTTCCAGATAAATATTGGAAG
CTATATAAGTACTTTGTTTCAAAATGGGTCAATCGAGAATATCGTCAACTGTTTACTAAAAATCAGTT
TCGTCAAGCAATGAAACACGCCAAAGTAAACAATTTAAGTACCATTACTTATGAGCAAGTATTGTCTA
TTTTTAATAGTTATCTATTATTTAACGGGAGGAAATAATTCTATGAGTCGCTTTTTTAAATTTGGAAAG
TTACACGTTACTAAAGGGAATGGAGCGTAACTGTCAGACCAAGTTTACTCATATATACTTTAGATTG
ATTTAAAACTTCATTTTTAATTTAAAAGGATCTAGGTGAAGATCCTTTTTGATAATCTCATGAACAATA
AAACTGTCTGCTTACATAAACAGTAATACAAGGGGTGTTATGAGCCATATTCAACGGGAAACGTCTT
GCTCTAGGCCGCGATTAAATTCCAACATGGATGCTGATTTATATGGGTATAAATGGGCTCGCGATAA
TGTCGGGCAATCAGGTGCGACAATCTATCGATTGTATGGGAAGCCCGATGCGCCAGAGTTGTTTCT
GAAACATGGCAAAGGTAGCGTTGCCAATGATGTTACAGATGAGATGGTCAGACTAAACTGGCTGAC
GGAATTTATGCCTCTTCCGACCATCAAGCATTTTATCCGTACTCCTGATGATGCATGGTTACTCACC
ACTGCGATCCCCGGGAAAACAGCATTCCAGGTATTAGAAGAATATCCTGATTCAGGTGAAAATATTG
TTGATGCGCTGGCAGTGTTCCTGCGCCGGTTGCATTCGATTCCTGTTTGTAATTGTCCTTTTAACAG
CGATCGCGTATTTCGTCTCGCTCAGGCGCAATCACGAATGAATAACGGTTTGGTTGATGCGAGTGA
TTTTGATGACGAGCGTAATGGCTGGCCTGTTGAACAAGTCTGGAAAGAAATGCATAAACTTTTGCCA
TTCTCACCGGATTCAGTCGTCACTCATGGTGATTTCTCACTTGATAACCTTATTTTTGACGAGGGGA
AATTAATAGGTTGTATTGATGTTGGACGAGTCGGAATCGCAGACCGATACCAGGATCTTGCCATCC
TATGGAACTGCCTCGGTGAGTTTTCTCCTTCATTACAGAAACGGCTTTTTCAAAAATATGGTATTGAT
AATCCTGATATGAATAAATTGCAGTTTCATTTGATGCTCGATGAGTTTTTCTAAGAATTAATTCATGA
CCAAAATCCCTTAACGTGAGTTTTCGTTCCACTGAGCGTCAGACCCCGTAGAAAAGATCAAAGGAT
CTTCTTGAGATCCTTTTTTTCTGCGCGTAATCTGCTGCTTGCAAACAAAAAAACCACCGCTACCAGC
GGTGGTTTGTTTGCCGGATCAAGAGCTACCAACTCTTTTTCCGAAGGTAACTGGCTTCAGCAGAGC
GCAGATACCAAATACTGTCCTTCTAGTGTAGCCGTAGTTAGGCCACCACTTCAAGAACTCTGTAGCA
CCGCCTACATACCTCGCTCTGCTAATCCTGTTACCAGTGGCTGCTGCCAGTGGCGATAAGTCGTGT
CTTACCGGGTTGGACTCAAGACGATAGTTACCGGATAAGGCGCAGCGGTCGGGCTGAACGGGGG
GTTCGTGCACACAGCCCAGCTTGGAGCGAACGACCTACACCGAACTGAGATACCTACAGCGTGAG
CTATGAGAAAGCGCCACGCTTCCCGAAGGGAGAAAGGCGGACAGGTATCCGGTAAGCGGCAGGG
TCGGAACAGGAGAGCGCACGAGGGAGCTTCCAGGGGGAAACGCCTGGTATCTTTATAGTCCTGTC
GGGTTTCGCCACCTCTGACTTGAGCGTCGATTTTTGTGATGCTCGTCAGGGGGCGGAGCCTATG
GAAAAACGCCAGCAACGCGGCCTTTTTACGGTTCCTGGCCTTTTGCTGGCCTTTTGCTCACATGTT
CTTTCCTGCGTTATCCCCTGATTCTGTGGATAACCGTATTACCGCCTTTGAGTGAGCTGATACCGCT
CGCCGCAGCCGAACGACCGAGCCGCAGCGAGTCAGTGAGCGAGGAAGCGGAAGAGCGCCCAATAC
GCAAACCGCCTCTCCCCGCGCGTTGGCCGATTCATTAATGCAGCTGGCACGACAGGTTTCCCGAC
TGGAAAGCGGGCAGTGAGCGCAACGCAATTAATGTGAGTTAGCTCACTCATTAGGCACCCCAGGC
TTTACACTTTATGCTTCCGGCTCGTATGTTGTGTGGAATTGTGAGCGGATAACAATTTCACACAGGA
AACAGC
```

Fig. 2 continued
SEQ ID 4:

```
CAGGACGAACGCTGGCGGCGTGCCTAATACATGCAAGTCGAACGCGTCTTGGTCAATGATTTTAG
GTGCTTGCACTTGAATGATTTGACATTAAGACGAGTGGCGAACTGGTGAGTAACACGTGGGTAACC
TGCCCTTGAAGTAGAGGATAACACTTGGAAACAGGTGCTAATACTGCATAACAACGAAAACCGCCT
GGTTTTCGTTTGAAAGATGGCTTCGGCTATCGCTTTAGGATGGACCCGCGGCGTATTAGCTAGTTG
GTGAGGTAACGGCTCACCAAGGCAATGATACGTAGCCGACCTGAGAGGGTAATCGGCCACATTGG
GACTGAGACACGGCCCAAACTCCTACGGGAGGCAGCAGTAGGGAATCTTCCACAATGGACGAAAG
TCTGATGGAGCAACGCCGCGTGAGTGATGAAGGGTTTCGGCTCGTAAAACTCTGTTGTTGGAGAA
GAACGGGTGTCAGAGTAACTGTTGACATCGTGACGGTATCCAACCAGAAAGCCACGGCTAACTAC
GTGCCAGCAGCCGCGGTAATACGTAGGTGGCAAGCGTTGTCCGGATTTATTGGGCGTAAAGCGAG
CGCAGGCGGTTTTTTAGGTCTGATGTGAAAGCCTTCGGCTTAACCGGAGAAGTGCATCGGAAACC
GGGAGACTTGAGTGCAGAAGAGGACAGTGGAACTCCATGTGTAGCGGTGAAATGCGTAGATATAT
GGAAGAACACCAGTGGCGAAGGCGGCTGTCTGGTCTGCAACTGACGCTGAGGCTCGAAAGCATG
GGTAGCGAACAGGATTAGATACCCTGGTAGTCCATGCCGTAAACGATGAGTGCTAAGTGTTGGAG
GGTTTCCGCCCTTCAGTGCTGCAGCTAACGCATTAAGCACTCCGCCTGGGGAGTACGACCGCAAG
GTTGAAACTCAAAGGAATTGACGGGGGCCCGCACAAGCGGTGGAGCATGTGGTTTAATTCGATGC
TACGCGAAGAACCTTACCAGGTCTTGACATCTTCTGCCAACCTAAGAGATTAGGCGTTCCCTTCGG
GGACAGAATGACAGGTGGTGCATGGTTGTCGTCAGCTCGTGTCGTGAGATGTTGGGTTAAGTCCC
GCAACGAGCGCAACCCTTATTGTTAGTTGCCAGCATTTAGTTGGGCACTCTAGCAAGACTGCCGGT
GACAAACCGGAGGAAGGTGGGGATGACGTCAAATCATCATGCCCCTTATGACCTGGGCTACACAC
GTGCTACAATGGACGGTACAACGAGTCGCGAAACCGCGAGGTCAAGCTAATCTCTTAAAGCCGTTC
TCAGTTCGGATTGTAGGCTGCAACTCGCCTACATGAAGTTGGAATCGCTAGTAATCGTGGATCAGC
ATGCCACGGTGAATACGTTCCCGGGCCTTGTACACACCGCCCGTCACACCATGAGAGTTTGTAACA
CCCAAAGCCGGTGAGGTAACCTTCGGGGGCCAGCCGTCTAGGTGGGACAGATGA
```

Fig. 4 a)

GAP_Pro: (SEQ ID 29)

ACTAAGTTTTCCTCCTTTAGGAAATAGAAAATATAATTAATAGTACAGATACAATCGTACCACTAAAT
GAAAACAAAGTCAGCACCCTTGTGAACCAAGGCTCAAAGTGCGCCTCGAGTAAACATTATTTAATTA
CTCAAATTCGAGTATAGCAGACCATTTTATAAATGCAACGCCCAGAATTTAGTAAAcGTTTCCATATG
ACACTTTTTATTACACCTTGAAATGTAatCGATTTTCTAGTATATTTATATAGTAAGTTGCGCTCGTAG
TGTAATGGATCGCACGTAAGATTCCGGTTCTTGAAATGAGGGTTCGATTCCCCCCGAGCGCATTAT
TAAATGATGTTTC

PDODH(NADPH): (SEQ ID 30)

ATGGAAGAAATTCGAATTCCAACCAAAGTCTTTTCAGGAAATGATAGCTTGGACTGGCTGGAAAAAT
TGTCAAACAAGAAAATTCTGTTGGTATGTGATTCGTTTCTACCTAATACACCAACATTTGACACAATT
AAAAGCAAGGTTGAAGGAAATAACGAGGTTACGATTTTCTCCGATGTCAAACCAGACCCACCGCTG
CATAACATTATGCTGGGGGTTGAACAATTTAGTAAGGTTAAGCCCAATGTCATGATTGGTATTGGTG
GTGGTTCGGCAATTGATACCGGTAAAGCGATTCGGTTCTTTGGCGAGAAAATTGAAAAGTATGATAT
TGAACAATTTATTGCCATCCCAACAACGAGTGGAACAGGTTCCGAAGTTACTAATACCAGTGTTGTT
TCCGATCCTGAAAAGCATCAGAAGTTCCCAATCATGGAAGACTATTTAACACCGGATATTGCTTTAC
TGGATCCTCGATTGGTTATGACGGCACCTAAGAGTGTTACTGCATTCTCAGGCTTGGACGTTTTAAC
CCATTCACTGGAATCATTGGTTGCCAAAGATGCCAACACGATCACTGAAGCATTATCAGAAAAAGG
CATTGATGTCATGACCCATCTGTTGGTTGAATGTTATAAGCATGGTGACAATGAAGATGCAAGAAAG
GTCGTTCACGAAGCGTCATGTGCAGCCGGAATTGCCTTCAATAACGCTGGTTTAGGAATTTGTCATT
CACTAGCTCACCAATTAGGTGCCAACTTTCATGTTCCTCATGGCTTAGCTTGTGCCATGTTATTGCC
ACACGTTGTTTTATACAACGCTGAACATGACAAGACAGCCATGCATAAATATGCCCAGGCTTTCAAA
AAGACGGGCTTTGTTGCTCAGGGAATGGGAGATCAAATTGCCGTTCGTCGTTTAGCGGGTAAGATC
AAGCAAATGATGATCGCAATGGATTGTCCATTAACCCTGAAAGCATTTGGAATTGATCCGGCAACTG
CTGAATCAAAGACGGAAACAGTTATTGCAGATGCAAAGAAGGATGGGACATTCCCAGGAAATCCTG
TTGTGCCGTCAGATGATGACTTGCGCAACATTTACAAGAAAGTAATCCGTTAA

TT_CAT: (SE ID 31)

TATGAGATAATGCCGACTGTACTTTTTACAGTCGGTTTTCTAATGTCACTAACCTGCCCCGTTAGTT
GAAGAAGGTTTTTATATTACAGCTCCAGATCCATATCCTTCTTTTTCTGAACCGACTTCTCCTTTTTC
GCTTCTTTATTCCAATTGCTTTATTGACGTTGAGCCTCGGAACCCTTAACAATCCCAAAACTTGTCGA
ATGGTCGGCTTAATAGCTCACGCTATGCCGAC

Fig. 4 b)

repA: (SEQ ID 32)

GAATTAACGAGTTACGCAAAGAAGCCATTGATTACTCTACTAGAGAATCTTATGTCACGACCAAATT
ATTTTTTATCGCCAACATGATTAAACACAATACAAGATCATCTCGTGAGTTATTAAAAGCCTTAAAAG
ACGATCCCAATGTATTGGCTACAGTTCCAGAAAAGGAGCTATTCAATCGTTCAACATTGGATAAAAA
ATCTCTTTCAAAAATGGCAGAAGACCACAAAACATATATTGATCAACATGAATTTTTTGATAGTATGG
ACAAAACATTTAATGAAATCACAGAAAAACTATAAGTGTTTTGTACACGTGTTAATCATATGTATATG
CAACATATGTATATGCAACATATGTACGTGCAACACATGTACATACGTATTGTAAAGGAGGACTACC
TATGGCATTCGATCCAGAGAACAAAAATATAAAAAAGGCACTACAAAAAAATGAAACAGAACAACCA
ACTGATACTAAAGACAAACTTATTATTCCTGTTTTTAAAGATGAAGAGGAACGTACTAAGAACTATAC
CTTTTCACTTCAACCTAGCGCGCGCAAAAGGCTTGATGGTCTGGCCAAAGAACATAATTTTAAGTCT
GCCTCCAAATTTTTAAATGAGCTTATAAAAAATATGTGATGTTACTTAGAATAAGGAGGAGCATTATG
GGGATTCCAATAAATATAACATTCTTGATTGTCAGTCTTATTGTTTTCTGGATAATTCCAGTTATTGG
AATTGCAAAAAAGCGCCTGGTAGATGACCGCTTTTTTATTCGACAGTGGTTATTTCCAATGCAGTAT
TGGTTACAGCTATTCTTTGAAAGAATCAGTGGTAACCGTCGTATTGTCGTAAGAATTTTACAGATAAT
GTCCCTGTTTATCACGTATTTTTGCGGGTTACTTATGCTCATGATTTTCAGTGTTTTTGATGGGAATT
TGCTTAAACACCCCGAAGCATTTTTACTTTTCGAATATTTACTGGTAGCTTCTATCGCTTACTGGTTT
CAACCAAAAGCAGGCAAAGTATACAAGACCAAATAAAGTTGCCGCTTGGTAAGCGCTATGCTAGAC
TAAGACTAATTTAACAACCGAATAAAGAGATCAATCTAAACAGAAAAATCCCCGATTCACGAGGAAT
CAGGGATTTTGGGTTTAGCAAGTAGCTGCTAGAAAGCTACTTAGATCCAATCGATTTTAACTTGCCG
GTGAAAATCGATTGAACGTTGTTCTTAATTTGTAGGTTAATTATACCGCAAACCGGTCCAAAAGGAC
AAGTTAAGGATAGTTAAAAAACAAATTAAAGTCAATGGACTAAGTAGCTAACCGAAGCTGCCTAGTC
CATTTTTGTTTAGTTGCTATAAATTAAAAAAGTTGCCGGTTGGGCAACTCACAAACAGACACATGCT
GATGAAATTGCAAAGCCGATCACTACCAATGTTCGCTTTGTAATTCAGTTAGAGCATATCAGATTTG
TATTTTAAAGCAAATCAAATGTTTTAGCAACTCTCTTTTGAGACAGCGTGTGTCAGTCAAGAAAGGG
AGTTTTTATGATGGATCAAACAAATTTCAATTACTATGAAGCCGATAACGTATATGGAGCCCTATTTT
TCCAGTTCCCTAAGGTATTAATGTATGGCGATCAATACAAGCATTTAAGCAGTGACGCTAAATTAGC
TTATATGGTACTCAAAGATCGGCTAGAGTATTCGTTGAGAAATAACTGGGTTGATGAAGATAACCAC
GTTTACTTTATTTTTACCGTTCAAGAATTACAAGACTTATTTAATTGTGCTACTGAAAAAGCCGTTAAA
ATCAAAAAAGAATTACAAGCAGCCAATTTATTAAAACAAATCCAAATGGGATTTAATCCGAAAACTAA
AAAGAATGAACCGAATCGTTTATACCTTTCCAAACTTGATGTCAAAGCCACCGATGTCTATTTACGC
GGTGAATATGAGCCGAAAGCGCCGCAATCCCTTGCTACGAGCGGGATTTCGAAAATCGAAAGTCC
GCATGACTTCGCTGGAACCCTTGCTACGAGCGGGATTTCGAAAATCGAAAGTCCGCATGACTTCGT
TAAAGACAACCAGAAAACCCTTGCTACGAGCGGGATTTCGAAAATCGAAAGCAATCTATATAAAGAC
TTTAAAGATATAGATAACAATAGATACAATATAGATACTCAAAAGTTAGACTTTTCCACAGCCCAATT
CTCACCAGCAGAACTAGAAAAGCAAAACAAGGATTTGGTGAACCATGCTAATGATTTCTTAACTGAT
GAAGATAGTGGCTTACCCGTTTTCTTAGAACCCGAAGCCGTACAATTACTTAGTTTCTGGTGCCGCA
CCCCGCAACAAATGCGCCGGTTTATTGGTATTATCTTGAATGCTAAATATCGAGTTGAAAAGGATCA
TCAGGACATTGGCGTCATAATCCCACTTGATGATGAGGAACTGAAGCCTTTAATGACTAAAGCCTTG
AGGCGCTACTTTAACGCCCTGAGAAGTAATGAGAAGCATATCAAGAACGTTGAAAACTACTTGTAC
GGCACCATGCAAAACTTGTTTGGCATTTGGTGGAATAAACAAGCGGCTAGAGAATATGCGGCCAAA
CACCCCGAAGAAGAAAAATCGGCCGACAACGATAACAGTGGGTTGTACTACTAGTCCCAAAAGGCT
ACAAAATCCTTTCTAAGCGATTTTAAGACTTACTAACCTATTTATACTTAAGTTAGATTTAAATGGCTT
AAACAGAAGAATAGGGGCTTTTAAATGAGTGTCAGAGCTAACCAGGCTAACCAGCTCAAAAGTTCA
GCCTTTAGATCAACGCCAAGCTCAAGTGATTTGAGGCCAAGGCTTTATCTATTGATAAGGTACTCAA
AAGGTAGTATAATGGTAGTGGTAAAAGAAAGGAGATGAGACAATCATGGCAGTTAAGGAAAAGAAA
CGGGTCCAAGTCAAGATTGATAAAGATTTGGCCGATGATACCGAAGCAATTTTAAGCGAATTGGGC
TTAAATCCAACCACGGCCATTAACATGTTTTACAAGCGGATTGTTGCTAATGGTGCTTTACCTTTTAA
TGCGTCTTTAAGCGAAGAAGAAAAAGCTAATTTACGCTTTTTAAAGGCGACCGAAGGGACACCAGT
CACCGAGTTCAAAGACGCTAAAGA

Fig. 4 c)

ErmB_ErmBL: (SEQ ID 33)

CCTTAGAAGCAAACTTAGAGTGTGTTGATAGTGCATTATCTTAAAATTTTGTATAAT
AGGAATTGAAGTTAAATTAGATGCTAAAAATAGGAATTGAAGTTAAATTAGATGCT
AAAAATTTGTAATTAAGAAGGAGGGATTCGTCATGTTGGTATTCCAAATGCGTAAT
GTAGATAAAACATCTACTGTTTTGAAACAGACTAAAAACAGTGATTACGCAGATAA
ATAAATACGTTAGATTAATTCCTACCAGTGACTAATCTTATGACTTTTTAAACAGAT
AACTAAAATTACAAACAAATCGTTTAACTTCAGGAGAGATTACATGAACAAAAATAT
AAAATATTCTCAAAACTTTTTAACGAGTGAAAAAGTACTCAACCAAATAATAAAACA
ATTGAATTTAAAAGAAACCGATACCGTTTACGAAATTGGAACAGGTAAAGGGCATT
TAACGACGAAACTGGCTAAAATAAGTAAACAGGTAACGTCTATTGAATTAGACAGT
CATCTATTCAACTTATCGTCAGAAAAATTAAAACTGAATACTCGTGTCACTTTAATT
CACCAAGATATTCTACAGTTTCAATTCCCTAACAAACAGAGGTATAAAATTGTTGG
GAATATTCCTTACAATTTAAGCACACAAATTATTAAAAAAGTGGTTTTTGAAAGCCG
TGCGTCTGACATCTATCTGACTGTTGAAGAAGGATTCTACAAGCGTACCTTGGATA
TTCACCGAACACTAGGGTTGCTCTTGCACACTCAAGTCTCGATTCAGCAATTGCTT
AAGCTGCCAGCGGAATGCTTTCATCCTAAACCAAAAGTAAACAGTGTCTTAATAAA
ACTTACCCGCCATACCACAGATGTTCCAGATAAATATTGGAAGCTATATAAGTACT
TTGTTTCAAAATGGGTCAATCGAGAATATCGTCAACTGTTTACTAAAAATCAGTTTC
GTCAAGCAATGAAACACGCCAAAGTAAACAATTTAAGTACCATTACTTATGAGCAA
GTATTGTCTATTTTTAATAGTTATCTATTATTTAACGGGAGGAAATAATTCTATGAG
TCGCTTTTTTAAATTTGGAAAGTTACACGTTACTAAAGGGAATGGAG

Fig. 4 d)

Kan_ori: (SEQ ID 34)

```
CGTAACTGTCAGACCAAGTTTACTCATATATACTTTAGATTGATTTAAAACTTCATTTTTAATTTAAAA
GGATCTAGGTGAAGATCCTTTTTGATAATCTCATGAACAATAAAACTGTCTGCTTACATAAACAGTAA
TACAAGGGGTGTTATGAGCCATATTCAACGGGAAACGTCTTGCTCTAGGCCGCGATTAAATTCCAA
CATGGATGCTGATTTATATGGGTATAAATGGGCTCGCGATAATGTCGGGCAATCAGGTGCGACAAT
CTATCGATTGTATGGGAAGCCCGATGCGCCAGAGTTGTTTCTGAAACATGGCAAAGGTAGCGTTGC
CAATGATGTTACAGATGAGATGGTCAGACTAAACTGGCTGACGGAATTTATGCCTCTTCCGACCATC
AAGCATTTTATCCGTACTCCTGATGATGCATGGTTACTCACCACTGCGATCCCCGGGAAAACAGCA
TTCCAGGTATTAGAAGAATATCCTGATTCAGGTGAAAATATTGTTGATGCGCTGGCAGTGTTCCTGC
GCCGGTTGCATTCGATTCCTGTTTGTAATTGTCCTTTTAACAGCGATCGCGTATTTCGTCTCGCTCA
GGCGCAATCACGAATGAATAACGGTTTGGTTGATGCGAGTGATTTTGATGACGAGCGTAATGGCTG
GCCTGTTGAACAAGTCTGGAAAGAAATGCATAAACTTTTGCCATTCTCACCGGATTCAGTCGTCACT
CATGGTGATTTCTCACTTGATAACCTTATTTTTGACGAGGGGAAATTAATAGGTTGTATTGATGTTGG
ACGAGTCGGAATCGCAGACCGATACCAGGATCTTGCCATCCTATGGAACTGCCTCGGTGAGTTTTC
TCCTTCATTACAGAAACGGCTTTTTCAAAAATATGGTATTGATAATCCTGATATGAATAAATTGCAGT
TTCATTTGATGCTCGATGAGTTTTTCTAAGAATTAATTCATGACCAAAATCCCTTAACGTGAGTTTTC
GTTCCACTGAGCGTCAGACCCCGTAGAAAAGATCAAAGGATCTTCTTGAGATCCTTTTTTTCTGCGC
GTAATCTGCTGCTTGCAAACAAAAAAACCACCGCTACCAGCGGTGGTTTGTTTGCCGGATCAAGAG
CTACCAACTCTTTTTCCGAAGGTAACTGGCTTCAGCAGAGCGCAGATACCAAATACTGTCCTTCTAG
TGTAGCCGTAGTTAGGCCACCACTTCAAGAACTCTGTAGCACCGCCTACATACCTCGCTCTGCTAA
TCCTGTTACCAGTGGCTGCTGCCAGTGGCGATAAGTCGTGTCTTACCGGGTTGGACTCAAGACGAT
AGTTACCGGATAAGGCGCAGCGGTCGGGCTGAACGGGGGGTTCGTGCACACAGCCCAGCTTGGA
GCGAACGACCTACACCGAACTGAGATACCTACAGCGTGAGCTATGAGAAAGCGCCACGCTTCCCG
AAGGGAGAAAGGCGGACAGGTATCCGGTAAGCGGCAGGGTCGGAACAGGAGAGCGCACGAGGG
AGCTTCCAGGGGGAAACGCCTGGTATCTTTATAGTCCTGTCGGGTTTCGCCACCTCTGACTTGAGC
GTCGATTTTTGTGATGCTCGTCAGGGGGCGGAGCCTATGGAAAAACGCCAGCAACGCGGCCTTT
TTACGGTTCCTGGCCTTTTGCTGGCCTTTTGCTCACATGTTCTTTCCTGCGTTATCCCCTGATTCTG
TGGATAACCGTATTACCGCCTTTGAGTGAGCTGATACCGCTCGCCGCAGCCGAACGACCGAGCGC
AGCGAGTCAGTGAGCGAGGAAGCGGAAGAGCGCCCAATACGCAAACCGCCTCTCCCCGCGCGTT
GGCCGATTCATTAATGCAGCTGGCACGACAGGTTTCCCGACTGGAAAGCGGGCAGTGAGCGCAAC
GCAATTAATGTGAGTTAGCTCACTCATTAGGCACCCCAGGCTTTACACTTTATGCTTCCGGCTCGTA
TGTTGTGTGGAATTGTGAGCGGATAACAATTTCACACAGGAAACAGC
```

FERMENTATION PROCESS FOR PRODUCING CHEMICALS

The invention relates to a method of biotransforming a carbohydrate into a chemical by a fermentation process.

BACKGROUND

Chemical modification of small molecules by microorganisms is commonly known as biotransformation or biological synthesis. There are extensive biotransformation researches for production of materials that can be utilized in the industries. Microbial production of alcohols, sugars or organic acids is a promising approach for obtaining final products or building-block chemicals from renewable carbon sources, e.g. monomers for polymer synthesis. Among the most common chemicals produced by a biotransformation process there are 1,3-propanediol, citric, lactic or succinic acid, and sugar alcohols, like mannitol. The biotechnological conversion of glycerol to 1,3-propanediol is commonly achieved by bacteria under anaerobic conditions.

Willke et al. (Eur. J. Lipid Sci. Technol. 2008, 110, 831-840) review the biotransformation of glycerol into 1,3-propanediol without using fossil resources. Microbes of the species *Clostridiaceae, Enterobacteriaceae* and *Lactobacilli* were reported to be promising candidates for industrial 1,3-propanediol production.

While microbial processes for the microbiological preparation of valuable chemicals from renewable resources are known, most of the used production organisms rely on one or a few carbon sources and most of the known production organisms require a high degree of purity of the carbon sources. Thus, the carbon source is a major cost factor.

It would be desirable to employ carbon containing raw or waste materials like raw glycerol, which is a by-product from biodiesel production, in such biotransformation processes. However, impurities generally inhibit production. Efficient use of such raw material in biotransformation processes has not been achieved so far.

Consequently, there is the need for the development of new platform organisms, exhibiting high productivity of desired substances, converting a wide range of carbon sources with a low degree of purity into desirable chemicals.

*Lactobacilli* have been widely used in the food and feed industry. WO2010/122165A1 refers to a method for producing sour dough and baked goods having an extended shelf life by biological preservation through cofermenting selected Lactobacilli, for example, *L. buchneri, L. parabuchneri* and *L. diolivorans*.

*L. diolivorans sp. nov.* (DSMZ14421, LMG19667), was identified as a 1,2-propane diol degrading bacterium and isolated from aerobically stable maize silage (Krooneman et al. International Journal of Systematic and Evolutionary Microbiology 2002, 52, 639-646).

WO2006/007395A1 and WO2007/103032A2 describe bacterial additives to (sugarcane) silage employing an inoculum including *L. diolivorans*, in particular to reduce the dry matter content of the silage.

Metabolic engineering through the introduction, deletion, and modification of metabolic pathways in microorganisms by using suitable recombination techniques is widely applied for the more efficient production of desired metabolites and biomolecules. Novel substances with a broad scope of applicability in the chemical industry can be obtained e.g. from metagenomic libraries and DNA sequence based approaches.

It is the objective of the present invention to provide a biotransformation process suitable for producing chemicals using complex carbon sources, such as waste material.

SUMMARY OF THE INVENTION

The object is solved by the subject matter as claimed.

According to the invention there is provided a method of biotransforming a carbohydrate of a raw material into a chemical, herein also called chemical substance, by cultivating *Lactobacillus diolivorans* in the presence of the raw material to produce a chemical substance, and isolating the chemical substance in the purified form.

The method according to the invention specifically employs a carbohydrate that is selected from the group consisting of glycerol, sugars and sugar acids. Sugars include hexoses and pentoses. Among the preferred hexoses are glucose, mannose, galactose and rhamnose, among the preferred pentoses are xylose, arabinose and ribose. D- and L-forms of the sugars can be employed; furthermore the sugars might be derivatized such as acetylated. Among the preferred sugar acids are uronic acids such as glucuronic acid, galacturonic acid, or derivates from such acids like methylglucuronic acid.

The method according to the invention specifically employs raw material which is a complex mixture of organic carbon sources comprising the carbohydrate to be biotransformed in a purity of less than Technical Grade.

Specifically, the raw material is a complex mixture of organic carbon sources comprising an ash content of at least 0.1% (w/w), specifically at least 0.2% or at least 0.25% (w/w).

Specific embodiments of the invention refer to a raw material selected from the group consisting of raw glycerol, sugar cane, sugar beet, starchy plant, cellulose, hemicellulose, lignocellulose, including lignocellulosic plant material or lignocellulose hydrolysates, and chitin, e.g. chitin containing material derived from shell fish. Raw glycerol can be derived for example from biodiesel production or soap production. Other raw materials can be derived from the waste stream of paper, sugar or wood industries.

According to a specific aspect, the chemical is selected from the group consisting of 1,3-propanediol, 1,2-propanediol, 2-amino-1,3-propanediol, 3-hydroxy-butyrate, poly-3-hydroxybutyrate, ethanol, butanol, lactic acid, citric acid, propionic acid, 3-hydroxy propionaldehyde, 3-hydroxy propionic acid, butyric acid, valeric acid, hexanoic acid, adipic acid, succinic acid, fumaric acid, malic acid, 2,5 furan dicarboxylic acid, aspartic acid, glucaric acid, gluconic acid, glutamic acid, itaconic acid, levulinic acid, acrylic acid, propanol, isopropanol, butanol, pentanol, hexanol, heptanol, octanol, butanediol, 3-hydroxybutyrolactone, xylitol, arabinitol, sorbitol, mannitol, vitamin C, riboflavin, thiamine, tocopherol, cobalamin, pantothenic acid, biotin, pyridoxine, niacin, folic acid, 3-hydroxy propionaldehyde, 3-hydroxybutyrolactone, diamino pentane, diamino hexane and dihydroxyacetone.

Specifically, the chemical substance is an organic acid or an alcohol; exemplary chemicals produced are 1,3-propanediol, lactic acid, 3-hydroxypropionic acid, and mannitol.

According to a specific embodiment, the raw material is raw glycerol and the chemical substance is 1,3-propanediol. Specifically raw glycerol is used at a purity of less than Technical Grade Glycerol, e.g. less than 96% (w/w) and 1,3-propanediol is obtained at a purity of at least Technical Grade, e.g. at least 97% (w/w).

Such chemical may be final products, Technical Grade chemicals or chemicals of higher purity, such as USP grade chemicals, or intermediates for producing derivatives, including cell metabolites, solvents or polymers. Preferred chemicals are produced as purified chemicals by preparative separation and/or purification, preferable on a large or industrial scale. Specifically, chemicals may be produced in large amounts, called bulk material or bulk chemicals. Chemicals may also be produced for use as pharmaceutical ingredients, biocides, and specialty chemicals for technical applications Preferably, the L. diolivorans is derived from a selection of strains, including the DSM 14421 strain (Leibniz Institut DSMZ-Deutsche Sammlung von Mikroorganismen und Zellkulturen GmbH, Braunschweig, GERMANY; Genbank accession number: AF264701 (16S rRNA), e.g. AF264701.2 SEQ ID 4), identical with LMG 19667, LMG 19668 strain (LMG from BCCM/LMG Laboratorium voor Microbiologie, Universiteit Gent (UGent) Netherlands) and G77 strain (CUPV: Collección de la Universidad del Pais Vasco (Spain), Journal of Food Protection (2006) 69, 161-169) e.g. employing native cell lines or recombinant production cell lines.

According to a specific embodiment, a genetically engineered or recombinant strain of L. diolivorans is used.

Specific embodiments refer to the strain, which is subjected to mutagenesis and selected for the improved biotransformation.

According to a specific embodiment, the L. diolivorans is cultivated in a batch mode, fed-batch mode or continuous mode.

Preferably, the L. diolivorans is cultivated in a batch culture to accumulate biomass, followed by a fed-batch culture for conversion of the carbohydrate into the chemical substance.

A specific method according to the invention comprises
a) inoculating L. diolivorans into a fermentation medium with the raw material,
b) culturing the L. diolivorans in a growth medium to accumulate biomass,
c) culturing the L. diolivorans in a production medium to produce the chemical substance, and
d) isolating and purifying the chemical substance.

According to a specific embodiment, the fermentation medium may be the growth medium and/or the culturing steps b) and c) are employed in a single batch or separate batches.

Specific embodiments refer to methods, wherein
(i) 1,3-propanediol is produced from raw glycerol; or
(ii) lactic acid is produced from lignocellulose or lignocellulosic biomass hydrolysate; or
(iii) mannitol is produced from sugar beet extract or hydrolysate.

Therefore, according to one aspect, the method according to the invention refers to producing 1,3-propanediol from raw glycerol, comprising
a) inoculating L. diolivorans into a fermentation medium with the raw glycerol as the carbon source,
b) culturing the L. diolivorans in a growth medium to accumulate biomass,
c) culturing the L. diolivorans in a production medium to produce 1,3-propanediol, and
d) isolating and purifying the 1,3-propanediol.

According to a further aspect, lactic acid is produced from glucose and/or xylose derived from lignocellulose, comprising
a) inoculating L. diolivorans into a fermentation medium with the lignocellulose hydrolysate as the carbon source,
b) culturing the L. diolivorans in a growth medium to accumulate biomass,
c) culturing the L. diolivorans in a production medium to produce lactic acid, and
d) isolating and purifying the lactic acid.

According to a further aspect, mannitol is produced from fructose of sugar beet, comprising
a) inoculating L. diolivorans into a fermentation medium with the sugar beet extract as the carbon source,
b) culturing the L. diolivorans in a growth medium to accumulate biomass,
c) culturing the L. diolivorans in a production medium to produce mannitol, and
d) isolating and purifying the mannitol.

Preferably, the method according to the invention provides for the inoculation of the bacterium directly into the growth medium. Therefore, the fermentation medium is considered the growth medium.

Preferably, the method according to the invention provides for culturing steps b) and c), which are employed in a single batch or separate batches.

Typically the growth medium comprises more than one carbon source to obtain a high concentration of biomass, e.g. at least 5 g/L, preferably at least 7.5 g/L and even more preferably at least 10 g/L biomass.

Preferred carbon sources in the growth medium are selected from raw materials, e.g. selected from the group consisting of raw glycerol, hydrolysates of starchy plant material or hydrolysates of lignocellulosic plant material.

A preferred embodiment of the invention comprises a batch culture of L. diolivorans growing on the raw material, e.g. raw glycerol, or lignocellosic hydrolysates thereby accumulating the biomass, followed by feed of purified or non-purified carbon sources, e.g. containing carbohydrates, such as glycerol, optionally concomitantly with glucose and/or xylose, with a specific feed rate, thereby accumulating the chemical, e.g. 1,3-propanediol or lactic acid.

The chemical may be obtained at high concentrations. For example, the 1,3-propanediol concentration at the end of the process is preferably at least 40 g/L, more preferably at least 60 g/L, more preferably at least 80 g/L and more preferably at least 100 g/L.

The method according to the invention specifically provides for the high yield production. Specifically a chemical, such as 1,3-propanediol, is obtained with a yield of at least 50%.

In particular, the product yield based on substrate consumption, in other words the amount of product produced on a molar basis divided by the amount of substrate consumed on a molar basis, is preferably at least 50%, more preferably at least 65%, even more preferably at least 80%, and even more preferably at least 95%.

The product yield based on substrate provision, in other words the amount of product produced on a molar basis divided by the amount of substrate fed into the process on a molar basis, is preferably at least 40%, more preferably at least 55%, even more preferably at least 70%, and even more preferably at least 85%.

It is preferred that the chemical is produced as a high purity material, specifically with at least 95% purity, preferably with at least 96% purity, preferably at least 97% purity, preferably at least 98%, even more preferably with 99% purity and most preferably with 99.5% purity.

The preferred purity grade is at least Technical Grade.

Specifically preferred is the production and isolation of the chemical on a large scale, e.g. at an industrial scale. Therefore, the term "isolation" typically used according to the invention refers to the preparative separation and purification of sufficient quantities of the chemical from the fermentation system to be further used. Such preparative isolation is thus opposed to analytical determination of fermentation products, which is used for analysis purposes only.

Preferred cell lines exhibit maximum volumetric and specific productivities for producing a chemical substance, such as 1,3-propanediol, of 0.8 g/liter/h and 0.15 g/g cell mass/h, respectively. Preferred cell lines exhibit mean volumetric and specific productivities for producing a chemical substance, such as 1,3-propanediol, of 0.5 g/liter/h and 0.1 g/g cell mass/h, respectively.

According to a specific embodiment, the invention refers to the use of *L. diolivorans* in one of a series of biotransformation processes, e.g. as platform micro-organism, wherein a carbohydrate from at least two different carbohydrate sources of raw material, e.g. including different types of carbohydrates of low purity, are transformed into chemicals. The *L. diolivorans* has proven to be tolerant in growing on different raw materials, possibly utilizing a variety of carbon sources for growing and/or producing chemicals.

A specific aspect of the invention refers to the use of *L. diolivorans* for processing raw or waste material to produce an isolated fermentation product, e.g. a protein of interest (POI) or a chemical, including metabolites, such as metabolites produced by a metabolic pathway of the organism.

According to a specific aspect the invention refers to the *L. diolivorans*, which is a genetically engineered or recombinant strain, e.g. for use in the production of a recombinant POI or a metabolite, including chemical substances, preferably processing raw or waste material, such as to produce an isolated fermentation product, but also for use with conventional cultivation media.

Specifically a genetically engineered or recombinant strain of *L. diolivorans* comprises an expression construct, such as a plasmid or a vector, comprising at least one of a promoter derived from *L. diolivorans*, such as a promoter comprising the sequence of SEQ ID 1, or an origin of replication derived from *L. diolivorans*, such as an origin of replication comprising the sequence of SEQ ID 2, or functionally active variants thereof. A preferred plasmid according to the invention is characterised by the sequence of SEQ ID 3.

According to a specific aspect, the invention refers to an expression construct comprising at least one of a promoter comprising the sequence of SEQ ID 1 or an origin of replication comprising the sequence of SEQ ID 2, or functionally active variants thereof.

Such promoter or origin of replication may be used, optionally in combination with further regulatory elements, e.g. derived from *L. diolivorans*, for producing recombinants of *L. diolivorans* or other organisms.

According to a further aspect, the invention refers to a genetically engineered or recombinant strain of *L. diolivorans*, preferably a host cell overexpressing homologous sequences and/or transformed with a vector comprising heterologous sequences, which are specifically coding and/or non-coding sequences, e.g. to overexpress either homologous and/or heterologous sequences. Specifically said host cell is engineered to increase the yield of a biotransformation product.

More specifically the host cell is engineered to increase the yield of 1,3-propanediol biotransformed from raw glycerol and/or the productivity of the host cell, e.g. the specific and/or volumetric productivity.

As an example, the host cell is engineered to overexpress NADPH-dependent 1,3-propanediol oxidoreductase.

FIGURES

FIG. 1: Shuttle vector pSHM-GFP for amplification in *Escherichia coli* and subsequent transformation of *Lactobacillus diolivorans*. GFP is expressed in both organisms.

FIG. 2: Sequences as used in the Examples
SEQ ID 1: GAP_Pro, SEQ ID 2: repA, SEQ ID 3: Plasmid, SEQ ID 4: NCBI Genbank accession number AF264701.2: 16S rRNA complete sequence FIG. 3: Shuttle vector for NADPH-dependent 1,3-propanediol oxidoreductase expression in *L. diolivorans* (pSHM-PDODH(NADPH)) containing the elements listed in Table 23.

FIG. 4: Sequences as used in the Examples, elements of TABLE 23:
FIG. 4a): GAP_Pro (SEQ ID 29), PDODH(NADPH) (SEQ ID 30), TT_CAT (SE ID 31).
FIG. 4b): repA (SEQ ID 32).
FIG. 4c): ErmB_ErmBL (SEQ ID 33)
FIG. 4d): Kan_ori (SEQ ID 34)

DETAILED DESCRIPTION OF THE INVENTION

Specific terms as used throughout the specification have the following meaning.

The term "carbon source" as used herein shall mean a carbon substrate, such as used in a biotransformation process, specifically including a source carbohydrate, capable of being metabolized by host organisms or production cell lines. The term "carbohydrate" as used according to the invention is understood in the broader sense, e.g. including sugars, sugar acids, and derivatives thereof, such as polyhydroxy aldehydes or ketones conforming to the general formula $(CH_2O)_n$ and their derivatives. Specifically included are aldehydes, such as glyceraldehydes, ketones, such as dihydroxyacetone, and hydrogenated derivatives, such as glycerol. Specifically included are polyols, preferably at least three-carbon polyols, such as sorbitol, mannitol or glycerol. Particular carbohydrates used as carbon source according to the invention are selected from the group consisting of monosaccharides, oligosaccharides, polysaccharides, polyols, and derivatives thereof, in the purified form or provided in raw materials.

The term "cell line" shall refer to an established clone of a particular cell type that has acquired the ability to proliferate over a prolonged period of time. The term "host cell line" refers to a cell line as used for expressing an endogenous or recombinant gene or products of a metabolic pathway to produce polypeptides or cell metabolites mediated by such polypeptides. A "production host cell line" or "production cell line" is commonly understood to be a cell line ready-to-use for cultivation in a bioreactor to obtain the product of a production process. The applicable production cell line may produce a number of useful intermediates and products by fermenting a low molecular weight sugar produced by saccharifying the treated biomass materials. The applicable production cell line may also produce the useful intermediates and products while saccharifying the treated biomass materials by producing the necessary enzymes. For example, fermentation or other bioprocesses can produce alcohols, organic acids, hydrocarbons, hydrogen, proteins or mixtures of any of these materials.

The term "chemical" as used herein shall refer to a chemical substance or compound, in particular organic molecules, such as used in the chemical industry, pharmaceutical industry, the agricultural industry, the cosmetics industry, food and feed industry.

The compounds specifically produced according to the invention may comprise organic acids, like lactic acid, citric acid, propionic acid, 3-hydroxy propionic acid, butyric acid, valeric acid, hexanoic acid, adipic acid, succinic acid, fumaric acid, malic acid, 2,5 furan-dicarboxylic acid, aspartic acid, glucaric acid, gluconic acid, glutamic acid, itaconic acid, levulinic acid, acrylic acid, amino acids, lipids, saturated and unsaturated fatty acids, alcohols, such as ethanol, propanol, isopropanol, butanol, pentanol, hexanol, heptanol or octanol, diols, such as 1,3-propanediol, 1,2-propanediol, 2-amino-1, 3-propanediol or butanediol, carbohydrates, e.g. sugar alcohols such as xylitol, arabinitol, sorbitol, mannitol, aromatic compounds, vitamins and cofactors such as vitamin C, riboflavin, thiamine, tocopherol, cobalamin, pantothenic acid, biotin, pyridoxine, niacin, or folic acid or 3-hydroxy propionaldehyde, 3-hydroxybutyrolactone or diamino pentane, diamino hexane or dihydroxyacetone.

A chemical is generally produced by chemical processes, but may as well be produced by a fermentation process, e.g. via a biosynthetic or metabolic pathway described herein. A chemical is typically a substance produced in small or large quantities, of low or high purity, including bulk chemicals, fine chemicals, and specialty chemicals. The term includes final products, but also intermediates to produce derivatives, such as reaction products, including monomers for polymer synthesis.

The term "derivative" with respect to a microorganism strain as used herein refers to a strain that is derived from its parent strain by e.g. classical mutagenesis and selection or by directed mutagenesis. A "derivative" of a chemical substance in the context of the invention means a compound derivable from the product of the biotransformation process, e.g. by chemical, physical or biological synthesis, including polymerization, acetylation, methylation, phosphorylation.

The term "expression" or "expression system" or "expression construct" refers to nucleic acid molecules containing a desired coding sequence and control sequences in operable linkage, so that hosts transformed or transfected with these sequences are capable of producing the encoded proteins or host cell metabolites. In order to effect transformation, the expression system may be included on an expression construct, such as a plasmid or a vector; however, the relevant DNA may also be integrated into the host chromosome. Expression may refer to secreted or non-secreted expression products, including polypeptides or metabolites, such as products of metabolic pathways.

"Expression vectors" or "vectors" used herein are defined as DNA sequences that are required for the transcription of cloned recombinant nucleotide sequences, i.e. of recombinant genes and the translation of their mRNA in a suitable host organism. Such expression vectors usually comprise an origin for autonomous replication in the host cells, selectable markers (e.g. an amino acid synthesis gene or a gene conferring resistance to antibiotics such as erythromycin, chloramphenicol, zeocin, kanamycin, G418 or hygromycin), a number of restriction enzyme cleavage sites, a suitable promoter sequence and a transcription terminator, which components are operably linked together. The terms "plasmid" and "vector" as used herein include autonomously replicating nucleotide sequences as well as genome integrating nucleotide sequences.

The term "final product" as used herein refers to a chemical of controlled quality that is manufactured and optionally finished to a product ready-to-use for further manufacturing or industrial purposes or as consumer product.

The "functionally active" variant of a nucleotide sequence, including DNA, RNA sequences and genes, in particular a promoter sequence or origin of replication, as used herein means a sequence resulting from modification of a parent sequence by insertion, deletion or substitution of one or more nucleotides within the sequence or at either or both of the distal ends of the sequence, and which modification does not affect (in particular impair) the activity of this sequence, or any homologous (preferably at least 50% sequence identity) or analogous (of species other than *L. diolivorans*) sequence, which shows activity in the host cell.

A functionally active variant of a promoter according to the invention specifically is a sequence derived from SEQ ID 1, including homologous or analogous sequences, and shows transcriptional activity in the recombinant production host cell.

A functionally active variant of a replication origin according to the invention specifically is a sequence derived from SEQ ID 2, including homologous or analogous sequences, and shows replication activity in the recombinant production host cell.

The term "genetically engineered" as used herein shall refer to a recombinant organism that is used for producing a fermentation product. The organism is typically a production cell line engineered to improve a production process or to enable the production of a new product. The term is understood in contrast to the "wild-type" organism, which is typically not genetically engineered. The term "wild-type" as used within this disclosure generally means "as isolated from natural sources" such as *L. diolivorans* DSM 14421, or *L. diolivorans* LMG 19668, or *L. diolivorans* G77.

The term "homology" indicates that two or more nucleotide sequences have (to a certain degree, up to 100%) the same or conserved base pairs at a corresponding position. A homologous sequence typically has at least about 50% nucleotide sequence identity, preferably at least about 60% identity, more preferably at least about 70% identity, more preferably at least about 80% identity, more preferably at least about 90% identity, more preferably at least about 95% identity.

"Percent (%) identity" with respect to the nucleotide sequence of a gene is defined as the percentage of nucleotides in a candidate DNA sequence that is identical with the nucleotides in the DNA sequence to which the candidate sequence shall be compared, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

The term "intermediate" as used herein shall refer to a chemical substance which is formed as a product of the biotransformation process, which may be separated from the fermentation broth and further processed to form a derivative or final product.

The term "isolate" with respect to the chemical substance or fermentation product as used herein shall mean to separate or purify the substance from at least one impurity, specifically by preparative means, to obtain an isolated product.

The term "*Lactobacillus diolivorans*" or "*L. diolivorans*" as used herein shall refer to a species of *Lactobacillus* as first described by Krooneman et al 2002 (cited above), as wild-type or derivative thereof, e.g. a genetically engineered production cell line.

The term "metabolic pathway" as used herein shall refer to biochemical reactions which take place in an organism, e.g. the metabolism of a particular compound or a microbial enzyme pathway to produce metabolites, in particular small organic molecules. This refers to all biosynthetic, modification and degradation pathways of a compound in the cell.

The term "mutagenesis" as used in the context of the present invention shall refer to a recombinant construct or organism with a mutated nucleic acid, so to obtain variants thereof with at least one change in the non-coding or coding region. Mutagenesis may be through random, semi-random or site directed mutation. Typically large randomized gene libraries are produced with a high gene diversity, which may be selected according to a specifically desired genotype or phenotype.

The term "origin of replication" or "replication origin" as used herein shall refer to a particular sequence in a genome at which DNA replication is initiated. The specifically preferred replication origin of L. diolivorans comprises or consists of the sequence according to SEQ ID 2. Any such replication origin or functionally active variant thereof, may be used to engineer recombinant production host cell lines, and to produce fermentation products therefrom.

The term "overexpression" as used herein with respect to a host cell, specifically a recombinant host cell, is intended to encompass increasing the expression of a polypeptide or protein (such as enzymes used in the biotransformation process) to a level greater than the cell normally produces. It is intended that the term encompass overexpression of homologous (endogenous), as well as heterologous sequences or proteins, specifically aiming at the increase of the productivity of the cell to produce a biotransformation product, e.g. at least 1.5-fold, preferably at least 2-fold, more preferred at least 3-fold as compared to a wild-type host cell of the same type.

The term "promoter" as used herein shall refer to a particular sequence in a genome with transcriptional activity to initiate gene expression. The specifically preferred promoter of L. diolivorans comprises or consists of the sequence according to SEQ ID 1. Any such promoter or functionally active variant thereof, may be used to engineer recombinant production host cell lines, and to produce fermentation products therefrom.

According to the invention it is preferred to provide a L. diolivorans production host cell line comprising a replication origin and/or promoter sequence according to the invention operably linked to the nucleotide sequence coding for a POI or mediating the production of other fermentation products, such as metabolites. It is specifically preferred to employ an expression construct comprising such replication origin and/or promoter sequence. The procedures used to ligate the respective DNA sequences, e.g. the promoter and other regulatory sequences, and to insert them into suitable vectors containing the information necessary for integration or host replication, are well known to persons skilled in the art, e.g. described by J. Sambrook et al., "Molecular Cloning 2nd ed.", Cold Spring Harbor Laboratory Press (1989).

The term "raw glycerol" as used herein shall refer to the by-product from biodiesel production process or soap production, also called industrial glycerol, possibly used as raw material and as a carbon substrate in several biotechnological applications. It is containing glycerol (typically in the range of 40-88%, in some cases up to 95%, e.g. about 50% (w/w)) together with salts, soaps and other impurities, including water and methyl alcohol. A typical composition for raw glycerol, such as the crude glycerol stream obtained from the biodiesel production process is provided by NOVAOL S.r.I. (Milano, Italy) Raw Glycerin from Diesel-Bi® production, with following composition: glycerol 85-95% w/w, salts of organic/inorganic acids 5-10% w/w and methyl alcohol 0-1.5% w/w.

Specifically, raw glycerol is used according to the invention that is characterized by a glycerol purity of less than Technical Grade Glycerol (>97% (w/w) purity), e.g. less than 96%, specifically less than 95%, more specifically less than 94%, more specifically less than 93%, more specifically less than 92%, more specifically less than 91%, more specifically less than 90% purity (w/w).

Specifically raw glycerol is used according to the invention that is characterized by the content of impurities, such as ashes, as determined by a standard assay.

A typical standard assay is a gravimetric method for the determination of the ash content in industrial glycerines, e.g. as described in INTERNATIONAL UNION OF PURE AND APPLIED CHEMISTRY, APPLIED CHEMISTRY DIVISION, COMMISSION ON OILS, FATS AND DERIVATIVES, "STANDARD METHODS FOR THE ANALYSIS OF OILS, FATS AND DERIVATIVES", $6^{th}$ Edition, $1^{st}$ Supplement: Part 2 (1980), SECTION III. GLYCERINES, Prepared for publication by A. HAUTFENNE, Université Catholique de Louvain, Louvain-la-Neuve, Belgium.

According to this method, the test involves combustion of a test portion, ignition of the organic matter and weighing of the residue. The ash content is defined as the quantity of ash and expressed as a percentage by mass (n/m).

Ashes are commonly understood as the approximate measure of the mineral content and other inorganic matter in biomass. The raw glycerol specifically used according to the invention is characterized by the ash content of at least 0.1% (w/w), specifically at least 0.2% or at least 0.25%, more specifically at least 0.50%, more specifically at least 0.75%, more specifically at least 1%, even more specifically at least 2% (w/w).

More specifically, raw glycerol is used according to the invention that is characterized by the glycerol purity of less than Technical Grade Glycerol and the content of impurities, such as ashes, as indicated above.

In particular, raw glycerol may be used according to the invention that is obtained as waste material of bio-diesel production, e.g. from different seed oil feedstocks, including mustard, rapeseed, canola, crambe, soybean, and waste cooking oils.

Specifically, the term "raw glycerol" is herein understood as the crude glycerol as it is recovered after separation from the fuel without further processing. Still, the term also encompasses fractionated or processed crude glycerol, such as including material generally treated and refined through filtration, ion exchange, chemical additions, and fractional vacuum distillation to yield various commercial grades. According to a specific embodiment, crude glycerol is treated to neutralize the material, e.g. to obtain a pH ranging between 6 and 8, preferably about 7. Thereby an organic phase is obtained containing fatty acids and an aqueous phase is obtained containing the glycerol besides impurities. Such fractionated crude glycerol still comprises glycerol of a purity less than Technical Grade Glycerol, and specifically an undesired amount of ashes, thus is employed as raw glycerol according to the invention.

The ash content in crude glycerol is mainly sodium from catalysts used in the biodiesel production process, and typically is contained in raw glycerol (crude glycerol) within the range of 0.25 to 5.50%, in some cases up to 8%, depending on the oil source and the biodiesel production process (Thompson et al. Applied Engineering in Agriculture 2006, Vol. 22(2): 261-265).

According to a certain embodiment, the raw glycerol is treated for pasteurization or sterilization, e.g. by autoclaving the material at 121° C., for a period of 10 to 100 min, e.g. about 20 min.

The term "raw material" refers to any complex carbohydrate materials, in particular carbohydrate enriched biomass, including carbohydrate of low purity in the monomeric or polymeric form, e.g. derived from bioenergy crops, industrial crops agricultural residues, municipal waste, industrial waste, yard waste, wood, straw, chitin containing residues from shellfish. Specific examples of raw materials are raw glycerol, sugar cane, sugar beet, starchy plant, cellulose, hemicellulose, lignocellulose, or chitin.

The complex carbohydrate mixture of a raw material typically comprises at least two different organic carbon sources in significant amounts, e.g. in amounts of at least 2%, specifically at least 3%, more specifically at least 4%, more specifically at least 5%. Thus, the carbohydrate source to be biotransformed according to the invention, herein also called "fermentable carbohydrate", is contained in the complex carbohydrate mixture of the raw material with contaminating impurities.

Specifically raw material is used according to the invention that is characterized by the fermentable carbohydrate content with a purity of less than Technical Grade (>97% (w/w) purity), e.g. less than 96%, specifically less than 95%, more specifically less than 94%, more specifically less than 93%, more specifically less than 92%, more specifically less than 91%, more specifically less than 90% purity (w/w).

Specifically raw material is used according to the invention that is characterized by the content of impurities, such as ashes, as determined by a standard assay, e.g. the determination of residue left after ignition of organic matter. Ashes are commonly understood as the approximate measure of the mineral content and other inorganic matter in biomass. The raw material specifically used according to the invention is characterized by the ash content of at least 0.1% (w/w), specifically at least 0.2% or at least 0.25%, more specifically at least 0.50%, more specifically at least 0.75%, more specifically at least 1%, even more specifically at least 2% (w/w).

More specifically, raw material is used according to the invention that is characterized by the fermentable carbohydrate purity of less than Technical Grade and the content of impurities, such as ashes, as indicated above.

Specifically, the term "raw material" is herein understood as the crude material as it is recovered from various sources without further processing. Still, the term also encompasses fractionated or processed crude material, such as including material generally treated and refined through filtration, centrifugation, ion exchange, chemical additions, and distillation, such as fractional vacuum distillation to yield various commercial grades. It is preferred that raw material is treated or processed before its use according to the invention. Preferable treatment includes pasteurization, sterilization, e.g. by autoclaving, treatment with chemicals, e.g. acids or bases, such as to obtain a pH value ranging between 6 and 8, preferably about 7, or fractionation, e.g. to reduce the amount of undesired organic acids or alcohols.

Such fractionated or processed crude material still comprises the fermentable carbohydrate at a purity less than Technical Grade and an undesired amount of ashes, thus is employed as raw material according to the invention.

According to a certain embodiment, the raw material is treated for pasteurization or sterilization, e.g. by autoclaving the material at 121° C., for a period of 10 to 100 min, e.g. about 20 min.

The term "recombinant" as used herein shall mean "being prepared by or the result of genetic engineering". Thus, a "recombinant microorganism" comprises at least one "recombinant nucleic acid". A recombinant microorganism specifically comprises an expression vector or cloning vector, or it has been genetically engineered to contain a recombinant nucleic acid sequence. A "recombinant protein" is produced by expressing a respective recombinant nucleic acid in a host.

According to the invention L. diolivorans could be used for the first time in a biotransformation process to produce chemicals from a variety of carbon sources, even of low purity. Therefore, the species could be used as a production cell line, e.g. to produce products of a biotransformation process, including a recombinant production process.

As raw materials a variety of carbon sources can be employed, since strains of L. diolivorans turned out to tolerate a series of raw materials of heterogenous origin, also including carbohydrates in a complex mixture. Specifically the L. diolivorans strains turned out to readily metabolize a range of substrate sugars or polyols or other carbohydrates in the broader sense. It is therefore considered a platform organism. The specific carbon sources are carbohydrates used as a source of the biotransformation process according to the invention. A specifically preferred carbohydrate is glycerol of raw glycerol.

In the production process according to the invention a carbon source, such as the raw material, is suitably converted to a chemical.

Typically the production process comprises the steps of (i) raw material pretreatment for purification and/or sterilization, (ii) raw material fermentation for cell growth and accumulation of the chemical, (iii) isolation of the chemical, and (iv) purification of the chemical.

In particular, the production process for producing 1,3-propanediol from raw glycerol comprises the steps of (i) raw glycerol pre-treatment for purification and/or sterilization, e.g. by pH adjustment and fractionation to separate a non-aqueous phase, and/or by sterilization through autoclaving, (ii) raw glycerol fermentation for cell growth and accumulation of 1,3-propanediol, (iii) isolation of 1,3-propanediol, and (iv) purification of 1,3-propanediol.

Therefore, the invention refers to cultivating L. diolivorans in the presence of raw material, either to grow the organism in preparation of a biotransformation process, or concomitantly with a biotransformation process. Typically biomass is accumulated and the chemical produced, either consecutively or simultaneously. For growing the organism, the raw material is optionally pre-processed, e.g. to remove a lipid phase, and may be supplemented with one or more further carbon sources, such as glucose, xylose, arabinose, fructose or others.

In specific cases, more than one chemical are produced by the fermentation process in significant amounts, which chemicals may be isolated and purified. Thus, a specific embodiment of the invention referes to the production of at least two different chemicals in the purified form by biotransforming a fermentable carbohydrate of a raw material according to the invention, in particular by the same fermentation process.

Renewable resources to be converted include glycerol, preferably raw glycerol such as the by-product from biodiesel or soap production. Raw glycerol is preferably processed before use in the fermentation process, e.g. by autoclaving and separating the aqueous phase containing the glycerol, thereby reducing the content of fatty acids.

Other preferable renewable resources include sugars. Examples for sugars are hexoses such as glucose as well as pentoses such as xylose or arabinose. Possible sources for glucose could be starchy plant material or sugar cane or sugar beet in various grades of purification.

Specifically the degree of purification may be low, e.g. less than Technical Grade purity, specifically less than 96%, specifically less than 95%, more specifically less than 94%, more specifically less than 93%, more specifically less than 92%, more specifically less than 91%, more specifically less than 90% purity (w/w).

Cellulosic glucose is another preferred carbon source. A preferred source of pentoses is hemicellulosic plant material. Specifically the degree of purification of the hemicellulosic plant material may be low.

The conversion of the carbon source preferably takes place in liquid phase, preferably in an aqueous environment. The conversion of the carbon source can take place concomitantly with the growth of the microorganisms or can be independent of the growth of the microorganisms. Therefore, the chemical substance can be accumulated in the medium while the microorganisms are growing or after the microorganisms ceased growing or both.

Inoculation of the microorganism may be into a fermentation medium, which is either a medium to provide for the bacterial growth, such as the growth medium, or directly into a production medium.

Growth and/or production can suitably take place in batch mode, fed-batch mode or continuous mode. Any suitable bioreactor can be used.

A preferred embodiment of the invention includes a batch culture to provide biomass followed by a fed-batch culture for efficient conversion of the carbon source into the desired product. The carbon source used for biomass production can, but need not be identical as the carbon source for producing the chemical substance.

For example, the strain may be grown on glucose or xylose for biomass provision followed by a feed of (raw) glycerol, which is converted into 1,3-propanediol.

A growth medium allowing the accumulation of biomass typically comprises a carbon source, a nitrogen source, a source for sulphur and a source for phosphate. Typically, such a medium comprises furthermore trace elements, vitamins, amino acids. The medium may or may not contain antifoam agents.

Preferred nitrogen sources include ammonia, ammonium salts, such as $NH_4Cl$, $(NH_4)_2SO_4$, $(NH_4)_2CO_3$ nitrate salts, such as $NaNO_3$, $KNO_3$, urea, amino acids.

Preferred sulphur sources include sulphuric acid or sulphates, such as $(NH_4)_2SO_4$, $Na_2SO_4$, $NaHSO_4$, methionine, cysteine.

Preferred phosphate sources include phosphoric acid or phosphates, such as $Na_2HPO_4$, $NaH_2PO_4$, $K_2HPO_4$, $KH_2PO_4$.

Further typical medium components include yeast extract, peptone, meat extract, malt extract, corn steep liquor.

Preferably the medium is supplemented with vitamin $B_{12}$.

A typical growth medium for *L. diolivorans* comprises casein peptone (tryptic digest), meat extract, yeast extract, Tween 80, $K_2HPO_4$, Na-acetate, $(NH_4)_2H$-citrate, $MgSO_4 \times 7$ $H_2O$, $MnSO_4 \times H_2O$.

Another typical growth medium for *L. diolivorans* comprises $K_2HPO_4$, $(NH_4)_2H$-citrate, $KH_2PO_4$, sodium chloride, ascorbic acid, potassium acetate, Tween 80, $MgSO_4 \times 7$ $H_2O$, $MnSO_4 \times H_2O$, $CoSO_4 \times 7$ $H_2O$, calcium lactate, DL-alanine, DL-aminobutyric acid, Glycine, L-histidine HCl, L-lysine HCl, L-phenylalanine, L-proline, L-serine, L-threonine, L-cysteine, L-arginine, L-aspartic acid, L-asparagine, L-glutamic acid, L-isoleucine, L-leucine, L-methionine, L-tyrosine, L-tryptophan, L-valine, nicotinic acid, calcium pantothenate, cyanocobalamin, para-aminobenzoic acid, myo-inositol, pyridoxal HCl, riboflavin, biotin, folic acid, and $FeSO_4 \times 7$ $H_2O$.

A typical production medium comprises the source chemical for biotransformation, and besides a sugar and optionally vitamins.

The feed to the fermentation typically is a carbohydrate solution with up to 50 wt %. The feed rate will limit the effects of product inhibition on the cell growth, thus a high product yield based on substrate provision will be possible.

The fermentation preferably is carried out in a slightly acidic medium, e.g. of pH 5.5-6.0, preferably at a pH of about 5.7 ("about" is understood as +/−0.1), and under anoxic conditions, e.g. by gassing with nitrogen.

Typical fermentation times are about 24 to 96 hours with temperatures in the range of 26° C. to 40° C., preferably about 30° C. ("about" is specifically understood as +/−1°).

The industrial process scale would preferably employ volumina of at least 50 L, preferably at least 1 $m^3$, more preferably at least 10 $m^3$, most preferably at least 100 $m^3$.

The production cell line is specifically used on a large scale or industrial scale.

Production conditions in industrial scale refer to e.g. fed batch cultivation in reactor volumes of 100 L to 10 $m^3$ or larger, employing typical process times of several days, or continuous processes in fermenter volumes of appr. 50-1000 L or larger, with dilution rates of appr. 0.05-0.15 $n^{-1}$.

The suitable cultivation techniques may encompass cultivation in a bioreactor starting with a batch phase, followed by a short exponential fed batch phase at high specific growth rate, further followed by a fed batch phase at a low specific growth rate. Another suitable cultivation technique may encompass a batch phase followed by a continuous cultivation phase at a low dilution rate.

Specifically the *L. diolivorans* strain may be employed as homofermentative, where the end-product is mostly one chemcial substance, such as lactic acid or lactate, or else heterofermentative, where some other products of metabolic pathways are produced. Genetically engineered variants of *L. diolivorans* may comprise metabolic pathways, which are not naturally present in *L. diolivorans*.

Applicable metabolic pathways mediating the biotransformation or metabolism of a carbon source, such as glycerol, a hexose, such as glucose, fructose, galactose, or a pentose, such as xylose or arabinose in *L. diolivorans* under anaerobic and microaerobic conditions, provide for effective conversion of the source carbon or source carbohydrate into the chemical. The chemical substance so produced may be a typical negligible product of the metabolic pathway in wild-type strains. A homofermentative route may be engineered by overexpressing pathways involved in the conversion of the source carbohydrate to the desired chemical substance, and/ or blocking those leading to the synthesis of competing by-products.

For example, the overexpression of specific enzymes involved are 1,3-propanediol oxidoreductase, glycerol kinase, glycerol-3-phosphate dehydrogenase, glycerol dehydrogenase, dihydroxyacetone kinase and triosephosphate isomerase. Further, the synthesis of by-products, such as succinate, acetate, and ethanol may be minimized by knock-out, deletion or knock-down of the respective genes.

Specific examples relate to the fermentation of glucose and glycerol into 1,3-propanediol with the wild-type *L. diolivorans* in a fed-batch process, e.g. where the biomass is accumulated upon growing on glucose, and fermentation is started upon feeding with glycerol.

A further specific example refers to fermentation of the wild-type *L. diolivorans* with xylose and glycerol into 1,3- propanediol, e.g. with xylose as batch medium for growing biomass, and glycerol as feed medium to start the biotransformation process.

According to a specific further example, the wild-type *L. diolivorans* is cultivated with glucose and raw glycerol in a batch process, employing both, glucose and raw glycerol, in the batch medium to grow biomass and to effect biotransformation of glycerol into 1,3-propanediol.

A further example refers to the cultivation of wild-type *L. diolivorans* with glucose in a batch process, to grow biomass and to effect biotransformation of glucose into lactic acid.

Yet, a further example refers to the cultivation of wild-type *L. diolivorans* with xylose in a batch process, to grow biomass and to effect biotransformation of xylose into lactic acid.

It was further shown that wild-type *L. diolivorans* could be fermented with arabinose in a batch process, to grow biomass and to effect biotransformation of arabinose into lactic acid.

According to a further example, wild-type *L. diolivorans* was fermented with fructose in a batch process, to grow biomass and to effect biotransformation of fructose into mannitol.

According to a further example, a recombinant strain of *L. diolivorans* is produced employing an expression construct such as a plasmid with the sequence of SEQ ID 3, e.g. comprising endogenous genetic elements, including a promoter of the *Lactobacillus diolivorans* gene for the glyceraldehyde-3-phosphate dehydrogenase and an origin of replication isolated from the endogenous plasmid from *Lactobacillus diolivorans*. Such recombinant strain was used as production host cell line to produce a POI.

A specific example refers to the recombinant *L. diolivorans* LMG 19668, that is engineered to overexpress the 1,3-propanediol oxidoreductase. Thereby the yield of biotransformation could be increased.

According to further examples, wild-type *L. diolivorans* was fermented with glucose and raw glycerol from various sources in a Fedbatch process, to grow biomass and to effect biotransformation of raw glycerol into 1,3-propanediol.

Preferred strains of *L. diolivorans* include DSM 14421, LMG 19668 and G77. The strains exemplary used herein were DSM 14421 and LMG 19668.

*L. diolivorans* as used by this invention is, for example, the wild-type strain, e.g. *L. diolivorans* DSM 14421 or LMG 19668, e.g. see accession number AF264701 (NCBI database) or a derivative thereof, e.g. a homologous variant or a recombinant organism, e.g. genetically engineered for the improved production of a chemical that is naturally produced by a wild-type strain, or the production of a new product of biotransformation, e.g. as a result of mutagenesis, e.g. by a variant or new metabolic pathway.

According to a specific embodiment of the present invention the strain of *L. diolivorans* has been subjected to mutagenesis and/or selection procedures, e.g. to obtain a strain with improved productivity, improved substrate range, improved product or substrate tolerance or improved product range.

Preferred methods for mutagenesis include contacting *L. diolivorans* with mutagenizing substances such as nitrosoguanidine (NTG), 5-bromo-deoxyuridine (5BU), ethyl methane sulfonate (EMS), methyl methane sulfonate (MMS), or diethylsulfate (DES). Another preferred method for mutagenesis includes UV irradiation of a culture of *L. diolivorans*.

Preferred methods for selection include plating of bacterial cultures on agar plates exhibiting the selective pressure of choice. For example, selection might be plating of the bacterial cultures on agar plates comprising an increasing amount of product or substrate impurities for selection of strains exhibiting increased tolerance to the product or substrate impurities. Another preferred method for selection of desired bacterial strains includes sorting procedures by flow cytometry.

According to a specific aspect of the present invention the strain of *L. diolivorans* is genetically engineered, such as that the natural genetic setup of the organism has been changed. This includes for example:

Deletion or inactivation or attenuation of genes naturally present in the organism
Overexpression of genes naturally present in the organism
Mutation of genes naturally present in the organism
Addition or expression of genes naturally not present in the organism
Or any combinations therefrom Specific genetically engineering of *L. diolivorans* comprises:

The provision of a recombinant DNA fragment, and/or
Transformation of the organism with said DNA fragment In general, the recombinant nucleic acids or organisms as referred to herein may be produced by recombination techniques well known to a person skilled in the art. In accordance with the present invention there may be employed conventional molecular biology, microbiology, and recombinant DNA techniques within the skill of the art. Such techniques are explained fully in the literature. See, e.g., Maniatis, Fritsch & Sambrook, Molecular Cloning: A Laboratory Manual (1982).

Examples for DNA fragments for genetic engineering of *L. diolivorans* include plasmids, linear DNA fragments, such as PCR products, and others well-known in the art. A specific plasmid comprises the replication origin of the native *L. diolivorans* plasmid, native promoters, selectable markers and expression cassettes for the genes of interest. The nucleotide sequences that could be used for engineering the cell line as used according to the invention, which would provide for an improved biotransformation process, can be obtained from a variety of sources. The origin of a promoter is preferably from genomic DNA of *L. diolivorans* DSM 14421, LMG 19668 or G77.

The promoter may be any suitable DNA sequence which shows transcriptional activity in the host cell and may be derived from genes encoding proteins either homologous or heterologous to the host. The promoter is preferably derived from a gene encoding a protein homologous to the host cell. The promoter can be an endogenous promoter or heterologous to the host cell.

Suitable promoter sequences for use with prokaryotic host cells may include but are not limited to promoters obtained from *Lactobacillus* sp., *Lactococcus* sp., *Staphylococcus* sp., *Pediococcus* sp., *Enterobacteria* sp., *Streptococcus* sp. *Oenococcus* sp. The promoter is not limited to any particular species provided that they can function in prokaryotic host cells and in particular in *Lactobacilli*.

Further suitable promoter sequences for use with bacterial host cells may include but are not limited to promoters obtained from genes that code for metabolic enzymes which are known to be present at high concentration in the cell, e.g. glycolytic enzymes like glyceraldehyde-3-phosphate dehydrogenase, triosephosphate isomerase, phosphofructokinase, enolase.

In a preferred expression system the promoter is an inducible or a constitutive promoter.

Appropriate expression vectors typically comprise regulatory sequences suitable for expression of DNA encoding a heterologous polypeptide or protein in a prokaryotic host cell.

Examples of regulatory sequences include promoters, operators, and enhancers, ribosomal binding sites, and sequences that control transcription and translation initiation and termination. The regulatory sequences may be operably linked to the DNA sequence to be expressed. For example, a promoter sequence is said to be operably linked to a coding sequence, if the promotor controls the transcription of the coding sequence.

The preferred method according to the invention employs a plasmid, which is pSHM. Expression vectors may include but are not limited to cloning vectors, modified cloning vectors and specifically designed plasmids. The preferred expression vector as used in the invention may be any expression vector suitable for expression of a recombinant gene in a host cell and is selected depending on the host organism. The recombinant expression vector may be any vector which is capable of replicating in or integrating into the genome of the host organisms, also called host vector.

In the present invention, it is preferred to use plasmids derived from L. diolivorans as the vector.

To allow expression of a recombinant nucleotide sequence in a host cell, the expression vector may provide the recombinant nucleotide sequence with a functional promoter adjacent to the 5' end of the coding sequence. The transcription is thereby regulated and initiated by this promoter sequence.

According to a preferred embodiment of the present invention, a recombinant construct is obtained by ligating the relevant genes into a vector. These genes can be stably integrated into the host cell genome or replicated as an episomal plasmid. The vector may be transferred into the host cell by transformation. Preferred methods of transformation for the uptake of the recombinant DNA fragment by the microorganism include chemical transformation, electroporation or transformation by protoplastation. Transformants according to the present invention can be obtained by introducing such a vector DNA, e.g. plasmid DNA, into a host and selecting transformants which express the relevant protein or host cell metabolite with high yields.

The polypeptides encoded by the genes can be produced using the recombinant host cell line by culturing a transformant, thus obtained in an appropriate medium, isolating the expressed product or metabolite from the culture, and optionally purifying it by a suitable method.

Several different approaches for the production of the chemical substance according to the invention are preferred. Substances may be expressed, processed and optionally secreted by transforming the bacterial organism with an expression vector harboring recombinant DNA encoding a relevant protein and at least one of the regulatory elements as described above, preparing a culture of the transformed organism, growing the culture and fermenting the carbohydrate source to recover the product of the biotransformation process.

The preferred host cell line according to the invention maintains the genetic properties employed according to the invention, and the production level remains high, e.g. at least at a µg level, even after about 20 generations of cultivation, preferably at least 30 generations, more preferably at least 40 generations, most preferred of at least 50 generations. The stable recombinant host cell is considered a great advantage when used for industrial scale production.

The chemical substance produced according to the invention typically can be isolated and purified using state of the art techniques, including the increase of the concentration of the desired chemical and/or the decrease of the concentration of at least one impurity.

As isolation and purification methods the following are preferred, specifically for preparative isolation: distillation, chromatography, crystallization, filtration, centrifugation, decanting, reprecipitation. The chemical substance may e.g. be obtained from the fermented broth that is clarified using a centrifuge.

The highly purified product is essentially free from contaminating proteins, and preferably has a purity of at least 90%, more preferred at least 95%, or even at least 98%, up to about 100%. The purified products may be obtained by purification of the cell culture supernatant or else from cellular debris.

The isolated and purified chemical substance can be identified by conventional methods such as HPLC, GC, MS, NMR, infrared spectroscopy.

The foregoing description will be more fully understood with reference to the following examples. Such examples are, however, merely representative of methods of practicing one or more embodiments of the present invention and should not be read as limiting the scope of the invention.

EXAMPLES

Example 1

Preparation of MRS-medium used for the Cultivation of *Lactobacillus diolivorans*

TABLE 1

| MRS Medium | |
|---|---|
| Component | Concentration [g/L] |
| Casein peptone, tryptic digest | 10 |
| Meat extract | 10 |
| Yeast extract | 5 |
| Tween 80 | 1 |
| $K_2HPO_4$ | 2 |
| Na-acetate | 5 |
| $(NH_4)_2H$-citrate | 2 |
| $MgSO_4 \times 7 H_2O$ | 0.20 |
| $MnSO_4 \times H_2O$ | 0.05 |
| Dissolve in $H_2O$ | |

In case of bioreactor experiments the substrates glucose/xylose/arabinose and where used glycerol were added to the medium and the pH-value was adjusted to 5.7 with concentrated hydrochloric acid (HCl). Then the medium was sterile filtered.

In case of test glass experiments the pH-value of the medium without substrate was adjusted to 5.7 with concentrated hydrochloric acid (HCl) and autoclaved at 121 ° C. for 20 min. An autoclaved 200 g/L solution of the used substrate was added separately.

Example 2

Preparation of Defined Medium 1 (DM1) used for the Cultivation of *Lactobacillus diolivorans*

TABLE 2

| Defined medium 1: | |
|---|---|
| Component | Concentration [g/L] |
| $K_2HPO_4$ | 3.1 |
| $(NH_4)_2H$-citrate | 2 |

TABLE 2-continued

Defined medium 1:

| Component | Concentration [g/L] |
|---|---|
| KH$_2$PO$_4$ | 1.5 |
| Sodium chloride | 0.02 |
| Ascorbic acid | 0.5 |
| Potassium acetate | 10 |
| Tween 80 | 1 |
| MgSO$_4$ × 7 H$_2$O | 0.50 |
| MnSO$_4$ × H$_2$O | 0.02 |
| CoSO$_4$ × 7 H$_2$O | 0.91 |
| Calcium lactate | 1 |
| DL-alanine | 0.2 |
| DL-aminobutyric acid | 0.1 |
| Glycine | 0.2 |
| L-histidine HCl | 0.2 |
| L-lysine HCl | 0.2 |
| L-phenylalanine | 0.1 |
| L-proline | 0.2 |
| L-serine | 0.1 |
| L-threonine | 0.1 |
| L-cysteine | 0.1 |
| L-arginine | 0.2 |
| L-aspartic acid | 0.3 |
| L-asparagine | 0.1 |
| L-glutamic acid | 0.3 |
| L-isoleucine | 0.1 |
| L-leucine | 0.2 |
| L-methionine | 0.1 |
| L-tyrosine | 0.1 |

TABLE 2-continued

Defined medium 1:

| Component | Concentration [g/L] |
|---|---|
| L-tryptophan | 0.1 |
| L-valine | 0.1 |
| Nicotinic acid | 10 mg |
| Calcium pantothenate | 10 mg |
| Cyanocobalamin | 0.02 mg |
| Para-aminobenzoic acid | 0.2 mg |
| Myo-inositol | 10 mg |
| Pyridoxal HCl | 10 mg |
| Riboflavin | 10 mg |
| Biotin | 1 mg |
| Folic acid | 0.2 mg |
| FeSO$_4$ × 7 H$_2$O | 0.02 |
| Dissolve in H$_2$O | |

After preparation of the medium the pH-value was adjusted to 5.7 with concentrated hydrochloric acid (HCl) and the medium was sterile filtered. Autoclaved solutions of glucose (500 g/L) and raw glycerol (850 g/L, BioDiesel Vienna GmbH, Austria; purity less than Technical Grade) were added separately.

Example 3

Co-fermentation of Glucose and Glycerol into 1,3-propanediol with Lactobacillus diolivorans DSM 14421.

Co-fermentation of glucose and glycerol for the conversion of glycerol to 1,3-propanediol (1,3-PD) using Lactobacillus diolivorans DSM 14421 is given in Table 3. The fermentation was carried out as fed-batch process using MRS-medium supplemented with 25.6 g/L glucose and 8.6 g/L glycerol as batch medium (see example 1) and a glucose/glycerol solution (0.1 mol glucose/1 mol glycerol), with a glycerol concentration of 446.7 g/L, as feed medium. The feed was started after glucose and glycerol were consumed from the batch culture medium (t=40 h). A rate of 1.5 mL/h was used to add the feed medium to the culture until the end of the process (t=161.3 h). The pH-value was adjusted to 5.7 with 8 M Potassium hydroxide (KOH) throughout the whole process. Nitrogen (N$_2$) was used for gassing (2 L/h) during the fermentation.

The yield of 1,3-propanediol was 59 wt % (g 1,3-propanediol/g glycerol total), 40 wt % (g 1,3-propanediol/g substrate total) and a titer of 63.9 g/L 1,3-propanediol was obtained.

TABLE 3

Conversion of glycerol to 1,3-propanediol (1,3-PD) using *Lactobacillus diolivorans* DSM 14421 in a fed-batch process co-fermenting glucose and glycerol

| Time [h] | OD$_{600}$ [AU] | glucose [g/L] | glycerol [g/L] | 1,3-PD [g/L] | lactic acid [g/L] | acetic acid [g/L] | ethanol [g/L] |
|---|---|---|---|---|---|---|---|
| 0.1 | 0.1 | 25.6 | 8.6 | 0.0 | 0.1 | 0.0 | 0.0 |
| 161.3 | 23.5 | 0.0 | 34.0 | 63.9 | 1.0 | 25.4 | 2.3 |

Example 4

Enhanced Co-fermentation of Glucose and Glycerol into 1,3-propanediol with *Lactobacillus diolivorans* DSM 14421 by Addition of Vitamin B$_{12}$ Co-fermentation of glucose and glycerol for the conversion of glycerol to 1,3-propanediol (1,3-PD) using *Lactobacillus diolivorans* DSM 14421 is given in Table 4. The fermentation was carried out as fed-batch process using MRS-medium supplemented with 30.4 g/L glucose, 10.3 g/L glycerol, and 5 mg/L Vitamin B$_{12}$ as batch medium (see example 1) and a glucose/glycerol solution (0.1 mol glucose/1 mol glycerol) supplemented with 5 mg/L Vitamin B$_{12}$, with a glycerol concentration of 502.5 g/L, as feed medium. The feed was started after glucose and glycerol were consumed from the culture medium (t=20 h). A rate of 1.5 mL/h was used to add the feed medium to the culture until the end of the process (t=305 h). The pH-value was adjusted to 5.7 with 8 M Potassium hydroxide (KOH) throughout the whole process. Nitrogen (N$_2$) was used for gassing (2 L/h) during the fermentation.

The yield of 1,3-propanediol was 39 wt % (g 1,3-propanediol/g glycerol total), 30 wt % (g 1,3-propanediol/g substrate total) and a titer of 92.3 g/L 1,3-propanediol was obtained.

TABLE 4

Conversion of glycerol to 1,3-propanediol (1,3-PD) using *Lactobacillus diolivorans* DSM 14421 in a fed-batch process co-fermenting glucose and glycerol

| Time [h] | OD$_{600}$ [AU] | glucose [g/L] | glycerol [g/L] | 1,3-PD [g/L] | lactic acid [g/L] | acetic acid [g/L] | ethanol [g/L] |
|---|---|---|---|---|---|---|---|
| 0.0 | 0.1 | 30.4 | 10.3 | 0.6 | 0.0 | 0.0 | 0.1 |
| 305 | 18.5 | 0.2 | 61.7 | 92.3 | 31.3 | 33.0 | 0.0 |

Example 5

Fermentation of Glucose and Glycerol into 1,3-propanediol with *Lactobacillus diolivorans* DSM 14421

Fermentation of glucose and glycerol for the conversion of glycerol to 1,3-propanediol (1,3-PD) using *Lactobacillus diolivorans* DSM 14421 is given in Table 5. The fermentation was carried out as fed-batch process using a double concentrated MRS-medium supplemented with 59.5 g/L glucose as batch medium (see example 1) and a glycerol solution with a concentration of 488.5 g/L as feed medium. The feed was started after glucose was consumed from the culture medium (t=~30 h). A rate of 1.3 mL/h was used to add the feed medium to the culture until the end of the process (t=165 h). The pH-value was adjusted to 5.7 with 8 M Potassium hydroxide (KOH) throughout the whole process. Nitrogen (N$_2$) was used for gassing (2 L/h) during the fermentation.

The yield of 1,3-propanediol was 57 wt % (g 1,3-propanediol/g glycerol total), 37 wt % (g 1,3-propanediol/g substrate total) and a titer of 54.0 g/L 1,3-propanediol was obtained.

TABLE 5

Conversion of glycerol to 1,3-propanediol (1,3-PD) using *Lactobacillus diolivorans* DSM 14421 in a fed-batch process fermenting glucose and glycerol

| Time [h] | OD$_{600}$ [AU] | glucose [g/L] | glycerol [g/L] | 1,3-PD [g/L] | lactic acid [g/L] | acetic acid [g/L] | ethanol [g/L] |
|---|---|---|---|---|---|---|---|
| 0.1 | 0.1 | 59.5 | 0.1 | 1.3 | 0.2 | 1.0 | 0.2 |
| 165.0 | 30.7 | 0.0 | 28.7 | 54.0 | 5.1 | 21.9 | 6.8 |

Example 6

Fermentation of Xylose and Glycerol into 1,3-propanediol with *Lactobacillus diolivorans* DSM 14421

Fermentation of xylose and glycerol for the conversion of glycerol to 1,3-propanediol (1,3-PD) using *Lactobacillus diolivorans* DSM 14421 is given in Table 6. The fermentation was carried out as fed-batch process using a double concentrated MRS-medium supplemented with 60.8 g/L xylose as batch medium (see example 1) and a glycerol solution with a concentration of 452.7 g/L as feed medium. The feed was started after xylose was consumed from the culture medium (t=~30 h). A rate of 1.3 mL/h was used to add the feed medium to the culture until the end of the process (t=143.4 h). The pH-value was adjusted to 5.7 with 8 M Potassium hydroxide (KOH) throughout the whole process. Nitrogen (N$_2$) was used for gassing (2 L/h) during the fermentation.

The yield of 1,3-propanediol was 33 wt % (g 1,3-propanediol/g glycerol total), 20 wt % (g 1,3-propanediol/g substrate total) and a titer of 26.7 g/L 1,3-propanediol was obtained.

TABLE 6

Conversion of glycerol to 1,3-propanediol (1,3-PD) using *Lactobacillus diolivorans* DSM 14421 in a fed-batch process fermenting xylose and glycerol

| Time [h] | OD$_{600}$ [AU] | xylose [g/L] | glycerol [g/L] | 1,3-PD [g/L] | lactic acid [g/L] | acetic acid [g/L] | ethanol [g/L] |
|---|---|---|---|---|---|---|---|
| 0.1 | 0.1 | 60.8 | 0.0 | 1.3 | 0.2 | 1.0 | 0.1 |
| 143.4 | 34.0 | 0.0 | 46.6 | 26.7 | 9.5 | 29.3 | 1.1 |

Example 7

Fermentation of Glucose and raw Glycerol into 1,3-propanediol with *Lactobacillus diolivorans* DSM 14421

Fermentation of glucose and raw glycerol for the conversion of glycerol to 1,3-propanediol (1,3-PD) using *Lactobacillus diolivorans* DSM 14421 is given in Table 8. The fermentation was carried out as batch process using DM1-medium with tripled concentrations of all amino acids and vitamins supplemented with 37.6 g/L glucose and 36.8 g/L raw glycerol (BioDiesel Vienna GmbH, Austria; purity less than Technical Grade) as batch medium (see example 2). Raw glycerol was obtained as follows: the pH-value of the crude suspension from the biodiesel production process containing the glycerol was adjusted to 7 and autoclaved for 20 min at 121° C. From here a two phase system was obtained, one organic phase containing the fatty acids and one watery phase containing the glycerol. After removing the organic phase the watery phase was autoclaved again and then used as a stock solution for addition to the culture medium.

The pH-value was adjusted to 5.7 with 8 M Potassium hydroxide (KOH) throughout the whole process. Nitrogen ($N_2$) was used for gassing (2 L/h) during the fermentation.

The yield of 1,3-propanediol was 51 wt % (g 1,3-propanediol/g glycerol total), 25 wt % (g 1,3-propanediol/g substrate total) and a titer of 54.0 g/L 1,3-propanediol was obtained.

TABLE 7

Conversion of glycerol to 1,3-propanediol (1,3-PD) using *Lactobacillus diolivorans* DSM 14421 in a fed-batch process fermenting glucose and raw glycerol

| Time [h] | $OD_{600}$ [AU] | glucose [g/L] | glycerol [g/L] | 1,3-PD [g/L] | lactic acid [g/L] | acetic acid [g/L] | ethanol [g/L] |
|---|---|---|---|---|---|---|---|
| 0.03 | 0.1 | 37.6 | 36.8 | 0.0 | 0.0 | 0.0 | 0.0 |
| 183.9 | 15.3 | 3.6 | 4.6 | 23.9 | 12.5 | 9.0 | 1.0 |

Example 8

Fermentation of Glucose into Lactic acid with *Lactobacillus diolivorans* DSM 14421

Fermentation of glucose for the conversion into lactic acid using *Lactobacillus diolivorans* DSM 14421 is given in Table 8. The fermentation was carried out as batch process using double concentrated MRS-medium supplemented with 59.5 g/L glucose as batch medium (see example 1). The pH-value was adjusted to 5.7 with 8 M Potassium hydroxide (KOH) throughout the whole process. Nitrogen ($N_2$) was used for gassing (2 L/h) during the fermentation.

The yield of lactic acid was 46 wt % (g lactic acid/g glucose total) and a titer of 28.0 g/L lactic acid was obtained.

TABLE 8

Conversion of glucose to lactic acid using *Lactobacillus diolivorans* DSM 14421 in a batch process

| Time [h] | $OD_{600}$ [AU] | glucose [g/L] | lactic acid [g/L] | acetic acid [g/L] | ethanol [g/L] |
|---|---|---|---|---|---|
| 0.1 | 0.1 | 59.5 | 0.2 | 1.0 | 0.2 |
| 41.9 | 31.3 | 0.0 | 28.0 | 1.3 | 15.5 |

Example 9

Fermentation of Xylose into Lactic acid with *Lactobacillus diolivorans* DSM 14421.

Fermentation of xylose for the conversion into lactic acid using *Lactobacillus diolivorans* DSM 14421 is given in Table 9. The fermentation was carried out as batch process using double concentrated MRS-medium supplemented with 60.8 g/L xylose as batch medium (see example 1). The pH-value was adjusted to 5.7 with 8 M Potassium hydroxide (KOH) throughout the whole process. Nitrogen ($N_2$) was used for gassing (2 L/h) during the fermentation.

The yield of lactic acid was 47 wt % (g lactic acid/g xylose total) and a titer of 27.2 g/L lactic acid was obtained.

TABLE 9

Conversion of xylose to lactic acid using *Lactobacillus diolivorans* DSM 14421 in a batch process

| Time [h] | $OD_{600}$ [AU] | xylose [g/L] | lactic acid [g/L] | acetic acid [g/L] | ethanol [g/L] |
|---|---|---|---|---|---|
| 0.1 | 0.1 | 60.8 | 0.2 | 1.0 | 0.1 |
| 41.9 | 41.3 | 0.4 | 27.2 | 24.8 | 0.7 |

Example 10

Fermentation of Arabinose into Lactic acid with *Lactobacillus diolivorans* DSM 14421

Fermentation of arabinose for the conversion into lactic acid using *Lactobacillus diolivorans* DSM 14421 is given in Table 10. The fermentation was carried out as batch process using double concentrated MRS-medium supplemented with 57.5 g/L arabinose as batch medium (see example 1). The pH-value was adjusted to 5.7 with 8 M Potassium hydroxide (KOH) throughout the whole process. Nitrogen ($N_2$) was used for gassing (2 L/h) during the fermentation.

The yield of lactic acid was 51 wt % (g lactic acid/g arabinose total) and a titer of 28.4 g/L lactic acid was obtained.

TABLE 10

Conversion of arabinose to lactic acid using *Lactobacillus diolivorans* DSM 14421 in a batch process

| Time [h] | $OD_{600}$ [AU] | arabinose [g/L] | lactic acid [g/L] | acetic acid [g/L] | ethanol [g/L] |
|---|---|---|---|---|---|
| 0.2 | 0.1 | 57.5 | 0.1 | 1.0 | 0.2 |
| 25.9 | 29.1 | 0.3 | 28.4 | 20.9 | 0.7 |

Example 11

Fermentation of Fructose into Mannitol with *Lactobacillus diolivorans* DSM 14421

Fermentation of fructose for the conversion into mannitol using *Lactobacillus diolivorans* DSM 14421 is given in Table 11. The fermentation was carried out in test glasses using MRS-medium supplemented with 21.2 g/L fructose (see example 1). The pH-value was adjusted to 5.7 in the beginning. The cultivation was carried out anaerobically.

The yield of lactic acid was 65 wt % (g mannitol/g fructose total) and a titer of 13.8 g/L mannitol was obtained.

TABLE 11

Conversion of fructose into mannitol using *Lactobacillus diolivorans* DSM 14421

| Time [h] | $OD_{600}$ [AU] | fructose [g/L] | mannitol [g/L] | lactic acid [g/L] | acetic acid [g/L] | ethanol [g/L] |
|---|---|---|---|---|---|---|
| 0 | 0.1 | 21.2 | 0.0 | 0.1 | 4.1 | 0.0 |
| 72 | 6.4 | 0.0 | 13.8 | 3.4 | 6.4 | 0.2 |

Example 12

Construction of a Plasmid (pSHM-GFP) Expressing Green Fluorescent Protein (GFP) and Isolation of Plasmid DNA for Transformation of *Lactobacillus dioliovorans* LMG 19668

A shuttle vector for GFP expression in *L. dioliovorans* (pSHM-GFP, FIG. 1) containing the elements listed in table 12 was constructed. Each element of the plasmid was amplified by PCR. The elements were purified by agarose gel electrophoresis and subsequent elution (Metabion). Finally, all elements were enzymatically assembled as described by Gibson, D. G. (2009) Nature Methods 6, 343-345.

TABLE 12

Description of the genetic elements from plasmid pSHM-GFP

| Element name | Description |
|---|---|
| GAP_Pro | Promoter of the *Lactobacillus dioliovorans* DSM 14421 gene for the Glyceraldehyde-3-phosphate dehydrogenase |
| GFP | Coding sequence for green fluorescent protein (GFP) |
| TT_CAT | Terminator of the chloramphenicol acetyltransferase gene |
| repA | Origin of replication, isolated from the endogenous plasmid from *Lactobacillus dioliovorans* DSM 14421 |
| ErmB_ErmBL | Erythromycin resistance cassette |
| Kan_ori | Kanamycin resistance cassette and *Escherichia coli* origin of replication |

The PCR was performed with Phusion® High-Fidelity DNA Polymerase (New England Biolabs) following the manufacturers protocol using the primer pairs as outlined in table 13 and the templates outlined in table 14:

TABLE 13

Primer pairs for PCR amplification of the genetic elements of plasmid pSHM-GFP

| Element name | PCR Primer Pair |
|---|---|
| GAP_Pro | GATAACAATTTCACACAGGAAACAGCACTAAGTTTT CCTCCTTTAGGAAAT (SEQ ID 5) |
|  | TAAACAGTTCTTCGCCTTTGCTCATACTAAGTTTTC CTCCTTTAGGAAAT (SEQ ID 6) |
| GFP | ATTTCCTAAAGGAGGAAAACTTAGTATGAGCAAAGG CGAAGAACTGTTTA (SEQ ID 7) |
|  | GTAAAAAGTACAGTCGGCATTATCTCATATTATTTA TACAGTTCATCCATGCCATG (SEQ ID 8) |
| TT_CAT | CATGGCATGGATGAACTGTATAAATAATATGAGATA ATGCCGACTGTACTTTTTAC (SEQ ID 9) |
|  | GCTTCTTTGCGTAACTCGTTAATTCGTCGGCATAGC GTGAGCTATTAAGC (SEQ ID 10) |
| repA | GCTTAATAGCTCACGCTATGCCGACGAATTAACGAG TTACGCAAAGAAGC (SEQ ID 11) |
|  | AACACACTCTAAGTTTGCTTCTAAGGCTCTTTAGCG TCTTTGAACTCGGTG (SEQ ID 12) |
| ErmB_ErmBL | CACCGAGTTCAAAGACGCTAAAGAGCCTTAGAAGCA AACTTAGAGTGTGTT (SEQ ID 13) |
|  | GTATATATGAGTAAACTTGGTCTGACAGTTACCTCC ATTCCCTTTAGTAACGTGTAACTT (SEQ ID 14) |

TABLE 13-continued

Primer pairs for PCR amplification of the genetic elements of plasmid pSHM-GFP

| Element name | PCR Primer Pair |
|---|---|
| Kan_ori | AAGTTACACGTTACTAAAGGGAATGGAGGTAACTGT CAGACCAAGTTTACTCATATATAC (SEQ ID 15) |
|  | ATTTCCTAAAGGAGGAAAACTTAGTGCTGTTTCCTG TGTGAAATTGTTATC (SEQ ID 16) |

TABLE 14

Templates for PCR amplification of the genetic elements of plasmid pSHM-GFP

| Element name | Template |
|---|---|
| GAP_Pro | Genomic DNA isolated from *L. dioliovorans* DSM 14421 |
| GFP | pGFPmut3.1 (Clontech) |
| TT_CAT | pC194, Horinouchi, S. and Weisblum, B. (1982) Nucleotide sequence and functional map of pC194, a plasmid that specifies inducible chloramphenicol resistance, J. Bacteriol. 150, 815-825 |
| repA | Plasmid DNA isolated from *L. dioliovorans* DSM 14421 |
| ErmB_ErmBL | pSIP409, Sorvig et al. (2005) High level, inducible gene expression in *Lactobacillus sakei* and *Lactobacillus plantarum* using versatile expression vectors. Microbiology 151, 2439-2449 |
| Kan_ori | pSTBlue (Novagen) |

The following cycling conditions were used:

| 1 | 98° C. | 1 min | |
|---|---|---|---|
| 2 | 98° C. | 10 s | |
| 3 | 70° C. | 30 s | } 15 times |
| 4 | 72° C. | elongation time as outlined in table 15 | |
| 5 | 98° C. | 10 s | |
| 6 | 55° C. | 30 s | } 30 times |
| 7 | 72° C. | elongation time as outlined in table 15 | |
| 8 | 72° C. | 10 min | |
| 9 | 25° C. | 2 min | |

TABLE 15

Elongation times for PCR amplification of the genetic elements of plasmid pSHM-GFP

| Element name | Elongation Time |
|---|---|
| GAP_Pro | 30 s |
| GFP | 30 s |
| TT_CAT | 30 s |
| repA | 90 s |
| ErmB_ErmBL | 30 s |
| Kan_ori | 60 s |

The assembled plasmid was transformed into *Escherichia coli* K12 ER 2925 (New England Biolabs) by standard electroporation in order to produce non-methylated plasmid DNA for the transformation of Lactobacillus diolivorans LMG 19668. Plasmid DNA was isolated with a Plasmid Maxi Kit (Qiagen) from overnight cultures on LB.

Example 13

Transformation of the Plasmid pSHM-GFP from Example 12 to *Lactobacillus diolivorans* LMG 19668 by Electroporation 50 ml MRS medium (example 1) supplemented with 2% (w/v) glucose was inoculated with 1.5 ml cryo culture of *Lactobacillus diolivorans* LMG 19668 and incubated overnight at 30° C. without shaking. 500 ml MRS medium (example 1) supplemented with 2% (w/v) glucose was inoculated with 50 ml overnight culture and incubated for 4 hours at 30° C. without shaking. After this incubation the cells were harvested by centrifugation for 10 min at 9000 g and resuspended in 200 ml of a buffer containing 100 mM Lithium acetate, 0.6 M sucrose, 10 mM Dithiothreitol (DTT) and 10 mM Tris HCl pH 7.5. Subsequently the cells were incubated for 30 min at room temperature on a shaker set to 120 rpm. Cells were then again centrifuged for 10 min at 9000 g and 4° C., and were kept cold (4° C. in the centrifuge or on ice) from that point on. Cells were washed five times with 100 ml 0.3 M sucrose, with the third washing buffer containing additionally 50 mM EDTA pH 8. The cells were finally resuspended in 1 ml of 0.3 M sucrose. A 45 µl aliquot together with 5 µl of DNA suspension (1 µg/µL) was mixed and loaded into an electroporation cuvette with 2 mm gap width.

Electroporation was carried out at 2000 V, 200 Ω, and 25 µF. Immediately after electroporation the cells were mixed with 950 µl of MRS medium (example 1) supplemented with 2% (w/v) glucose and 0.3 M sucrose and incubated for 2 h at 30° C. without shaking. The cell suspension was then plated to MRS plates (MRS medium, example 1, supplemented with 2% (w/v) glucose and 2% (w/v) agar-agar) containing 10 µg/ml Erythromycin and incubated at 30° C. for 3 days.

One colony was used to inoculate 1 ml MRS and incubated overnight at 30° C. without shaking. The cell suspension was centrifuged, washed with PBS buffer once and resuspended in the same buffer. Samples with an optical density of 1.0 and 0.5 were prepared by dilution for all three test cultures (wild type strain, pSHM-GFP clone 1 and pSHM-GFP clone 2).

The detection of fluorescence from GFP was carried out with a TECANreader Infinite®200, using an excitation wavelength of 488 nm, and an emission wavelength of 520 nm. Each sample was measured in triplicate.

TABLE 16

| Fluorescence from *L. diolivorans* cells (arbitrary units): | | |
|---|---|---|
| *L. diolivorans* LMG 19668 | $OD_{600} = 1.0$ | $OD_{600} = 0.5$ |
| wild type | 121 ± 5 | 101 ± 1 |
| pSHM-GFP clone 1 | 7461 ± 190 | 3908 ± 30 |
| pSHM-GFP clone 2 | 4788 ± 94 | 2483 ± 15 |
| blank | 78 ± 1 | |

The values show clearly the high fluorescence caused by the heterologous expression of GFP in *L. diolivorans*.

Example 14

Fermentation of Glucose and raw Glycerol from Canola (Hungary) into 1,3-propanediol with *Lactobacillus diolivorans* LMG 19668

Fermentation of glucose and raw glycerol from canola (purity less than Technical Grade) for the conversion of glycerol to 1,3-propanediol (1,3-PD) using *Lactobacillus diolivorans* LMG 19668 is given in Table 17. The fermentation was carried out as fed-batch process using MRS-medium supplemented with 30.6 g/L glucose and 9.9 g/L raw glycerol, and 5 mg/L Vitamin $B_{12}$ as batch medium (see example 2) and a glucose/glycerol solution (0.1 mol glucose/1 mol glycerol) supplemented with 5 mg/L Vitamin $B_{12}$, with a glycerol concentration of 467.4 g/L, as feed medium. The feed was started after glucose and glycerol were consumed from the batch culture medium (t=26 h). A rate of 1.5 mL/h was used to add the feed medium to the culture until the end of the process (t=189.9 h). Raw glycerol was obtained as described in Example 7.

The pH-value was adjusted to 6.2 with 8 M Potassium hydroxide (KOH) throughout the whole process. Nitrogen ($N_2$) was used for gassing (2 L/h) during the fermentation.

The yield of 1,3-propanediol was 48 wt % (g 1,3-propanediol/g glycerol total), 35 wt % (g 1,3-propanediol/g substrate total) and a titer of 64.3 g/L 1,3-propanediol was obtained.

TABLE 17

Conversion of raw glycerol from canola to 1,3-propanediol (1,3-PD), acetic acid and ethanol using *Lactobacillus diolivorans* LMG 19668 in a fed-batch process fermenting glucose and raw glycerol.

| Time [h] | $OD_{600}$ [AU] | glucose [g/L] | glycerol [g/L] | 1,3-PD [g/L] | lactic acid [g/L] | acetic acid [g/L] | ethanol [g/L] |
|---|---|---|---|---|---|---|---|
| 0.11 | 0.1 | 30.6 | 9.9 | 0.6 | 0.1 | 0.2 | 0.2 |
| 189.9 | 24.5 | 0.1 | 51.5 | 64.3 | 3.3 | 23.6 | 2.9 |

Example 15

Fermentation of Glucose and raw Glycerol from Palm oil (Thailand) into 1,3-propanediol with *Lactobacillus diolivorans* LMG 19668

Fermentation of glucose and raw glycerol from palm oil (Thail Oleochemical Co. Ltd.) with a purity of less than Technical Grade, for the conversion of glycerol to 1,3-propanediol (1,3-PD) using *Lactobacillus diolivorans* LMG 19668 is given in Table 18. The fermentation was carried out as fed-batch process using MRS-medium supplemented with 30.8 g/L glucose and 9.7 g/L raw glycerol, and 5 mg/L Vitamin $B_{12}$ as batch medium (see example 2) and a glucose/glycerol solution (0.1 mol glucose/1 mol glycerol) supplemented with 5 mg/L Vitamin $B_{12}$, with a glycerol concentration of 459.1 g/L, as feed medium. The feed was started after glucose and glycerol were consumed from the batch culture medium (t=26 h). A rate of 1.5 mL/h was used to add the feed medium to the culture until the end of the process (t=189.9 h). Raw glycerol was obtained as described in Example 7.

The pH-value was adjusted to 6.2 with 8 M Potassium hydroxide (KOH) throughout the whole process. Nitrogen ($N_2$) was used for gassing (2 L/h) during the fermentation.

The yield of 1,3-propanediol was 54 wt % (g 1,3-propanediol/g glycerol total), 39 wt % (g 1,3-propanediol/g substrate total) and a titer of 70.9 g/L 1,3-propanediol was obtained.

TABLE 18

Conversion of raw glycerol from palm oil to 1,3-propanediol (1,3-PD), acetic acid and ethanol using *Lactobacillus diolivorans* LMG 19668 in a fed-batch process fermenting glucose and raw glycerol

| Time [h] | $OD_{600}$ [AU] | glucose [g/L] | glycerol [g/L] | 1,3-PD [g/L] | lactic acid [g/L] | acetic acid [g/L] | ethanol [g/L] |
|---|---|---|---|---|---|---|---|
| 0.12 | 0.1 | 30.8 | 9.7 | 0.6 | 0.1 | 0.2 | 0.2 |
| 189.9 | 24.0 | 0.0 | 37.4 | 70.9 | 2.0 | 23.8 | 2.5 |

Example 16

Fermentation of Glucose and raw Glycerol from Palm oil (Thailand) into 1,3-propanediol with *Lactobacillus diolivorans* DSM 14421

Fermentation of glucose and raw glycerol from palm oil (Thai Oleochemical Co. Ltd.) with a purity of less than Technical Grade, for the conversion of glycerol to 1,3-propanediol (1,3-PD) using *Lactobacillus diolivorans* DSM 14421 is given in Table 19. The fermentation was carried out as fed-batch process using MRS-medium supplemented with 30.5 g/L glucose and 10.4 g/L raw glycerol, and 5 mg/L Vitamin $B_{12}$ as batch medium (see example 2) and a glucose/glycerol solution (0.1 mol glucose/1 mol glycerol) supplemented with 5 mg/L Vitamin $B_{12}$, with a glycerol concentration of 455.6 g/L, as feed medium. The feed was started after glucose and glycerol were consumed from the batch culture medium (t=21.5 h). A rate of 1.5 mL/h was used to add the feed medium to the culture until the end of the process (t=189.9 h). Raw glycerol was obtained as described in Example 7.

The pH-value was adjusted to 5.7 with 8 M Potassium hydroxide (KOH) throughout the whole process. Nitrogen ($N_2$) was used for gassing (2 L/h) during the fermentation.

The yield of 1,3-propanediol was 61 wt % (g 1,3-propanediol/g glycerol total), 45 wt % (g 1,3-propanediol/g substrate total) and a titer of 70.9 g/L 1,3-propanediol was obtained.

TABLE 19

Conversion of raw glycerol from palm oil to 1,3-propanediol (1,3-PD), acetic acid and ethanol using *Lactobacillus diolivorans* DSM 14421 in a fed-batch process fermenting glucose and raw glycerol

| Time [h] | $OD_{600}$ [AU] | glucose [g/L] | glycerol [g/L] | 1,3-PD [g/L] | lactic acid [g/L] | acetic acid [g/L] | ethanol [g/L] |
|---|---|---|---|---|---|---|---|
| 0.13 | 0.1 | 30.5 | 10.4 | 0.6 | 0.1 | 0.2 | 0.2 |
| 189.9 | 25.6 | 0.2 | 25.7 | 85.2 | 0.9 | 25.9 | 2.4 |

Example 17

Fermentation of Glucose and Glycerol into 1,3-propanediol with *Lactobacillus diolivorans* DSM 14421 with an Optimized feed Profile Fermentation of glucose and glycerol for the conversion of glycerol to 1,3-propanediol (1,3-PD) using *Lactobacillus diolivorans* DSM 14421 is given in Table 20. The fermentation was carried out as fed-batch process using MRS-medium supplemented with 31.7 g/L glucose and 10.3 g/L raw glycerol, and 5 mg/L Vitamin $B_{12}$ as batch medium (see example 2) and a glucose/glycerol solution (0.1 mol glucose/1 mol glycerol) supplemented with 5 mg/L Vitamin $B_{12}$, with a glycerol concentration of 491.8 g/L, as feed medium. The feed was started after glucose and glycerol were consumed from the batch culture medium (t=22 h). The feed rate was calculated with the following equation: y=−0.0062x+1.6019, where y is the feed rate in mL/h and x is the time in h.

The pH-value was adjusted to 5.7 with 8 M Potassium hydroxide (KOH) throughout the whole process. Nitrogen ($N_2$) was used for gassing (2 L/h) during the fermentation.

The yield of 1,3-propanediol was 65 wt % (g 1,3-propanediol/g glycerol total), 45 wt % (g 1,3-propanediol/g substrate total) and a titer of 69.7 g/L 1,3-propanediol was obtained.

TABLE 20

Conversion of glycerol to 1,3-propanediol (1,3-PD) using *Lactobacillus diolivorans* DSM 14421 in a fed-batch process fermenting glucose and glycerol

| Time [h] | OD$_{600}$ [AU] | glucose [g/L] | glycerol [g/L] | 1,3-PD [g/L] | lactic acid [g/L] | acetic acid [g/L] | ethanol [g/L] |
|---|---|---|---|---|---|---|---|
| 0.07 | 0.1 | 31.7 | 10.3 | 0.6 | 0.1 | 0.1 | 0.1 |
| 166.6 | 26.9 | 0.0 | 0.0 | 69.7 | 0.0 | 24.1 | 1.6 |

Example 18

Fermentation of Glucose and Glycerol into 1,3-propanediol with *Lactobacillus diolivorans* DSM 14421 with an Optimized feed Profile II Fermentation of glucose and glycerol for the conversion of glycerol to 1,3-propanediol (1,3-PD) using Lactobacillus diolivorans DSM 14421 is given in Table 21. The fermentation was carried out as fed-batch process using MRS-medium supplemented with 36.6 g/L glucose and 11.6 g/L raw glycerol, and 5 mg/L Vitamin $B_{12}$ as batch medium (see example 2) and a glucose/glycerol solution (0.1 mol glucose/1 mol glycerol) supplemented with 5 mg/L Vitamin $B_{12}$, with a glycerol concentration of 491.3 g/L, as feed medium. The feed was started after glucose and glycerol were consumed from the batch culture medium (t=22 h). The feed rate was calculated with the following equation: y=−0.0106x+2.6149, where y is the feed rate in mL/h and x is the time in h.

The pH-value was adjusted to 5.7 with 8 M Potassium hydroxide (KOH) throughout the whole process. Nitrogen ($N_2$) was used for gassing (2 L/h) during the fermentation.

The yield of 1,3-propanediol was 58 wt % (g 1,3-propanediol/g glycerol total), 42 wt % (g 1,3-propanediol/g substrate total) and a titer of 84.3 g/L 1,3-propanediol was obtained.

TABLE 21

Conversion of glycerol to 1,3-propanediol (1,3-PD) and 3-hydroxy propionic acid using *Lactobacillus diolivorans* DSM 14421 in a fed-batch process fermenting glucose and glycerol

| Time [h] | OD$_{600}$ [AU] | glucose [g/L] | glycerol [g/L] | 1,3-PD [g/L] | lactic acid [g/L] | acetic acid [g/L] | ethanol [g/L] |
|---|---|---|---|---|---|---|---|
| 0.20 | 0.1 | 36.6 | 11.6 | 0.7 | 0.1 | 0.2 | 0.1 |
| 189.5 | 25.0 | 0.6 | 0.4 | 84.3 | 0.9 | 30.1 | 1.0 |

26.6 g/L glycerol equivalents of 3-hydroxy propionic acid (according to RID value obtained for 3-hydroxypropionic acid as compared to the RID value of glycerol).

Example 19

Fermentation of Glucose and raw Glycerol (EGE KIMYA Sanayi ve Ticaret A. S) into 1,3-propanediol with *Lactobacillus diolivorans* DSM 14421.

Fermentation of glucose and raw glycerol (EGE KIMYA Sanayi ve Ticaret A. S, Turkey) with a purity of less than Technical Grade, for the conversion of glycerol to 1,3-propanediol (1,3-PD) using *Lactobacillus diolivorans* DSM 14421 is given in Table 22. The fermentation was carried out as fed-batch process using MRS-medium supplemented with 38.8 g/L glucose and 11.5 g/L raw glycerol, and 5 mg/L Vitamin $B_{12}$ as batch medium (see example 2) and a glucose/glycerol solution (0.1 mol glucose/1 mol glycerol) supplemented with 5 mg/L Vitamin $B_{12}$, with a glycerol concentration of 490.1 g/L, as feed medium. The feed was started after glucose and glycerol were consumed from the batch culture medium (t=21.5 h). The equation y=−0.0106x+2.6149, where y is the feed rate in mL/h and x is the time in h, was used to add the feed medium to the culture until the end of the process (t=186.8 h). Raw glycerol was obtained as described in Example 7.

The pH-value was adjusted to 5.7 with 8 M Potassium hydroxide (KOH) throughout the whole process. Nitrogen ($N_2$) was used for gassing (2 L/h) during the fermentation.

The yield of 1,3-propanediol was 63 wt % (g 1,3-propanediol/g glycerol total), 44 wt % (g 1,3-propanediol/g substrate total) and a titer of 84.3 g/L 1,3-propanediol was obtained.

TABLE 22

Conversion of raw glycerol to 1,3-propanediol (1,3-PD) using *Lactobacillus diolivorans* DSM 14421 in a fed-batch process fermenting glucose and raw glycerol

| Time [h] | $OD_{600}$ [AU] | glucose [g/L] | glycerol [g/L] | 1,3-PD [g/L] | lactic acid [g/L] | acetic acid [g/L] | ethanol [g/L] |
|---|---|---|---|---|---|---|---|
| 0.00 | 0.11 | 38.8 | 11.5 | 0.7 | 0.1 | 0.3 | 0.2 |
| 186.8 | 27.3 | 0.0 | 22.5 | 84.3 | 0.6 | 28.5 | 1.3 |

Example 20

Construction of a Plasmid (pSHM-PDODH(NADPH)) Expressing NADPH-dependent 1,3-propanediol Oxidoreductase and Isolation of Plasmid DNA for Transformation of *Lactobacillus diolivorans* LMG 19668

Figure 3:
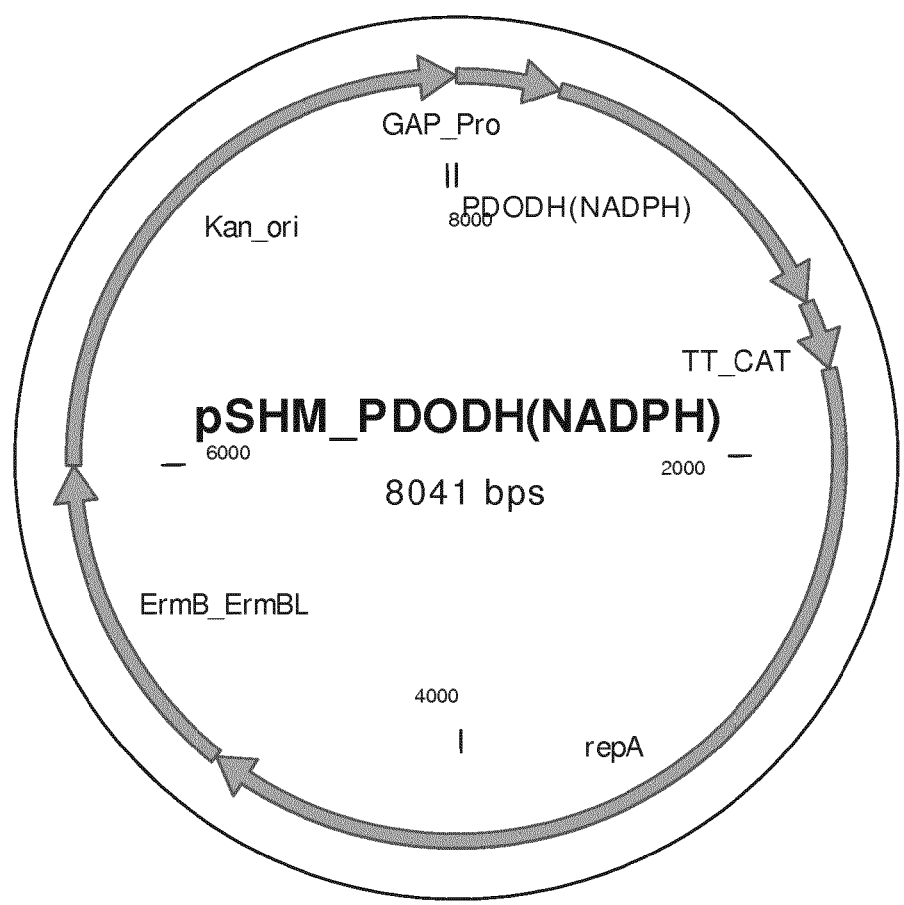

A shuttle vector for NADPH-dependent 1,3-Propanediol oxidoreductase expression in *L. diolivorans* (pSHM-PDODH (NADPH), FIG. 3) containing the elements listed in table 23 was constructed. Each element of the plasmid was amplified by PCR. The elements were purified by agarose gel electrophoresis and subsequent elution (Promega). Finally, all elements were enzymatically assembled as described by Gibson, D. G. (2009) Nature Methods 6, 343-345.

TABLE 23

Description of the genetic elements from plasmid pSHM-PDODH (NADPH)

| Element name | Description |
|---|---|
| GAP_Pro | Promoter of the *Lactobacillus diolivorans* DSM 14421 gene for the Glyceraldehyde-3-phosphate dehydrogenase |
| PDODH (NADPH) | Coding sequence for NADPH-dependent 1,3-Propanediol oxidoreductase from *Lactobacillus diolivorans* LMG 19668 |
| TT_CAT | Terminator of the chloramphenicol acetyltransferase gene |
| repA | Origin of replication, isolated from the endogenous plasmid from *Lactobacillus diolivorans* DSM 14421 |
| ErmB_ErmBL | Erythromycin resistance cassette |
| Kan_ori | Kanamycin resistance cassette and *Escherichia coli* origin of replication |

The PCR was performed with Phusion® High-Fidelity DNA Polymerase (New England Biolabs) following the manufacturers protocol using the primer pairs as outlined in table 13 and the templates outlined in table 14:

TABLE 24

Primer pairs for PCR amplification of the genetic elements of plasmid pSHM-GFP

| Element name | Primer Pair |
|---|---|
| GAP_Pro | GATAACAATTTCACACAGGAAACAGCACTAAGTTTTCCTCCTTTAGGAAAT (SEQ ID 17) |
| | TAAACAGTTCTTCGCCTTTGCTCATACTAAGTTTTCCTCCTTTAGGAAAT (SEQ ID 18) |
| PDODH (NADPH) | ATTTCCTAAAGGAGGAAAACTTAGTATGGAAGAAATTCGAATT (SEQ ID 19) |
| | GTAAAAAGTACAGTCGGCATTATCTCATATTAACGGATTACTTTCTTGT (SEQ ID 20) |
| TT_CAT | CATGGCATGGATGAACTGTATAAATAATATGAGATAATGCCGACTGTACTTTTTAC (SEQ ID 21) |
| | GCTTCTTTGCGTAACTCGTTAATTCGTCGGCATAGCGTGAGCTATTAAGC (SEQ ID 22) |
| repA | GCTTAATAGCTCACGCTATGCCGACGAATTAACGAGTTACGCAAAGAAGC (SEQ ID 23) |
| | AACACACTCTAAGTTTGCTTCTAAGGCTCTTTAGCGTCTTTGAACTCGGTG (SEQ ID 24) |

TABLE 24-continued

Primer pairs for PCR amplification of the genetic elements of plasmid pSHM-GFP

| Element name | Primer Pair |
| --- | --- |
| ErmB_ErmBL | CACCGAGTTCAAAGACGCTAAAGAGCCTTAGAAGCAAACTTAGAGTGTGTT (SEQ ID 25) |
| | GTATATATGAGTAAACTTGGTCTGACAGTTACCTCCATTCCCTTTAGTAACGTGTAACTT (SEQ ID 26) |
| Kan_ori | AAGTTACACGTTACTAAAGGGAATGGAGGTAACTGTCAGACCAAGTTTACTCATATATAC (SEQ ID 27) |
| | ATTTCCTAAAGGAGGAAAACTTAGTGCTGTTTCCTGTGTGAAATTGTTATC (SEQ ID 28) |

TABLE 25

Templates for PCR amplification of the genetic elements of plasmid pSHM-PDODH(NADPH)

| Element name | Template |
| --- | --- |
| GAP_Pro | Genomic DNA isolated from *L. diolivorans* DSM 14421 |
| PDODH(NADPH) | Genomic DNA isolated form *L. diolivorans* LMG 19668 |
| TT_CAT | pC194, Horinouchi, S. and Weisblum, B. (1982) Nucleotide sequence and functional map of pC194, a plasmid that specifies inducible chloramphenicol resistance, J. Bacteriol. 150, 815-825 |
| repA | Plasmid DNA isolated from *L. diolivorans* DSM 14421 |
| ErmB_ErmBL | pSIP409, Sorvig et al. (2005) High level, inducible gene expression in *Lactobacillus sakei* and *Lactobacillus plantarum* using versatile expression vectors. Microbiology 151, 2439-2449 |
| Kan_ori | pSTBlue (Novagen) |

The following cycling conditions were used:

| | | | |
| --- | --- | --- | --- |
| 1 | 98° C. | 1 min | |
| 2 | 98° C. | 10 s | |
| 3 | 70° C. | 30 s | 15 times |
| 4 | 72° C. | elongation time as outlined in table 15 | |
| 5 | 98° C. | 10 s | |
| 6 | 55° C. | 30 s | 30 times |
| 7 | 72° C. | elongation time as outlined in table 15 | |
| 8 | 72° C. | 10 min | |
| 9 | 25° C. | 2 min | |

TABLE 26

Elongation times for PCR amplification of the genetic elements of plasmid pSHM-PDODH(NADPH)

| Element name | Elongation Time |
| --- | --- |
| GAP_Pro | 30 s |
| PDODH(NADPH) | 45 s |
| TT_CAT | 30 s |
| repA | 90 s |
| ErmB_ErmBL | 30 s |
| Kan_ori | 60 s |

The assembled plasmid was transformed into *Escherichia coli* K12 ER 2925 (New England Biolabs) by standard electroporation in order to produce non-methylated plasmid DNA for the transformation of *Lactobacillus diolivorans* LMG 19668. Plasmid DNA was isolated with a Plasmid Maxi Kit (Qiagen) from overnight cultures on LB.

Example 21

Transformation of the Plasmid pSHM-PDODH(NADPH) from Example 12 to *Lactobacillus diolivorans* LMG 19668 with Optimized Electroporation Protocol 50 ml MRS medium (example 1) supplemented with 2% (w/v) glucose was inoculated with 1.5 ml cryo culture of *Lactobacillus diolivorans* LMG 19668 and incubated overnight at 30° C. without shaking. 500 ml MRS medium (example 1) supplemented with 2% (w/v) glucose and 1% (w/v) glycine was inoculated with 50 ml overnight culture and incubated for 4 hours at 30° C. without shaking. After this incubation the cells were harvested by centrifugation for 10 min at 9000 g and 4° C., and were kept cold (4° C. in the centrifuge or on ice) from that point on. Cells were washed five times with 100 ml 0.3 M sucrose, the third washing step additionally contained 50 mM EDTA pH 8. The cells were finally resuspended in 1 ml of an electroporation buffer containing 272 mM sucrose, 7 mM sodium phosphate and 1 mM $MgCl_2$ pH 7.4. A 80 µl aliquot together with 20 µl of DNA solution (DNA amount: 5 µg) was mixed and loaded into an electroporation cuvette with 4 mm gap width. Electroporation was carried out at 2500 V, 200 Ω, and 25 µF.

Immediately after electroporation the cells were mixed with 900 µl of MRS medium (example 1) supplemented with 2% (w/v) glucose and 0.3 M sucrose and incubated for 2 h at 30° C. without shaking. The cell suspension was then plated to MRS plates (MRS medium, example 1, supplemented with 2% (w/v) glucose and 2% (w/v) agar-agar) containing 10 µg/ml Erythromycin and incubated at 30° C. for 3 days.

3×50 ml MRS supplemented with 2% (w/v) glucose were inoculated with 1.5 ml cryo culture of the wild type strain, pSHM-PDODH (NADPH) clone 2 and pSHM-PDODH (NADPH) clone 9 and incubated overnight at 30° C. without shaking. 50 ml of MRS supplemented with 3% (w/v) glucose and 3% (w/v) glycerol and in case of the clones 10 µg/ml Erythromycin were inoculated with the overnight culture to an optical density of 0.1.2 ml portions of each strain were transferred into small reaction vessels and incubated in anaerobic containers at 30° C. and 150 rpm.

Growth was monitored by OD600, the 1,3-Propanediol concentration was monitored by HPLC. For ach strain six individual experiments were carried out.

TABLE 27

1,3-Propanediol and Qp for *L. diolivorans* strains:

| *L. diolivorans* LMG 19668 | 1,3-PDO [g/l] | $Q_p$ [g/l h] |
| --- | --- | --- |
| wild type | 9.6 ± 0.1 | 0.42 ± 0.01 |
| pSHM-PDODH (NADPH) clone 2 | 11.7 ± 0.1 | 0.53 ± 0.01 |
| pSHM-PDODH (NADPH) clone 9 | 11.7 ± 0.2 | 0.53 ± 0.01 |

The values clearly indicate improved 1,3-propanediol production by heterologous expression of NADPH-dependent 1,3-Propanediol oxidoreductase in *L. diolivorans*.

The invention claimed is:

1. A method of producing 1,3-propanediol by biotransforming industrial glycerol into 1,3-propanediol, comprising the steps:
   cultivating *Lactobacillus diolivorans* in the presence of the glycerol to produce 1,3-propanediol, wherein said glycerol has a purity of less than Technical Grade and an ash content of at least 0.1% (w/w), and
   isolating and purifying 1,3-propanediol.

2. The method according to claim 1, wherein the purified 1,3-propanediol comprises a purity of at least Technical Grade.

3. The method according to claim 1, wherein the *L. diolivorans* is derived from the DSM 14421, LMG 19668, or G77 strain.

4. The method according to claim 1, wherein a genetically engineered or recombinant strain of *L. diolivorans* is used.

5. The method according to claim 1, wherein the cultivating step is in a batch mode, fed-batch mode, or continuous mode.

6. The method according to claim 1, wherein the *L. diolivorans* is cultivated in a batch culture to accumulate biomass, followed by a fed-batch culture for conversion of the carbohydrate into the chemical substance.

7. The method according to claim 1, wherein the cultivating step comprises
   a) inoculating the *L. diolivorans* into a fermentation medium with the glycerol,
   b) culturing the *L. diolivorans* in a growth medium to accumulate biomass, and
   c) culturing the *L. diolivorans* in a production medium to produce the 1,3-propanediol.

8. The method according to claim 1, wherein the cultivating step is in a single batch to accumulate biomass and to produce 1,3-propanediol; or in separate batches (a) and (b), wherein said (a) batch accumulates biomass and said (b) batch produces 1,3-propanediol.

9. The method according to claim 1, wherein
   a lactic acid is further produced from lignocellulose or lignocellulosic biomass hydrolysate; or a
   mannitol is further produced from sugar beet extract or sugar beet hydrolysate.

* * * * *

```
                          SEQUENCE LISTING

<160> NUMBER OF SEQ ID NOS: 34

<210> SEQ ID NO 1
<211> LENGTH: 351
<212> TYPE: DNA
<213> ORGANISM: Lactobacillus diolivorans

<400> SEQUENCE: 1
actaagtttt cctcctttag gaaatagaaa atataattaa tagtacagat acaatcgtac    60
cactaaatga aaacaaagtc agcacccttg tgaaccaagg ctcaaagtgc gcctcgagta   120
aacattattt aattactcaa attcgagtat agcagaccat tttataaatg caacgcccag   180
aatttagtaa acgtttccat atgacacttt ttattacacc ttgaaatgta atcgattttc   240
tagtatattt atatagtaag ttgcgctcgt agtgtaatgg atcgcacgta agattccggt   300
tcttgaaatg agggttcgat tcccccgag cgcattatta aatgatgttt c             351

<210> SEQ ID NO 2
<211> LENGTH: 3180
<212> TYPE: DNA
<213> ORGANISM: Lactobacillus diolivorans

<400> SEQUENCE: 2
gaattaacga gttacgcaaa gaagccattg attactctac tagagaatct tatgtcacga    60
ccaaattatt ttttatcgcc aacatgatta aacacaatac aagatcatct cgtgagttat   120
taaaagcctt aaaagacgat cccaatgtat tggctacagt tccagaaaag gagctattca   180
atcgttcaac attggataaa aaatctcttt caaaaatggc agaagaccac aaaacatata   240
ttgatcaaca tgaatttttt gatagtatgg acaaaacatt taatgaaatc acagaaaaac   300
tataagtgtt ttgtacacgt gttaatcata tgtatatgca acatatgtat atgcaacata   360
tgtacgtgca acacatgtac atacgtattg taaaggagga ctacctatgg cattcgatcc   420
agagaacaaa aatataaaaa aggcactaca aaaaaatgaa acagaacaac caactgatac   480
taaagacaaa cttattattc ctgttttaa agatgaagag gaacgtacta agaactatac   540
cttttcactt caacctagcg cgcgcaaaag gcttgatggt ctggccaaag aacataattt   600
taagtctgcc tccaaatttt taaatgagct tataaaaaat atgtgatgtt acttagaata   660
aggaggagca ttatggggat tccaataaat ataacattct tgattgtcag tcttattgtt   720
ttctggataa ttccagttat tggaattgca aaaaagcgcc tggtagatga ccgctttttt   780
attcgacagt ggttatttcc aatgcagtat tggttacagc tattctttga aagaatcagt   840
ggtaaccgtc gtattgtcgt aagaattta cagataatgt ccctgtttat cacgtatttt   900
tgcgggttac ttatgctcat gattttcagt gttttgatg ggaatttgct taaacacccc   960
```

```
gaagcattttt tacttttcga atatttactg gtagcttcta tcgcttactg gtttcaacca   1020
aaagcaggca agtatacaa gaccaaataa agttgccgct tggtaagcgc tatgctagac     1080
taagactaat ttaacaaccg aataaagaga tcaatctaaa cagaaaaatc cccgattcac    1140
gaggaatcag ggattttggg tttagcaagt agctgctaga aagctactta gatccaatcg   1200
attttaactt gccggtgaaa atcgattgaa cgttgttctt aatttgtagg ttaattatac    1260
cgcaaaccgg tccaaaagga caagttaagg atagttaaaa aacaaattaa agtcaatgga   1320
ctaagtagct aaccgaagct gcctagtcca tttttgttta gttgctataa attaaaaaag   1380
ttgccggttg ggcaactcac aaacagacac atgctgatga aattgcaaag ccgatcacta   1440
ccaatgttcg ctttgtaatt cagttagagc atatcagatt tgtattttaa agcaaatcaa   1500
atgttttagc aactctcttt tgagacagcg tgtgtcagtc aagaaaggga gtttttatga   1560
tggatcaaac aaatttcaat tactatgaag ccgataacgt atatggagcc ctattttttcc  1620 agttccctaa ggtattaatg tatggcgatc aatacaagca tttaagcagt gacgctaaat   1680
tagcttatat ggtactcaaa gatcggctag agtattcgtt gagaaataac tgggttgatg   1740
aagataacca cgtttacttt atttttaccg ttcaagaatt acaagactta tttaattgtg   1800
ctactgaaaa agccgttaaa atcaaaaaag aattacaagc agccaattta ttaaaacaaa   1860
tccaaatggg atttaatccg aaaactaaaa agaatgaacc gaatcgttta taccttttcca  1920 aacttgatgt caaagccacc gatgtctatt tacgcggtga atatgagccg aaagcgccgc   1980
aatcccttgc tacgagcggg atttcgaaaa tcgaaagtcc gcatgacttc gctggaaccc   2040
ttgctacgag cgggatttcg aaaatcgaaa gtccgcatga cttcgttaaa gacaaccaga   2100
aaacccttgc tacgagcggg atttcgaaaa tcgaaagcaa tctatataaa gactttaaag   2160
atatagataa caatagatac aatatagata ctcaaaagtt agacttttcc acagcccaat   2220
tctcaccagc agaactagaa agcaaaaca aggatttggt gaaccatgct aatgatttct     2280
taactgatga agatagtggc ttacccgttt tcttagaacc cgaagccgta caattactta   2340
gtttctggtg ccgcaccccg caacaaatgc gccggtttat tggtattatc ttgaatgcta   2400
aatatcgagt tgaaaaggat catcaggaca ttggcgtcat aatcccactt gatgatgagg   2460
aactgaagcc tttaatgact aaagccttga ggcgctactt taacgccctg agaagtaatg   2520
agaagcatat caagaacgtt gaaaactact tgtacggcac catgcaaaac ttgtttggca   2580
tttggtggaa taaacaagcg gctagagaat atgcggccaa acaccccgaa gaagaaaaat   2640
cggccgacaa cgataacagt gggttgtact actagtccca aaaggctaca aaatcctttc   2700
taagcgattt taagacttac taacctattt atacttaagt tagatttaaa tggcttaaac   2760
agaagaatag gggcttttaa atgagtgtca gagctaacca ggctaaccag ctcaaaagtt   2820
cagcctttag atcaacgcca agctcaagtg atttgaggcc aaggctttat ctattgataa   2880
ggtactcaaa aggtagtata atggtagtgg taaaagaaag gagatgagac aatcatggca   2940
gttaaggaaa agaaacgggt ccaagtcaag attgataaag atttggccga tgataccgaa   3000
gcaattttaa gcgaattggg cttaaatcca accacggcca ttaacatgtt ttacaagcgg   3060
attgttgcta atggtgcttt accttttaat gcgtctttaa gcgaagaaga aaaagctaat   3120
ttacgctttt taaggcgac cgaagggaca ccagtcaccg agttcaaaga cgctaaagag   3180
```

<210> SEQ ID NO 3
<211> LENGTH: 7636
<212> TYPE: DNA
<213> ORGANISM: Artificial Sequence
<220> FEATURE:
<223> OTHER INFORMATION: Plasmid

<400> SEQUENCE: 3

```
gaaacatcat ttaataatgc gctcgggggg aatcgaaccc tcatttcaag aaccggaatc      60
ttacgtgcga tccattacac tacgagcgca acttactata taaatatact agaaaatcga     120
ttacatttca aggtgtaata aaaagtgtca tatggaaacg tttactaaat tctgggcgtt     180
gcatttataa aatggtctgc tatactcgaa tttgagtaat taaataatgt ttactcgagg     240
cgcactttga gccttggttc acaagggtgc tgactttgtt ttcatttagt ggtacgattg     300
tatctgtact attaattata ttttctattt cctaaaggag gaaaacttag tatgagcaaa     360
ggcgaagaac tgtttaccgg tgtggtgccg attctggtgg aactggatgg cgatgtgaac     420
ggtcataaat ttagcgtgag cggcgaaggt gaaggcgatg cgacctatgg taaactgacc     480
ctgaaattta tttgcaccac cggcaaactg ccggtgccgt ggccgaccct ggtgaccacc     540
tttggttatg gcgtgcagtg ctttgcgcgc tatccggatc acatgaaaca gcatgatttt     600
tttaaaagcg cgatgccgga aggttatgtg caggaacgca ccatttttt taaagatgat     660
ggcaactata aacccgcgc ggaagtgaaa tttgaaggtg ataccctggt gaaccgcatt     720
gaactgaaag gcattgattt taaagaagat ggtaacattc tgggccataa actggaatat     780
aactataaca gccataacgt gtatattatg gcggataaac agaaaaacgg tattaaagtg     840
aactttaaaa ttcgccataa cattgaagat ggcagcgtgc agctggcgga tcattatcag     900
cagaacaccc cgattggtga tggcccggtg ctgctgccgg ataaccatta tctgagcacc     960
cagagcgcgc tgagcaaaga tccgaacgaa aaacgcgatc acatggtgct gctggaattt    1020
gtgaccgcgg cgggtattac gcatggcatg gatgaactgt ataaataata tgagataatg    1080
ccgactgtac tttttacagt cggttttcta atgtcactaa cctgccccgt tagttgaaga    1140
aggttttat attacagctc cagatccata tccttctttt tctgaaccga cttctccttt    1200
ttcgcttctt tattccaatt gctttattga cgttgagcct cggaacccctt aacaatccca    1260
aaacttgtcg aatggtcggc ttaatagctc acgctatgcc gacgaattaa cgagttacgc    1320
aaagaagcca ttgattactc tactagagaa tcttatgtca cgaccaaatt attttttatc    1380
gccaacatga ttaaacacaa tacaagatca tctcgtgagt tattaaaagc cttaaaagac    1440
gatcccaatg tattggctac agttccagaa aaggagctat caatcgttc aacattggat    1500
aaaaaatctc tttcaaaaat ggcagaagac cacaaaacat atattgatca acatgaattt    1560
tttgatagta tggacaaaac atttaatgaa atcacagaaa aactataagt gttttgtaca    1620
cgtgttaatc atatgtatat gcaacatatg tatatgcaac atatgtacgt gcaacacatg    1680
tacatacgta ttgtaaagga ggactaccta tggcattcga tccagagaac aaaaatataa    1740
aaaaggcact acaaaaaaat gaaacagaac aaccaactga tactaaagac aaacttatta    1800
ttcctgtttt taaagatgaa gaggaacgta ctaagaacta tacctttca cttcaaccta    1860
gcgcgcgcaa aaggcttgat ggtctggcca agaacataa ttttaagtct gcctccaaat    1920
ttttaaatga gcttataaaa aatatgtgat gttacttaga ataaggagga gcattatggg    1980
gattccaata aatataacat tcttgattgt cagtcttatt gttttctgga taattccagt    2040
tattggaatt gcaaaaaagc gcctggtaga tgaccgcttt tttattcgac agtggttatt    2100
tccaatgcag tattggttac agctattctt tgaaagaatc agtggtaacc gtcgtattgt    2160
cgtaagaatt ttacagataa tgtccctgtt tatcacgtat ttttgcgggt tacttatgct    2220
```

```
catgattttc agtgttttg atgggaattt gcttaaacac cccgaagcat ttttactttt    2280
cgaatattta ctggtagctt ctatcgctta ctggtttcaa ccaaaagcag caaagtata    2340
caagaccaaa taaagttgcc gcttggtaag cgctatgcta gactaagact aatttaacaa    2400
ccgaataaag agatcaatct aaacagaaaa atccccgatt cacgaggaat cagggatttt    2460
gggtttagca agtagctgct agaaagctac ttagatccaa tcgattttaa cttgccggtg    2520
aaaatcgatt gaacgttgtt cttaatttgt aggttaatta taccgcaaac cggtccaaaa    2580
ggacaagtta aggatagtta aaaacaaat taaagtcaat ggactaagta gctaaccgaa    2640
gctgcctagt ccattttttgt ttagttgcta taaattaaaa aagttgccgg ttgggcaact    2700
cacaaacaga cacatgctga tgaaattgca agccgatca ctaccaatgt tcgctttgta    2760
attcagttag agcatatcag atttgtattt taaagcaaat caaatgtttt agcaactctc    2820
ttttgagaca gcgtgtgtca gtcaagaaag ggagtttttta tgatggatca aacaaatttc    2880
aattactatg aagccgataa cgtatatgga gccctatttt tccagttccc taaggtatta    2940
atgtatggcg atcaatacaa gcatttaagc agtgacgcta aattagctta tatggtactc    3000
aaagatcggc tagagtattc gttgagaaat aactggggttg atgaagataa ccacgtttac    3060
tttattttta ccgttcaaga attacaagac ttatttaatt gtgctactga aaaagccgtt    3120
aaaatcaaaa aagaattaca agcagccaat ttattaaaac aaatccaaat gggatttaat    3180
ccgaaaacta aaagaatga accgaatcgt ttatacctt ccaaacttga tgtcaaagcc    3240
accgatgtct atttacgcgg tgaatatgag ccgaaagcgc cgcaatccct tgctacgagc    3300
gggatttcga aaatcgaaag tccgcatgac ttcgctggaa cccttgctac gagcgggatt    3360
tcgaaaatcg aaagtccgca tgacttcgtt aaagacaacc agaaaaccct tgctacgagc    3420
gggatttcga aaatcgaaag caatctatat aaagactta aagatataga taacaataga    3480
tacaatatag atactcaaaa gttagacttt tccacagccc aattctcacc agcagaacta    3540
gaaaagcaaa acaaggattt ggtgaaccat gctaatgatt tcttaactga tgaagatagt    3600
ggcttacccg ttttcttaga acccgaagcc gtacaattac ttagtttctg gtgccgcacc    3660
ccgcaacaaa tgcgccggtt tattggtatt atcttgaatg ctaaatatcg agttgaaaag    3720
gatcatcagg acattggcgt cataatccca cttgatgatg aggaactgaa gcctttaatg    3780
actaaagcct tgaggcgcta ctttaacgcc ctgagaagta atgagaagca tatcaagaac    3840
gttgaaaact acttgtacgg caccatgcaa aacttgtttg gcatttggtg gaataaacaa    3900
gcggctagag aatatgcggc caaacacccc gaagaagaaa aatcggccga caacgataac    3960
agtgggttgt actactagtc ccaaaaggct acaaaatcct ttctaagcga ttttaagact    4020
tactaaccta tttatactta agttagattt aaatggctta aacagaagaa tagggggcttt    4080
taaatgagtg tcagagctaa ccaggctaac cagctcaaaa gttcagcctt tagatcaacg    4140
ccaagctcaa gtgatttgag gccaaggctt tatctattga taaggtactc aaaaggtagt    4200
ataatggtag tggtaaaaga aaggagatga gacaatcatg gcagttaagg aaaagaaacg    4260
ggtccaagtc aagattgata aagatttggc cgatgatacc gaagcaattt taagcgaatt    4320
gggcttaaat ccaaccacgg ccattaacat gttttacaag cggattgttg ctaatggtgc    4380
tttaccttt aatgcgtctt taagcgaaga agaaaaagct aatttacgct ttttaaaggc    4440
gaccgaaggg acaccagtca ccgagttcaa agacgctaaa gaccttagaa gcaaacttag    4500
agtgtgttga tagtgcatta tcttaaaatt ttgtataata ggaattgaag ttaaattaga    4560
tgctaaaaat aggaattgaa gttaaattag atgctaaaaa tttgtaatta agaaggaggg    4620
```

```
attcgtcatg ttggtattcc aaatgcgtaa tgtagataaa acatctactg ttttgaaaca    4680
gactaaaaac agtgattacg cagataaata aatacgttag attaattcct accagtgact    4740
aatcttatga cttttttaaac agataactaa aattacaaac aaatcgttta acttcaggag   4800
agattacatg aacaaaaata taaaatattc tcaaaacttt ttaacgagtg aaaaagtact    4860
caaccaaata ataaaacaat tgaatttaaa agaaaccgat accgtttacg aaattggaac    4920
aggtaaaggg catttaacga cgaaactggc taaaataagt aaacaggtaa cgtctattga    4980
attagacagt catctattca acttatcgtc agaaaaatta aaactgaata ctcgtgtcac    5040
tttaattcac caagatattc tacagtttca attccctaac aaacagaggt ataaaattgt    5100
tgggaatatt ccttacaatt taagcacaca aattattaaa aaagtggttt ttgaaagccg    5160
tgcgtctgac atctatctga ctgttgaaga aggattctac aagcgtacct tggatattca    5220
ccgaacacta gggttgctct tgcacactca agtctcgatt cagcaattgc ttaagctgcc    5280
agcggaatgc tttcatccta aaccaaaagt aaacagtgtc ttaataaaac ttacccgcca    5340
taccacagat gttccagata atattggaa gctatataag tactttgttt caaaatgggt    5400
caatcgagaa tatcgtcaac tgtttactaa aaatcagttt cgtcaagcaa tgaaacacgc    5460
caaagtaaac aatttaagta ccattactta tgagcaagta ttgtctattt ttaatagtta    5520
tctattattt aacgggagga aataattcta tgagtcgctt ttttaaattt ggaaagttac    5580
acgttactaa agggaatgga gcgtaactgt cagaccaagt ttactcatat atactttaga    5640
ttgatttaaa acttcatttt taatttaaaa ggatctaggt gaagatcctt tttgataatc    5700
tcatgaacaa taaaactgtc tgcttacata aacagtaata caagggtgt tatgagccat     5760 attcaacggg aaacgtcttg ctctaggccg cgattaaatt ccaacatgga tgctgattta    5820
tatgggtata aatgggctcg cgataatgtc gggcaatcag gtgcgacaat ctatcgattg    5880
tatgggaagc ccgatgcgcc agagttgttt ctgaaacatg gcaaaggtag cgttgccaat    5940
gatgttacag atgagatggt cagactaaac tggctgacgg aatttatgcc tcttccgacc    6000
atcaagcatt ttatccgtac tcctgatgat gcatggttac tcaccactgc gatccccggg    6060
aaaacagcat tccaggtatt agaagaatat cctgattcag gtgaaaatat tgttgatgcg    6120
ctggcagtgt tcctgcgccg gttgcattcg attcctgttt gtaattgtcc ttttaacagc    6180
gatcgcgtat ttcgtctcgc tcaggcgcaa tcacgaatga ataacggttt ggttgatgcg    6240
agtgattttg atgacgagcg taatggctgg cctgttgaac aagtctggaa agaaatgcat    6300
aaacttttgc cattctcacc ggattcagtc gtcactcatg gtgatttctc acttgataac    6360 cttattttg acgaggggaa attaataggt tgtattgatg ttggacgagt cggaatcgca    6420
gaccgatacc aggatcttgc catcctatgg aactgcctcg gtgagttttc tccttcatta    6480
cagaaacggc ttttttcaaaa atatggtatt gataatcctg atatgaataa attgcagttt    6540
catttgatgc tcgatgagtt tttctaagaa ttaattcatg accaaaatcc cttaacgtga    6600
gttttcgttc cactgagcgt cagaccccgt agaaaagatc aaaggatctt cttgagatcc    6660 ttttttttctg cgcgtaatct gctgcttgca acaaaaaaaa ccaccgctac cagcggtggt    6720
ttgtttgccg gatcaagagc taccaactct ttttccgaag gtaactggct tcagcagagc    6780
gcagatacca aatactgtcc ttctagtgta gccgtagtta ggccaccact tcaagaactc    6840
tgtagcaccg cctacatacc tcgctctgct aatcctgtta ccagtggctg ctgccagtgg    6900
cgataagtcg tgtcttaccg ggttggactc aagacgatag ttaccggata aggcgcagcg    6960
```

-continued

```
gtcgggctga acgggggtt cgtgcacaca gcccagcttg agcgaacga cctacaccga    7020
actgagatac ctacagcgtg agctatgaga aagcgccacg cttcccgaag ggagaaaggc    7080
ggacaggtat ccggtaagcg gcagggtcgg aacaggagag cgcacgaggg agcttccagg    7140
gggaaacgcc tggtatcttt atagtcctgt cgggtttcgc cacctctgac ttgagcgtcg    7200
attttgtga tgctcgtcag ggggcggag cctatggaaa aacgccagca acgcggcctt    7260
tttacggttc ctggccttt gctggccttt gctcacatg ttctttcctg cgttatcccc    7320
tgattctgtg gataaccgta ttaccgcctt tgagtgagct gataccgctc gccgcagccg    7380
aacgaccgag cgcagcgagt cagtgagcga ggaagcggaa gagcgcccaa tacgcaaacc    7440
gcctctcccc gcgcgttggc cgattcatta atgcagctgg cacgacaggt ttcccgactg    7500
gaaagcgggc agtgagcgca acgcaattaa tgtgagttag ctcactcatt aggcacccca    7560
ggctttacac tttatgcttc cggctcgtat gttgtgtgga attgtgagcg gataacaatt    7620
tcacacagga aacagc    7636
```

<210> SEQ ID NO 4
<211> LENGTH: 1491
<212> TYPE: DNA
<213> ORGANISM: Lactobacillus diolivorans

<400> SEQUENCE: 4

```
caggacgaac gctggcggcg tgcctaatac atgcaagtcg aacgcgtctt ggtcaatgat     60
tttaggtgct tgcacttgaa tgatttgaca ttaagacgag tggcgaactg gtgagtaaca    120
cgtgggtaac ctgcccttga agtagaggat aacacttgga aacaggtgct aatactgcat    180
aacaacgaaa accgcctggt tttcgtttga aagatggctt cggctatcgc tttaggatgg    240
acccgcggcg tattagctag ttggtgaggt aacggctcac caaggcaatg atacgtagcc    300
gacctgagag ggtaatcggc cacattggga ctgagacacg gcccaaactc ctacgggagg    360
cagcagtagg gaatcttcca caatggacga aagtctgatg gagcaacgcc gcgtgagtga    420
tgaagggttt cggctcgtaa aactctgttg ttggagaaga acgggtgtca gagtaactgt    480
tgacatcgtg acggtatcca accagaaagc cacggctaac tacgtgccag cagccgcggt    540
aatacgtagg tggcaagcgt tgtccggatt tattgggcgt aaagcgagcg caggcggttt    600
tttaggtctg atgtgaaagc cttcggctta accgagaag tgcatcggaa accgggagac    660
ttgagtgcag aagaggacag tggaactcca tgtgtagcgg tgaaatgcgt agatatatgg    720
aagaacacca gtggcgaagg cggctgtctg gtctgcaact gacgctgagg ctcgaaagca    780
tgggtagcga acaggattag ataccctggt agtccatgcc gtaaacgatg agtgctaagt    840
gttggagggt ttccgccctt cagtgctgca gctaacgcat taagcactcc gcctggggag    900
tacgaccgca aggttgaaac tcaaaggaat tgacggggc ccgcacaagc ggtggagcat    960
gtggtttaat tcgatgctac gcgaagaacc ttaccaggtc ttgacatctt ctgccaacct    1020
aagagattag gcgttccctt cggggacaga atgacaggtg gtgcatggtt gtcgtcagct    1080
cgtgtcgtga gatgttgggt taagtcccgc aacgagcgca acccttattg ttagttgcca    1140
gcatttagtt gggcactcta gcaagactgc cggtgacaaa ccgaggaag gtggggatga    1200
cgtcaaatca tcatgcccct tatgacctgg gctacacacg tgctacaatg gacggtacaa    1260
cgagtcgcga aaccgcgagg tcaagctaat ctcttaaagc cgttctcagt tcggattgta    1320
ggctgcaact cgcctacatg aagttggaat cgctagtaat cgtggatcag catgccacgg    1380
tgaatacgtt cccgggcctt gtacacaccg cccgtcacac catgagagtt tgtaacaccc    1440
```

```
aaagccggtg aggtaacctt cgggggccag ccgtctaggt gggacagatg a          1491
```

<210> SEQ ID NO 5
<211> LENGTH: 51
<212> TYPE: DNA
<213> ORGANISM: Artificial Sequence
<220> FEATURE:
<223> OTHER INFORMATION: Primer sequence

<400> SEQUENCE: 5

```
gataacaatt tcacacagga aacagcacta agttttcctc ctttaggaaa t          51
```

<210> SEQ ID NO 6
<211> LENGTH: 50
<212> TYPE: DNA
<213> ORGANISM: Artificial Sequence
<220> FEATURE:
<223> OTHER INFORMATION: Primer sequence

<400> SEQUENCE: 6

```
taaacagttc ttcgcctttg ctcatactaa gttttcctcc tttaggaaat            50
```

<210> SEQ ID NO 7
<211> LENGTH: 50
<212> TYPE: DNA
<213> ORGANISM: Artificial Sequence
<220> FEATURE:
<223> OTHER INFORMATION: Primer sequence

<400> SEQUENCE: 7

```
atttcctaaa ggaggaaaac ttagtatgag caaaggcgaa gaactgttta            50
```

<210> SEQ ID NO 8
<211> LENGTH: 56
<212> TYPE: DNA
<213> ORGANISM: Artificial Sequence
<220> FEATURE:
<223> OTHER INFORMATION: Primer sequence

<400> SEQUENCE: 8

```
gtaaaaagta cagtcggcat tatctcatat tatttataca gttcatccat gccatg    56
```

<210> SEQ ID NO 9
<211> LENGTH: 56
<212> TYPE: DNA
<213> ORGANISM: Artificial Sequence
<220> FEATURE:
<223> OTHER INFORMATION: Primer sequence

<400> SEQUENCE: 9

```
catggcatgg atgaactgta taaataatat gagataatgc cgactgtact ttttac    56
```

<210> SEQ ID NO 10
<211> LENGTH: 50
<212> TYPE: DNA
<213> ORGANISM: Artificial Sequence
<220> FEATURE:
<223> OTHER INFORMATION: Primer sequence

<400> SEQUENCE: 10

```
gcttctttgc gtaactcgtt aattcgtcgg catagcgtga gctattaagc            50
```

<210> SEQ ID NO 11
<211> LENGTH: 50
<212> TYPE: DNA

```
<213> ORGANISM: Artificial Sequence
<220> FEATURE:
<223> OTHER INFORMATION: Primer sequence

<400> SEQUENCE: 11
gcttaatagc tcacgctatg ccgacgaatt aacgagttac gcaaagaagc                50

<210> SEQ ID NO 12
<211> LENGTH: 51
<212> TYPE: DNA
<213> ORGANISM: Artificial Sequence
<220> FEATURE:
<223> OTHER INFORMATION: Primer sequence

<400> SEQUENCE: 12
aacacactct aagtttgctt ctaaggctct ttagcgtctt tgaactcggt g              51

<210> SEQ ID NO 13
<211> LENGTH: 51
<212> TYPE: DNA
<213> ORGANISM: Artificial Sequence
<220> FEATURE:
<223> OTHER INFORMATION: Primer sequence

<400> SEQUENCE: 13
caccgagttc aaagacgcta agagccttag aagcaaact tagagtgtgt t               51

<210> SEQ ID NO 14
<211> LENGTH: 60
<212> TYPE: DNA
<213> ORGANISM: Artificial Sequence
<220> FEATURE:
<223> OTHER INFORMATION: Primer sequence

<400> SEQUENCE: 14
gtatatatga gtaaacttgg tctgacagtt acctccattc cctttagtaa cgtgtaactt     60

<210> SEQ ID NO 15
<211> LENGTH: 60
<212> TYPE: DNA
<213> ORGANISM: Artificial Sequence
<220> FEATURE:
<223> OTHER INFORMATION: Primer sequence

<400> SEQUENCE: 15
aagttacacg ttactaaagg gaatggaggt aactgtcaga ccaagtttac tcatatatac     60

<210> SEQ ID NO 16
<211> LENGTH: 51
<212> TYPE: DNA
<213> ORGANISM: Artificial Sequence
<220> FEATURE:
<223> OTHER INFORMATION: Primer sequence

<400> SEQUENCE: 16
atttcctaaa ggaggaaaac ttagtgctgt ttcctgtgtg aaattgttat c              51

<210> SEQ ID NO 17
<211> LENGTH: 51
<212> TYPE: DNA
<213> ORGANISM: Artificial Sequence
<220> FEATURE:
<223> OTHER INFORMATION: Primer sequence

<400> SEQUENCE: 17
gataacaatt tcacacagga aacagcacta agttttcctc ctttaggaaa t              51
```

<210> SEQ ID NO 18
<211> LENGTH: 50
<212> TYPE: DNA
<213> ORGANISM: Artificial Sequence
<220> FEATURE:
<223> OTHER INFORMATION: Primer sequence

<400> SEQUENCE: 18
taaacagttc ttcgcctttg ctcatactaa gttttcctcc tttaggaaat                50

<210> SEQ ID NO 19
<211> LENGTH: 43
<212> TYPE: DNA
<213> ORGANISM: Artificial Sequence
<220> FEATURE:
<223> OTHER INFORMATION: Primer sequence

<400> SEQUENCE: 19
atttcctaaa ggaggaaaac ttagtatgga agaaattcga att                       43

<210> SEQ ID NO 20
<211> LENGTH: 49
<212> TYPE: DNA
<213> ORGANISM: Artificial Sequence
<220> FEATURE:
<223> OTHER INFORMATION: Primer sequence

<400> SEQUENCE: 20
gtaaaaagta cagtcggcat tatctcatat taacggatta ctttcttgt                 49

<210> SEQ ID NO 21
<211> LENGTH: 56
<212> TYPE: DNA
<213> ORGANISM: Artificial Sequence
<220> FEATURE:
<223> OTHER INFORMATION: Primer sequence

<400> SEQUENCE: 21
catggcatgg atgaactgta taataatat gagataatgc cgactgtact ttttac          56

<210> SEQ ID NO 22
<211> LENGTH: 50
<212> TYPE: DNA
<213> ORGANISM: Artificial Sequence
<220> FEATURE:
<223> OTHER INFORMATION: Primer sequence

<400> SEQUENCE: 22
gcttctttgc gtaactcgtt aattcgtcgg catagcgtga gctattaagc                50

<210> SEQ ID NO 23
<211> LENGTH: 50
<212> TYPE: DNA
<213> ORGANISM: Artificial Sequence
<220> FEATURE:
<223> OTHER INFORMATION: Primer sequence

<400> SEQUENCE: 23
gcttaatagc tcacgctatg ccgacgaatt aacgagttac gcaaagaagc                50

<210> SEQ ID NO 24
<211> LENGTH: 51
<212> TYPE: DNA
<213> ORGANISM: Artificial Sequence
<220> FEATURE:

```
<223> OTHER INFORMATION: Primer sequence

<400> SEQUENCE: 24
aacacactct aagtttgctt ctaaggctct ttagcgtctt tgaactcggt g          51

<210> SEQ ID NO 25
<211> LENGTH: 51
<212> TYPE: DNA
<213> ORGANISM: Artificial Sequence
<220> FEATURE:
<223> OTHER INFORMATION: Primer sequence

<400> SEQUENCE: 25
caccgagttc aaagacgcta agagccttag aagcaaact tagagtgtgt t           51

<210> SEQ ID NO 26
<211> LENGTH: 60
<212> TYPE: DNA
<213> ORGANISM: Artificial Sequence
<220> FEATURE:
<223> OTHER INFORMATION: Primer sequence

<400> SEQUENCE: 26
gtatatatga gtaaacttgg tctgacagtt acctccattc cctttagtaa cgtgtaactt  60

<210> SEQ ID NO 27
<211> LENGTH: 60
<212> TYPE: DNA
<213> ORGANISM: Artificial Sequences
<220> FEATURE:
<223> OTHER INFORMATION: Primer sequence

<400> SEQUENCE: 27
aagttacacg ttactaaagg gaatggaggt aactgtcaga ccaagtttac tcatatatac  60

<210> SEQ ID NO 28
<211> LENGTH: 51
<212> TYPE: DNA
<213> ORGANISM: Artificial Sequence
<220> FEATURE:
<223> OTHER INFORMATION: Primer sequence

<400> SEQUENCE: 28
atttcctaaa ggaggaaaac ttagtgctgt ttcctgtgtg aaattgttat c           51

<210> SEQ ID NO 29
<211> LENGTH: 351
<212> TYPE: DNA
<213> ORGANISM: Artificial Sequence
<220> FEATURE:
<223> OTHER INFORMATION: Genetic Element

<400> SEQUENCE: 29
actaagtttt cctcctttag gaaatagaaa atataattaa tagtacagat acaatcgtac  60
cactaaatga aaacaaagtc agcacccttg tgaaccaagg ctcaaagtgc gcctcgagta  120
aacattattt aattactcaa attcgagtat agcagaccat tttataaatg caacgcccag  180
aatttagtaa acgtttccat atgacacttt ttattacacc ttgaaatgta atcgattttc  240
tagtatattt atatagtaag ttgcgctcgt agtgtaatgg atcgcacgta agattccggt  300
tcttgaaatg agggttcgat tccccccgag cgcattatta aatgatgttt c           351

<210> SEQ ID NO 30
<211> LENGTH: 1122
```

<212> TYPE: DNA
<213> ORGANISM: Artificial Sequence
<220> FEATURE:
<223> OTHER INFORMATION: Genetic Element

<400> SEQUENCE: 30

| | | | | | |
|---|---|---|---|---|---|
| atggaagaaa | ttcgaattcc | aaccaaagtc | ttttcaggaa | atgatagctt | ggactggctg | 60 |
| gaaaaattgt | caaacaagaa | aattctgttg | gtatgtgatt | cgtttctacc | taatacacca | 120 |
| acatttgaca | caattaaaag | caaggttgaa | ggaaataacg | aggttacgat | tttctccgat | 180 |
| gtcaaaccag | acccaccgct | gcataacatt | atgctggggg | ttgaacaatt | tagtaaggtt | 240 |
| aagcccaatg | tcatgattgg | tattggtggt | ggttcggcaa | ttgataccgg | taaagcgatt | 300 |
| cggttctttg | gcgagaaaat | tgaaaagtat | gatattgaac | aatttattgc | catcccaaca | 360 |
| acgagtggaa | caggttccga | agttactaat | accagtgttg | tttccgatcc | tgaaaagcat | 420 |
| cagaagttcc | caatcatgga | agactattta | acaccggata | ttgctttact | ggatcctcga | 480 |
| ttggttatga | cggcacctaa | gagtgttact | gcattctcag | gcttggacgt | tttaacccat | 540 |
| tcactggaat | cattggttgc | caaagatgcc | aacacgatca | ctgaagcatt | atcagaaaaa | 600 |
| ggcattgatg | tcatgaccca | tctgttggtt | gaatgttata | agcatggtga | caatgaagat | 660 |
| gcaagaaagg | tcgttcacga | agcgtcatgt | gcagccggaa | ttgccttcaa | taacgctggt | 720 |
| ttaggaattt | gtcattcact | agctcaccaa | ttaggtgcca | actttcatgt | tcctcatggc | 780 |
| ttagcttgtg | ccatgttatt | gccacacgtt | gtttatacaa | cgctgaaca | tgacaagaca | 840 |
| gccatgcata | aatatgccca | ggctttcaaa | aagacgggct | tgttgctca | gggaatggga | 900 |
| gatcaaattg | ccgttcgtcg | tttagcgggt | aagatcaagc | aaatgatgat | cgcaatggat | 960 |
| tgtccattaa | ccctgaaagc | atttggaatt | gatccggcaa | ctgctgaatc | aaagacggaa | 1020 |
| acagttattg | cagatgcaaa | gaaggatggg | acattcccag | gaaatcctgt | tgtgccgtca | 1080 |
| gatgatgact | tgcgcaacat | ttacaagaaa | gtaatccgtt | aa | | 1122 |

<210> SEQ ID NO 31
<211> LENGTH: 235
<212> TYPE: DNA
<213> ORGANISM: Artificial Sequence
<220> FEATURE:
<223> OTHER INFORMATION: Genetic Element

<400> SEQUENCE: 31

| | | | | | |
|---|---|---|---|---|---|
| tatgagataa | tgccgactgt | acttttaca | gtcggttttc | taatgtcact | aacctgcccc | 60 |
| gttagttgaa | gaaggttttt | atattacagc | tccagatcca | tatccttctt | tttctgaacc | 120 |
| gacttctcct | ttttcgcttc | tttattccaa | ttgctttatt | gacgttgagc | ctcggaaccc | 180 |
| ttaacaatcc | caaaacttgt | cgaatggtcg | gcttaatagc | tcacgctatg | ccgac | 235 |

<210> SEQ ID NO 32
<211> LENGTH: 3179
<212> TYPE: DNA
<213> ORGANISM: Artificial Sequence
<220> FEATURE:
<223> OTHER INFORMATION: Genetic Element

<400> SEQUENCE: 32

| | | | | | |
|---|---|---|---|---|---|
| gaattaacga | gttacgcaaa | gaagccattg | attactctac | tagagaatct | tatgtcacga | 60 |
| ccaaattatt | tttatcgcc | aacatgatta | aacacaatac | aagatcatct | cgtgagttat | 120 |
| taaaagcctt | aaaagacgat | cccaatgtat | tggctacagt | tccagaaaag | gagctattca | 180 |

-continued

```
atcgttcaac attggataaa aaatctcttt caaaaatggc agaagaccac aaaacatata      240
ttgatcaaca tgaattttt  gatagtatgg acaaaacatt taatgaaatc acagaaaaac      300
tataagtgtt ttgtacacgt gttaatcata tgtatatgca acatatgtat atgcaacata      360
tgtacgtgca acacatgtac atacgtattg taaaggagga ctacctatgg cattcgatcc      420
agagaacaaa atataaaaa  aggcactaca aaaaaatgaa acagaacaac caactgatac      480
taaagacaaa cttattattc ctgtttttaa agatgaagag gaacgtacta agaactatac      540
cttttcactt caacctagcg cgcgcaaaag gcttgatggt ctggccaaag aacataattt      600
taagtctgcc tccaaatttt taaatgagct tataaaaaat atgtgatgtt acttagaata      660
aggaggagca ttatggggat ccaataaat  ataacattct tgattgtcag tcttattgtt      720
ttctggataa ttccagttat tggaattgca aaaaagcgcc tggtagatga ccgcttttt       780 attcgacagt ggttatttcc aatgcagtat tggttacagc tattctttga aagaatcagt      840
ggtaaccgtc gtattgtcgt aagaattta  cagataatgt ccctgtttat cacgtattt       900 tgcgggttac ttatgctcat gattttcagt gttttttgatg gaatttgct taaacacccc      960 gaagcatttt tacttttcga atatttactg gtagcttcta tcgcttactg gtttcaacca     1020 aaaagcaggca aagtatacaa gaccaaataa agttgccgct tggtaagcgc tatgctagac     1080
taagactaat ttaacaaccg aataaagaga tcaatctaaa cagaaaaatc cccgattcac     1140
gaggaatcag ggatttgg   tttagcaagt agctgctaga aagctactta gatccaatcg     1200
attttaactt gccggtgaaa atcgattgaa cgttgttctt aatttgtagg ttaattatac     1260
cgcaaaccgg tccaaaagga caagttaagg atagttaaaa aacaaattaa agtcaatgga     1320
ctaagtagct aaccgaagct gcctagtcca ttttttgttta gttgctataa attaaaaaag     1380
ttgccggttg ggcaactcac aaacagacac atgctgatga aattgcaaag ccgatcacta     1440
ccaatgttcg ctttgtaatt cagttagagc atatcagatt tgtattttaa agcaaatcaa     1500
atgttttagc aactctcttt tgagacagcg tgtgtcagtc aagaaaggga gttttttatga    1560 tggatcaaac aaatttcaat tactatgaag ccgataacgt atatggagcc ctattttcc      1620 agttccctaa ggtattaatg tatggcgatc aatacaagca tttaagcagt gacgctaaat     1680
tagcttatat ggtactcaaa gatcggctag agtattcgtt gagaaataac tgggttgatg     1740
aagataacca cgtttacttt atttttaccg ttcaagaatt acaagactta tttaattgtg     1800
ctactgaaaa agccgttaaa atcaaaaaag aattacaagc agccaattta ttaaaacaaa     1860
tccaaatggg atttaatccg aaaactaaaa agaatgaacc gaatcgttta tacctttcca    1920
aacttgatgt caaagccacc gatgtctatt tacgcggtga atatgagccg aaagcgccgc    1980
aatcccttgc tacgagcggg atttcgaaaa tcgaaagtcc gcatgacttc gctggaaccc     2040
ttgctacgag cgggatttcg aaaatcgaaa gtccgcatga cttcgttaaa gacaaccaga    2100
aaacccttgc tacgagcggg atttcgaaaa tcgaaagcaa tctatataaa gactttaaag    2160
atatagataa caatagatac aatatagata ctcaaaagtt agacttttcc acagcccaat    2220
tctcaccagc agaactagaa agcaaaaaca aggatttggt gaaccatgct aatgatttct    2280
taactgatga agatagtggc ttacccgttt tcttagaacc cgaagccgta caattactta    2340
gtttctggtg ccgcaccccg caacaaatgc gccggtttat tggtattatc ttgaatgcta    2400
aatatcgagt tgaaaaggat catcaggaca ttggcgtcat aatcccactt gatgatgagg    2460
aactgaagcc tttaatgact aaagccttga ggcgctactt taacgccctg agaagtaatg    2520
agaagcatat caagaacgtt gaaaactact tgtacggcac catgcaaaac ttgtttggca    2580
```

| | |
|---|---|
| tttggtggaa taaacaagcg gctagagaat atgcggccaa acaccccgaa gaagaaaaat | 2640 |
| cggccgacaa cgataacagt gggttgtact actagtccca aaaggctaca aaatcctttc | 2700 |
| taagcgattt taagacttac taacctattt atacttaagt tagatttaaa tggcttaaac | 2760 |
| agaagaatag gggcttttaa atgagtgtca gagctaacca ggctaaccag ctcaaaagtt | 2820 |
| cagcctttag atcaacgcca agctcaagtg atttgaggcc aaggctttat ctattgataa | 2880 |
| ggtactcaaa aggtagtata atggtagtgg taaaagaaag gagatgagac aatcatggca | 2940 |
| gttaaggaaa agaaacgggt ccaagtcaag attgataaag atttggccga tgataccgaa | 3000 |
| gcaattttaa gcgaattggg cttaaatcca accacggcca ttaacatgtt ttacaagcgg | 3060 |
| attgttgcta atggtgcttt accttttaat gcgtctttaa gcgaagaaga aaaagctaat | 3120 |
| ttacgctttt taaaggcgac cgaagggaca ccagtcaccg agttcaaaga cgctaaaga | 3179 |

<210> SEQ ID NO 33
<211> LENGTH: 1119
<212> TYPE: DNA
<213> ORGANISM: Artificial Sequence
<220> FEATURE:
<223> OTHER INFORMATION: Genetic Element

<400> SEQUENCE: 33

| | |
|---|---|
| ccttagaagc aaacttagag tgtgttgata gtgcattatc ttaaaatttt gtataatagg | 60 |
| aattgaagtt aaattagatg ctaaaaatag gaattgaagt taaattagat gctaaaaatt | 120 |
| tgtaattaag aaggagggat tcgtcatgtt ggtattccaa atgcgtaatg tagataaaac | 180 |
| atctactgtt ttgaaacaga ctaaaaacag tgattacgca gataaataaa tacgttagat | 240 |
| taattcctac cagtgactaa tcttatgact ttttaaacag ataactaaaa ttacaaacaa | 300 |
| atcgtttaac ttcaggagag attacatgaa caaaaatata aaatattctc aaaactttttt | 360 |
| aacgagtgaa aaagtactca accaaataat aaaacaattg aatttaaaag aaaccgatac | 420 |
| cgtttacgaa attggaacag gtaaagggca tttaacgacg aaactggcta aaataagtaa | 480 |
| acaggtaacg tctattgaat tagacagtca tctattcaac ttatcgtcag aaaaattaaa | 540 |
| actgaatact cgtgtcactt taattcacca agatattcta cagtttcaat tccctaacaa | 600 |
| acagaggtat aaaattgttg ggaatattcc ttcaaattta agcacacaaa ttattaaaaa | 660 |
| agtggttttt gaaagccgtg cgtctgcat ctatctgact gttgaagaag gattctacaa | 720 |
| gcgtaccttg gatattcacc gaacactagg gttgctcttg cacactcaag tctcgattca | 780 |
| gcaattgctt aagctgccag cggaatgctt tcatcctaaa ccaaaagtaa acagtgtctt | 840 |
| aataaaactt acccgccata ccacagatgt tccagataaa tattggaagc tatataagta | 900 |
| ctttgtttca aaatgggtca atcgagaata tcgtcaactg tttactaaaa atcagtttcg | 960 |
| tcaagcaatg aaacacgcca agtaaacaa tttaagtacc attacttatg agcaagtatt | 1020 |
| gtctattttt aatagttatc tattatttaa cgggaggaaa taattctatg agtcgctttt | 1080 |
| ttaaatttgg aaagttacac gttactaaag ggaatggag | 1119 |

<210> SEQ ID NO 34
<211> LENGTH: 2035
<212> TYPE: DNA
<213> ORGANISM: Artificial Sequence
<220> FEATURE:
<223> OTHER INFORMATION: Genetic Element

<400> SEQUENCE: 34

```
cgtaactgtc agaccaagtt tactcatata tactttagat tgatttaaaa cttcattttt      60
aatttaaaag gatctaggtg aagatccttt ttgataatct catgaacaat aaaactgtct     120
gcttacataa acagtaatac aagggtgtt atgagccata ttcaacggga aacgtcttgc      180
tctaggccgc gattaaattc aacatggat gctgatttat atgggtataa atgggctcgc     240
gataatgtcg ggcaatcagg tgcgacaatc tatcgattgt atgggaagcc cgatgcgcca     300
gagttgtttc tgaaacatgg caaaggtagc gttgccaatg atgttacaga tgagatggtc     360 agactaaaact ggctgacgga atttatgcct cttccgacca tcaagcattt tatccgtact    420
cctgatgatg catggttact caccactgcg atccccggga aaacagcatt ccaggtatta    480
gaagaatatc ctgattcagg tgaaaatatt gttgatgcgc tggcagtgtt cctgcgccgg    540
ttgcattcga ttcctgtttg taattgtcct tttaacagcg atcgcgtatt tcgtctcgct    600
caggcgcaat cacgaatgaa taacggtttg gttgatgcga gtgattttga tgacgagcgt    660
aatggctggc ctgttgaaca gtctggaaaa gaaatgcata aacttttgcc attctcaccg    720
gattcagtcg tcactcatgg tgatttctca cttgataacc ttattttga cgaggggaaa     780 ttaataggtt gtattgatgt tggacgagtc ggaatcgcag accgatacca ggatcttgcc    840
atcctatgga actgcctcgg tgagttttct ccttcattac agaaacggct ttttcaaaaa    900
tatggtattg ataatcctga tatgaataaa ttgcagtttc atttgatgct cgatgagttt    960
ttctaagaat taattcatga ccaaaatccc ttaacgtgag ttttcgttcc actgagcgtc    1020 agacccccgta gaaaagatca aaggatcttc ttgagatcct ttttttctgc gcgtaatctg   1080
ctgcttgcaa acaaaaaaac caccgctacc agcggtggtt tgtttgccgg atcaagagct   1140
accaactctt tttccgaagg taactggctt cagcagagcg cagataccaa atactgtcct   1200
tctagtgtag ccgtagttag gccaccactt caagaactct gtagcaccgc ctacatacct   1260
cgctctgcta atcctgttac cagtggctgc tgccagtggc gataagtcgt gtcttaccgg   1320
gttggactca agacgatagt taccggataa ggcgcagcgg tcgggctgaa cggggggttc   1380
gtgcacacag cccagcttgg agcgaacgac ctacaccgaa ctgagatacc tacagcgtga   1440
gctatgagaa agcgccacgc ttcccgaagg gagaaaggcg gacaggtatc cggtaagcgg   1500
cagggtcgga acaggagagc gcacgaggga gcttccaggg ggaaacgcct ggtatcttta   1560
tagtcctgtc gggtttcgcc acctctgact tgagcgtcga ttttgtgat gctcgtcagg    1620 ggggcggagc ctatggaaaa acgccagcaa cgcggccttt ttacggttcc tggccttttg   1680
ctggcctttt gctcacatgt tctttcctgc gttatcccct gattctgtgg ataaccgtat   1740
taccgccttt gagtgagctg ataccgctcg ccgcagccga acgaccgagc gcagcgagtc   1800
agtgagcgag gaagcggaag agcgcccaat acgcaaaccg cctctccccg cgcgttggcc   1860
gattcattaa tgcagctggc acgacaggtt tcccgactgg aaagcgggca gtgagcgcaa   1920
cgcaattaat gtgagttagc tcactcatta ggcaccccag gctttacact ttatgcttcc   1980
ggctcgtatg ttgtgtggaa ttgtgagcgg ataacaattt cacacaggaa acagc        2035
```